United States Patent [19]

Antalis et al.

[11] Patent Number: 5,426,044
[45] Date of Patent: * Jun. 20, 1995

[54] MINACTIVIN COMPOSITIONS AND ANTIBODIES TO MINACTIVIN

[75] Inventors: Toni M. Antalis, Drummoyne; Thomas M. Barnes, Lane Cove; Michelle A. Clark, Greenwich; Peter L. Devine, Gladesville; Neil H. Goss; Philip R. Lehrbach, both of Wahroonga, all of Australia

[73] Assignees: Biotechnology Australia, Pty., Ltd., New South Wales; Australian National University, Acton, both of Australia

[*] Notice: The portion of the term of this patent subsequent to Jun. 6, 2012 has been disclaimed.

[21] Appl. No.: 693,636

[22] Filed: Apr. 30, 1991

Related U.S. Application Data

[62] Division of Ser. No. 25,815, Mar. 13, 1987, abandoned.

[30] Foreign Application Priority Data

Mar. 13, 1986 [AU] Australia .................. PH5017
May 22, 1986 [AU] Australia .................. PH6033
Sep. 18, 1986 [AU] Australia .................. PH8100
Nov. 21, 1986 [AU] Australia .................. PH9104

[51] Int. Cl.$^6$ .................. C12N 9/00; A61K 39/00
[52] U.S. Cl. .................. 435/215; 424/94.64; 424/146.1; 514/2; 530/388.25; 530/388.26
[58] Field of Search .................. 424/85.8; 435/69.2, 435/215

[56] References Cited

U.S. PATENT DOCUMENTS 4,923,807  5/1990  Webb et al. .................. 435/69.2

Primary Examiner—Robert A. Wax
Assistant Examiner—David Schmickel
Attorney, Agent, or Firm—Foley & Lardner

[57] ABSTRACT

A novel human protein, minactivin, can be produced by recombinant DNA technology, Biologically active native minactivin, peptides derived from minactivin, and their amino acid sequences can also be purified.

5 Claims, 31 Drawing Sheets

ELUTION PROFILE OF
IMMUNOAFFINITY COLUMN

FIG. 23A

```
                                  1
                                  GTCAGACAGCAACTCAGAGAATAACCAGAGAACAACCAGATTGAAACA
                                                  109
49
ATG GAG GAT CTT TGT GTG GCA AAC ACA CTC TTT GCC CTC AAT TTA TTC AAG CAT CTG AAA GCA AGC CCC ACC CAG AAC CTC TTC CTC
Met Glu Asp Leu Cys Val Ala Asn Thr Leu Phe Ala Leu Asn Leu Phe Lys His Leu Ala Lys Ser Pro Thr Gln Asn Leu Phe Leu
139                                               169                                               199
TCC CCA TGG AGC ATC TCG AGC ATG GCC ATG GTC GCC ATG CAG GAC GAA TCC AGG GGC ATG CAG GAC ATC CAG AAG GTG CTT CAG TTT
Ser Pro Trp Ser Ile Ser Ser Met Ala Met Val Tyr Met Gly Ser Arg Gly Met Ala Lys Val Leu Gln Phe
229                                               259                                               289
AAT GAA GTG GGA GCC AAT GCA GTT ACT GCA GAG AAC TTT ACC CCA ATG TGT GGG TTC ATG GGT CCA ATC CAG ATC CAG AAG GGT AGT TAT
Asn Glu Val Gly Ala Asn Ala Val Thr Ala Glu Asn Phe Thr Pro Met Cys Gly Phe Met Gly Pro Ile Gln Ile Gln Lys Gly Ser Tyr
319                                               349                                               379
CCT GAT GCG ATT TTG GCA CAA GCT GCA GAT AAA ATC CAT TCA TCT CTC AGC TCT GCA ATC AAT GCA TCC ACA GGG AAT
Pro Asp Ala Ile Leu Ala Gln Ala Ala Asp Lys Ile His Ser Ser Leu Ser Ser Ala Ile Asn Ala Ser Thr Gly Asn
409                                               439                                               469
TAT TTA CTG GAA AGT GTC AAT GGG CTT TTT GGT GAG AAG TCT GCG AGC GAA GAA TAT CGA CTC TGT CAG CTC TAT TAC TCC
Tyr Leu Leu Glu Ser Val Asn Gly Leu Phe Gly Glu Lys Ser Ala Ser Glu Glu Tyr Ile Arg Leu Cys Gln Leu Tyr Tyr Ser
499                                               529                                               559
TCA GAA CCC CAG GCA GTA GAC TTC CTA GAA TGT GCA GAA ATT AAG AAG ATT AAT TCC TGG GTC AAG ACT CAA ACC AAA GGC AAA
Ser Glu Pro Gln Ala Val Asp Phe Leu Glu Cys Ala Glu Ile Lys Lys Ile Asn Ser Trp Val Lys Thr Gln Thr Lys Gly Lys
589                                               619                                               649
ATC CCA AAC TTG TTA CCT GAA GGT TCT GTA GAT GGG GAT AAT GCT GTC TAC TTC AAA GGA AAG TGG AAA ACT
Ile Pro Asn Leu Leu Pro Glu Gly Ser Val Asp Gly Asp Asn Ala Val Tyr Phe Lys Gly Lys Trp Lys Thr
        PEPTIDE 9
679                                               709                                               739
CCA TTT GAG AAG AAA CTA AAT GGG CTT TAT CCT GTA AAC CGC ACA CCT GTA CAG ATG TAC TTG CGT GAA AAG
Pro Phe Glu Lys Lys Leu Asn Gly Leu Tyr Pro Phe Arg Val Asn Ser Ala Gln Arg Thr Pro Val Gln Met Tyr Leu Arg Glu Lys
769                                               799                                               829
CTA AAC ATT GGA TAC ATA GAA GAT GAC CTA AAG GCT CTA GAA CTC CCA TAT GCT GGA GAT GTT AGC ATG TTG CTT CCA GAT
Leu Asn Ile Gly Tyr Ile Glu Val Glu Lys Leu Ala Gly Ile Leu Pro Tyr Ala Gly Asp Val Ser Met Phe Leu Leu Pro Asp
    PEPTIDE 6                                                        PEPTIDE 13
859                                               889                                               919
GAA ATT GCC GAT GTG TCC ACT GGC TTG GAG CTG GAG AGT GAA ATA ACC TAT GAC TAT GAG ATC ACT TAC AAC AAG TGG ACC AAA ATG
Glu Ile Ala Asp Val Ser Thr Gly Leu Glu Leu Glu Ser Glu Ile Thr Tyr Asp Tyr Glu Ile Thr Tyr Asn Lys Trp Thr Lys Met
949                                               979                                              1009
GCT GAA GAT GAA GTT GAG GAT GTA GTT GAG GTA GTT CCC CAG TTC AAA TTA GAA GAG CAT TAT GAA CTC AGA TCC ATT CTG AGA AGC ATG GAG
Ala Glu Asp Glu Val Glu Asp Val Val Glu Val Val Pro Gln Phe Lys Leu Glu Glu His Tyr Glu Leu Arg Ser Ile Leu Arg Ser Met Glu
                                    PEPTIDE 10
```

FIG. 23B

CELL ENVELOPE PREPARATIONS OF E. COLI
N4830 pBTA586 FROM UNINDUCED (30°c)
AND INDUCED (42°c) CULTURES SDS-PAGE

MINACTIVIN COMPOSITIONS AND ANTIBODIES TO MINACTIVIN

This application is a division of application No. 07/025,815, filed Mar. 13, 1987, now abandoned.

TECHNICAL FIELD

The present invention relates to the production of a novel human protein, minactivin, by recombinant DNA technology, the characterization of the DNA sequence of the gene, and the expression and purification of large quantities of biologically active minactivin from a recombinant host. It also relates to the purification of biologically active native minactivin, as well as peptides derived from minactivin and their amino acid sequences.

BACKGROUND ART

Minactivin (PAI-2) is a naturally occurring inactivator of urokinase-type plasminogen activators. This type of plasminogen activator is found in abnormally high levels in many major human carcinomas, most notably lung, colon, breast and prostate. Plasminogen activators are serine proteases which are thought to mediate the proteolytic cascade involved in cellular translocation, migration and invasion. As such, they appear to be associated with tissue destruction and remodelling, and have been implicated in tumor growth and metastasis. They may also have a role in inflammatory reactions.

Plasminogen activators are generally found to be of two types: 1) urokinase—type and 2) tissue—type. Tissue-type plasminogen activator is mainly found in the blood and blood vessel walls and where it is responsible for activating the fibrinolytic defence system against thrombosis. Urokinase-type plasminogen activators do not appear to play a role in normal thrombolytic processes but have been implicated in those pathological events associated with invasion and tissue destruction, in particular, tumor metastasis and inflammatory reactions.

Several inhibitors specific for plasminogen activators have been described with include one isolated from placenta (Holmberg, L. Biochim. Biophys. Acta 544, 128–137 (1978) and another (PAI-1) which is produced in cultured vascular endothelial cells (Van Mourik, J. A. Lawrence, D. A., Loskutoff, D. J., J. Biol. Chem., 259, 14914–14921 (1984)). Minactivin was found to be produced by blood monocytes and U937 cells and appears to be immunologically related to the placental inhibitor. The relationship between these various inhibitors is presently unknown.

As is the case with most other potent biologically active proteins, minactivin is produced in very small amounts in vivo, and as such, is difficult to purify and characterise by conventional biochemical approaches. Therefore, as large quantities of purified minactivin are required for further evaluation of its properties and biological efficacy in clinical applications, it is desirable to produce the protein using recombinant DNA techniques; that is, by cloning the minactivin gene into an alternate host, such as bacteria or animal cells. In order to clone minactivin it is desirable to purify to homogeneity the small amounts that can be so purified of naturally occurring minactivin in order to produce antibodies, amino acid sequences, peptide fragments and synthetic oligonucleotides derived from said purified minactivin. These reagents are of use in cloning strategies.

ABBREVIATIONS

HPLC—High pressure liquid chromatography
$M_r$—relative molecular mass
MW—molecular weight
PMA—4-phorbol-12-myristate-13-acetate
SDS-PAGE—sodium dodecyl sulfate polyacrylamide gel electrophoresis
TFA—trifluoroacetic acid
HPA—human plasminogen activator
bp—base pairs
kb—kilobase pairs
PU—Pluog

DESCRIPTION OF INVENTION

In a first embodiment, the invention provides a DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversion, to said first DNA sequence or hybridizing sequence or a DNA sequence which on expression codes for all, part, analogues, homogues, derivatives or combinations thereof a polypeptide which is minactivin or which displays similar immunological or biological activity in minactivin.

A preferred DNA sequence and fragments and derivatives thereof, according to the invention codes for a polypeptide displaying an immunological or biological activity of minactivin.

Such DNA sequences can be prepared for example from mammalian cells by extracting total DNA therefrom and isolating the sequences by standard techniques for preparation of recombinant molecules.

Also with the scope of the invention is a process for selecting a DNA sequence coding for a polypeptide displaying an immunological or biological activity of minactivin from a group of DNA sequences, which process comprises the step of: determining which of said DNA sequences hybridises to a DNA sequence known to code for a polypeptide displaying said activity.

The selected sequence may be, for example for natural sources, synthetic DNA sequences, DNA sequences from recombinant DNA molecules and DNA sequences which are a combination thereof.

A preferred embodiment of the invention provides a process for the manufacture of a cDNA sequence which acts as a coding sequence for amino acid sequences of minactivin, which process comprises the steps of: stimulating cells to produce minactivin; obtaining RNA from said stimulated cells; isolating mRNA therefrom; and producing said cDNA from said mRNA. Preferably the cells are U937 cells.

The more preferred process for molecular cloning the cDNA for minactivin and expression of the protein in a recombinant host includes the following methods:
1. induction of a cell line for stimulated minactivin production and expression.
2. isolation of mRNA from the appropriate cell line.
3. in vitro translation of the mRNA and immunoprecipitation of the minactivin translation product by complex formation with urokinase.

4. fractionation of mRNA from (2) and identification of the fraction containing minactivin translation activity.
5. construction of cDNA libraries from them RNA from (2) and (4).
6. cloning of the cDNA libraries from (5) into suitable hots, for example, *E. coli* or bacteriophage lambda.
7. identification of clones containing the minactivin gene by:
   a) hybrid-select translation employing (3);
   b) hybridization to a chemically synthesized DNA sequence probe, especially a probe comprising a synthetic oligonucleotide probe according to the invention;
   c) differential hybridization using labelled cDNA synthesized from induced and noninduced mRNA;
   d) immunological screening of cDNA expression libraries using antibodies directed against minactivin or other immunologically related molecules;
   e) screening of cDNA expression libraries for biological activity using labelled urokinase or urokinase and antibodies to urokinase.
8. extension of the cloned gene by generating dDNA libraries using oligonucleotides primers obtained from partial minactivin gene sequences, especially oligonucleotide sequences disclosed within the scope of the invention.
9. determination of the nucleotide sequence of the minactivin gene,
10. expression of the minactivin gene in *E. coli* and refolding to obtain biologically active product.
11. expression of biologically active recombinant minactivin by cloning into alternate hosts, for example, eukaryotic cells.
12. purification of recombination and clinical assessment of tis biological properties.

In a second embodiment, the invention provides a recombinant DNA molecule with includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof of a polypeptide which is minactivin or which displays similar immunological or biological activity to minactivin.

Preferred recombinant DNA molecules of the invention include an expression control sequence operatively linked to a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof a polypeptide which is minactivin or which displays similar immunological or biological activity to minactivin.

A preferred recombinant DNA molecule of the invention is a plasmid which acts as a coding sequence for amino acid sequences of minactivin.

A preferred plasmid of the invention has a first DNA sequence coding for a means of controlling expression of the DNA sequence of the invention linked to the DNA sequence of the invention.

The invention also provides a fused gene comprising a portable promoter, a translation start site, and a gene coding for human minactivin.

Also within the scope of the invention is a process for the manufacture of a recombinant DNA molecule, which process comprises the step of: introducing into a cloning vehicle, a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof a polypeptide which is minactivin or which displays similar immunological or biological activity to minactivin.

Preferably the process also includes the step of introducing an expression control sequence in the cloning vehicle.

The invention further provides a process for the manufacture of a plasmid which acts as a coding sequence for amino acid sequences of all, part, analogues, homologues, derivatives or combinations thereof of minactivin, which process comprises combining a plasmid with a DNA sequence which acts as a coding sequence for said amino acid sequences, and preferably with an expression control sequence. The DNA sequence is preferably a cDNA sequence.

In a third embodiment, the invention provides a host transformed with at least one recombinant DNA molecule which includes a first DNA sequence comprising a first DNA sequence which acts as a coding sequence for amino acid sequences of all, part, analogues, homologues, derivatives or combinations thereof minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part analogues, homologues, derivatives or combinations thereof of a polypeptide which is minactivin or which displays similar immunological or biological activity to minactivin.

Suitable hosts include bacteria, yeasts, other fungi, mice or other animal hosts, plant hosts, insects hosts and other eukaryotic hosts e.g. mammalian, including human tissue cells. Suitable bacteria include *E. coli*, Pseudomonas species, and Bacillus spaces.

Especially preferred is a microorganism with the genetic information for the biosynthesis of minactivin.

Also included within the invention is a process for transforming a host, which process comprises the step of: introducing into a host a recombinant DNA molecule which includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof a polypeptide which is minactivin or which displays similar immunological or biological activity to minactivin.

The invention also provides a process for the manufacture of a microorganism with the genetic information for the biosynthesis of all, part, analogues, homologues, derivatives or combinations thereof of minactivin, which process comprises transforming a microorganism with a plasmid or other vector which acts as a coding sequence for amino acid sequences of all, part analogues homologues, derivatives or combinations thereof minactivin.

In a fourth embodiment, the invention provides a process for the preparation of peptides derived from purified minactivin which process comprises purifying minactivin to homogeneity then obtaining amino acid sequences unique to minactivin.

A preferred embodiment of this process comprises:
a) Culturing a cell line capable of expressing minactivin;
b) harvesting the supernatant;
c) concentrating the supernatant;
d) dialysing the supernatant, then centrifuging said culture supernatant to remove residual cell debris and protein which may have precipitated during dialysis;
e) fractionating the culture supernatant chromatographically and electrophoretically;
f) concentrating the fraction containing minactivin activity;
g) analysing the fraction containing minactivin activity to demonstrate purity;
h) obtaining amino acid sequences unique to minactivin.

In a preferred form the process comprises:
a) culturing a minactivin producing culture or cell line;
b) harvesting the culture supernatant and concentrating said culture supernatant;
c) dialysing the culture supernatant, then centrifuging said culture supernatant to remove residual cell debris and protein which may have precipitated during dialysis;
d) fractionating the culture supernatant by ion exchange chromatography;
e) pooling and concentrating the eluates of highest minactivin specific activity;
f) fractionating the pooled, concentrated eluates by gel filtration chromatography;
g) concentrating the eluate then isoelectrofocussing said eluate;
h) probing fractions isolated from the isoelectrofocusing gel with antibodies reactive with minactivin, to locate the minactivin band;
i) concentrating the fraction containing minactivin activity;
j) further fractionating the fraction containing minactivin activity by partition chromatography than analysing the purified fraction containing minactivin activity by gel electrophoresis;
k) digesting the purified minactivin and separating the resulting peptides by partition chromatography.

In a more preferred form the culture is of the human macrophage cell line U937. Preferred culture conditions include culturing in the absence of serum and/or in the presence of a sufficient amount of a substance or substances which will inhibit urokinase production or induce constitutive production of minactivin. A suitable substance for this purpose is dexamethasone which is preferably used at a concentration of 1 $\mu$M. The culture may also be grown in the presence of PMA. A preferred concentration range of PMA in the culture is 1–300 ng/ml, more preferably 10–30 ng/ml.

A preferred volume of harvested culture supernatant is 4–5 liters. The initial concentration step is preferably a 10-fold concentration step. A suitable apparatus for this concentration is an Amicon DC2 Hollow Fibre Dialysis/Concentration unit equipped with a 30,000MW cut of cartridge.

The dialysis according to step c) is preferably with a dialysate such as 50 mM glycine, ph7.8 More preferably the 50 mM glycine pH7.8 dialysate should be used at at least equal volume to the volume of the sample being dialysed against said dialysate.

The ion exchange chromatography according to step d) is preferably performed on a phenyl-sepharose column, the elution being preferably a step pH elution. More preferably, for the pH step elution, the ionic strength of the supernatant should be adjusted to 2M, especially this may be by the addition of solid NaCl, then the pH should be adjusted to 5.5 preferably with citric acid. A preferred equilibrant for the phenyl-sepharose column is a solution of 50 mM Na citrate pH5.5, 2M NaCl and 1 mM EDTA. The column may be eluted initially with equilibration buffer, then with 50 mM Na citrate pH5.5 containing 0.5M NaCl and 1 mM EDTA and finally with 50 mM glycine pH9.0.

The concentration of the sample according to step g) is preferably performed on an Amicon YM10 membrane, with a final concentrate volume of 3 ml. The isoelectrofocussing step is preferably performed on a preparative flatbed gel of Ultrodex containing Ampholines in the pH range 4.5 to 6.0. More preferably the gel is electrofocussed at 10° C. for 23 hours. On an LKB Multiphor isolelectrofocussing apparatus. A preferred elutant for proteins from the electrofucssing gel is 1M glycine containing 1 mM EDTA pH9.0, more preferably in a 10 ml volume. Suitable antibodies according to step h) include goat anti-placental inhibitor antibodies.

The concentration according to step 1) may be performed on an Amicon YM10 membrane.

The partition chromatography according to step j) is preferably HPLC, more preferably performed on a Vydac C-4 reverse phase column using a Waters high pressure liquid chromatograph. The elution gradient is preferably acetonitrile in 0.1% TFA. Gel electrophoresis according to step j) is preferably SDS-PAGE.

Digestion of the purified minactivin, according to step k) is preferably with endoproteinase LysC. Suitable digestion conditions include 3-5 $\mu$g minactivin with 0.1 $\mu$g endoproteinase LysC in 20 mM Tris-Cl ph8.5., 5M urea, at a volume of 50 $\mu$l and 22° C. for 8 hours. A suitable form of partition chromatograph is reverse phase HPLC, particularly employing a Synchropak RP-P(C-8) column with a gradient of acetonitrile in 0.1% TFA.

In a fifth embodiment the invention provides minactivin in substantially pure form. Preferably said minactivin is purified to homogeneity.

In a sixth embodiment the invention provides purified minactivin when prepared by a process according to the invention.

In a seventh embodiment the invention provides peptides derived from purified minactivin and peptides displaying similar immunological or biological activity to said peptides.

Preferred peptides according to the invention include peptides of the following sequences and which are also set forth in SEQ. ID. Nos. 1, 2, 3, 4 and 5, respectively;

AQILELPY-GDV-MFLLLP-3 . .
GRANFSGMSE-NDLF. . .
MAE-EVEVYIPQFKLEE-Y. . .
LNIGYIEDLK
IPNLLPEG-V

The invention also provides peptides according to the invention when prepared by a process according to the invention.

In an eighth embodiment, the invention provides a microbiologically prepared peptide, all or part of which contains the amino acid sequence of all, part, analogues, homologues, derivatives or combinations thereof minactivin.

A peptide and fragments and derivatives thereof which display an immunological or biological activity of minactivin are also within the scope of the present invention.

The preferred peptide or fragments or derivatives thereof are coded for by a DNA sequence which hybridises to a DNA sequence which acts as a coding sequence for amino acid sequences of minactivin and displays the biological or immunological activity of minactivin, which activity is destroyed by antisera to minactivin.

The invention also provides a process for the manufacture of all, part, analogues, homologues, derivatives or combinations thereof of unglycosylated minactivin, which process comprises the steps of: obtaining the genetic information for the biosynthesis of minactivin using mRNA from cells of monocytic lineage; incorporating the resulting gene into a microorganism; selecting and culturing said microorganism to produce said minactivin; and collecting said minactivin.

The invention further provides a process for the manufacture of a peptide displaying an immunological or biological activity of minactivin, which process comprises the steps of: culturing a host which has been transformed with recombinant DNA molecule which includes a first DNA sequence comprising a first DNA sequence which acts as a coding sequence for amino acid sequences of all, part, analogues, homologues, derivatives or combinations thereof of minactivin, a DNA sequence which hybridizes to said first DNA sequence, a DNA sequence related by mutation, including single or multiple base substitutions, deletions, insertions and inversions, to said first DNA sequence or hybridizing sequence or a DNA sequence which on expression codes for all, part, analogues, homologues, derivatives or combinations thereof a polypeptide which is minactivin or which displays similar immunological or biological activity to minactivin.

The invention also provides a reagent for locating and defining the boundaries of tumours in histological specimens or in vivo which reagent comprises suitable labelled minactivin, especially recombinant DNA derived minactivin, or fragments of minactivin and the associated method of locating and defining the boundaries of tumours is histological specimens or in vivo whichcomprises applying or administering suitably labelled minactivin or fragments thereof and subsequently imaging to determine the site of concentration of the label.

The invention further provides a method of inhibiting tumour invasion and treating tumours comprising administering to a patient requiring such treatment a therapeutically effective amount of minactivin, suitably labelled minactivin, fragments of minactivin or labelled fragments of minactivin; a method of treatment of chronic inflammation such as rheumatoid arthritis comprising administering to a patient requiring such treatment a therapeutically effective amount of minactivin or fragments of minactivin; and a method of monitoring chronic inflammation comprising the detection of minactivin in samples of body fluids and tissues using antibodies prepared against minactivin or fragments of minactivin.

Also included within the invention are antibody preparations prepared against minactivin including recombinant minactivin, purified natural minactivin and fragments thereof. The invention also provides therapeutic, diagnostic or phrophylactic compositions which comprise minactivin, especially recombinant DNA derived minactivin, fragments of minactivin or antibodies to minactivin or fragments of minactivin and a pharmaceutically acceptable non-toxic carrier or diluent therefor.

The invention further provides synthetic olignoculeotide probes, the sequence of said probes comprising a first nucleotide sequence which on expression codes for the amino acid sequence of a peptide according to the invention, a nucleotide sequence sufficiently related to said first nucleotide sequence to hybridize to said first nucleotide sequence or a DNA sequence related by mutation including single or multiple base insertions, inversions deletions or substitutions to said first nucleotide sequence.

Included within the scope of the invention is a process for the production of said synthetic oligonucleotide probes which process comprises determining the amino acid sequence of peptide fragments derived from purified minactivin and synthesizing corresponding oligonucleotides. In a preferred form said synthesis is performed on an Applied Biosystems 380A DNA synthesizer.

The invention provides formulations comprising synthetic olignoucleotide probes according to the invention.

Preferably said formulations are diagnostic reagents.

The invention also provides a method for the detection of human carcinomas and inflammatory conditions and susceptibility thereto which method comprises using a formulation comprising said synthetic oligonucleotide probe in an assay designed for the detection of DNA coding for minactivin. Deficiency in ability of tissues to produce minactivin may be related to susceptibility to carcinomas and inflammatory conditions. Detected deficiencies may be treated by administration of purified minactivin to the patient, and may also serve as a marker for tissues affected by carcinomas and inflammation.

A:elution with 50 mM sodium citrate, pH5.5, 1 mMEDTA, 0.5M sodium chloride.

B:elution with 50 mM glycine, ph9.0.

Figure 15:
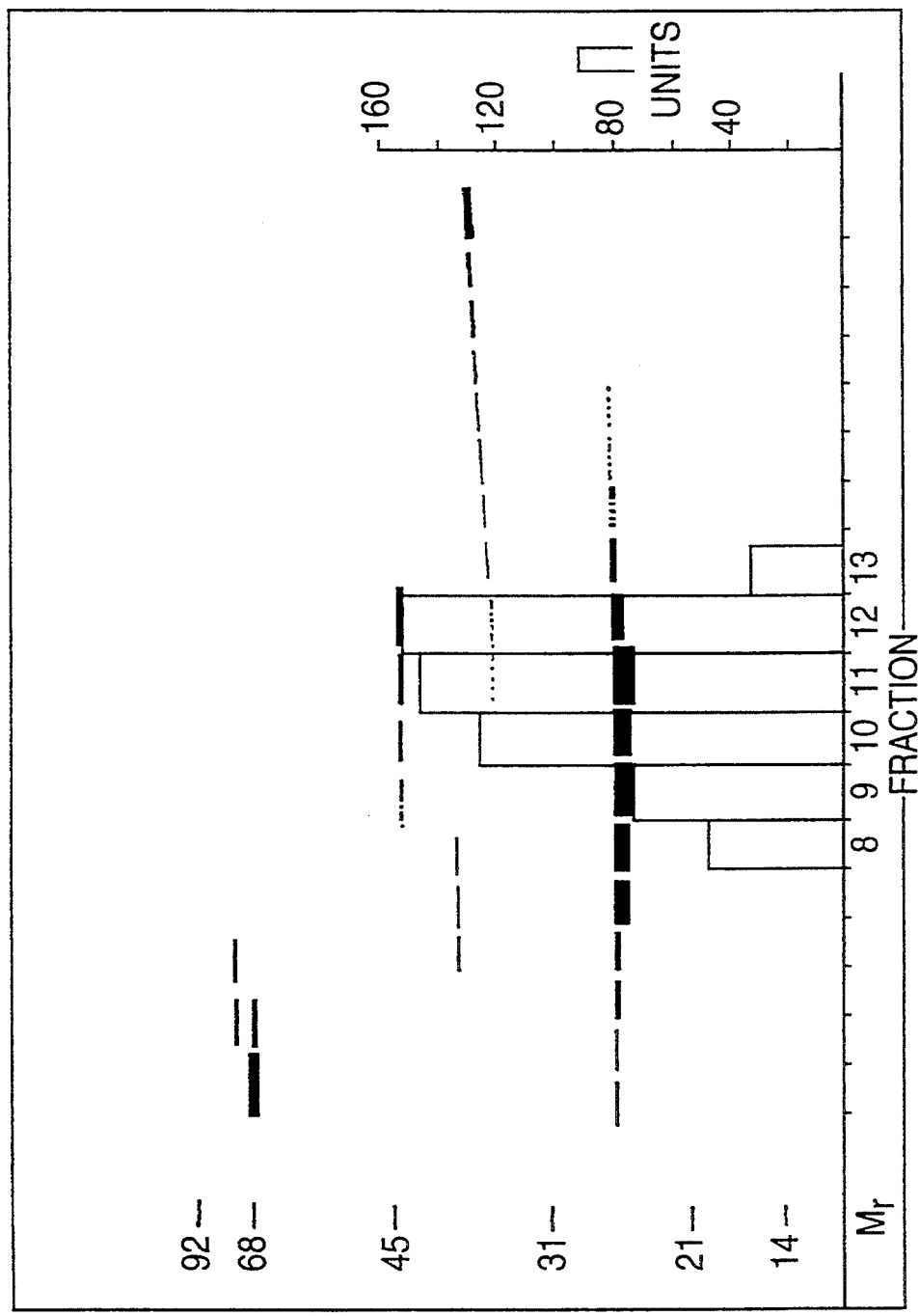

FIG. 15 is a superimposition of minactivin activity over an SDS-PAGE gel of the protein fractions isolated from an isoelectric focussing gel to demonstrate protein content versus minactivin activity.

Figure 16:
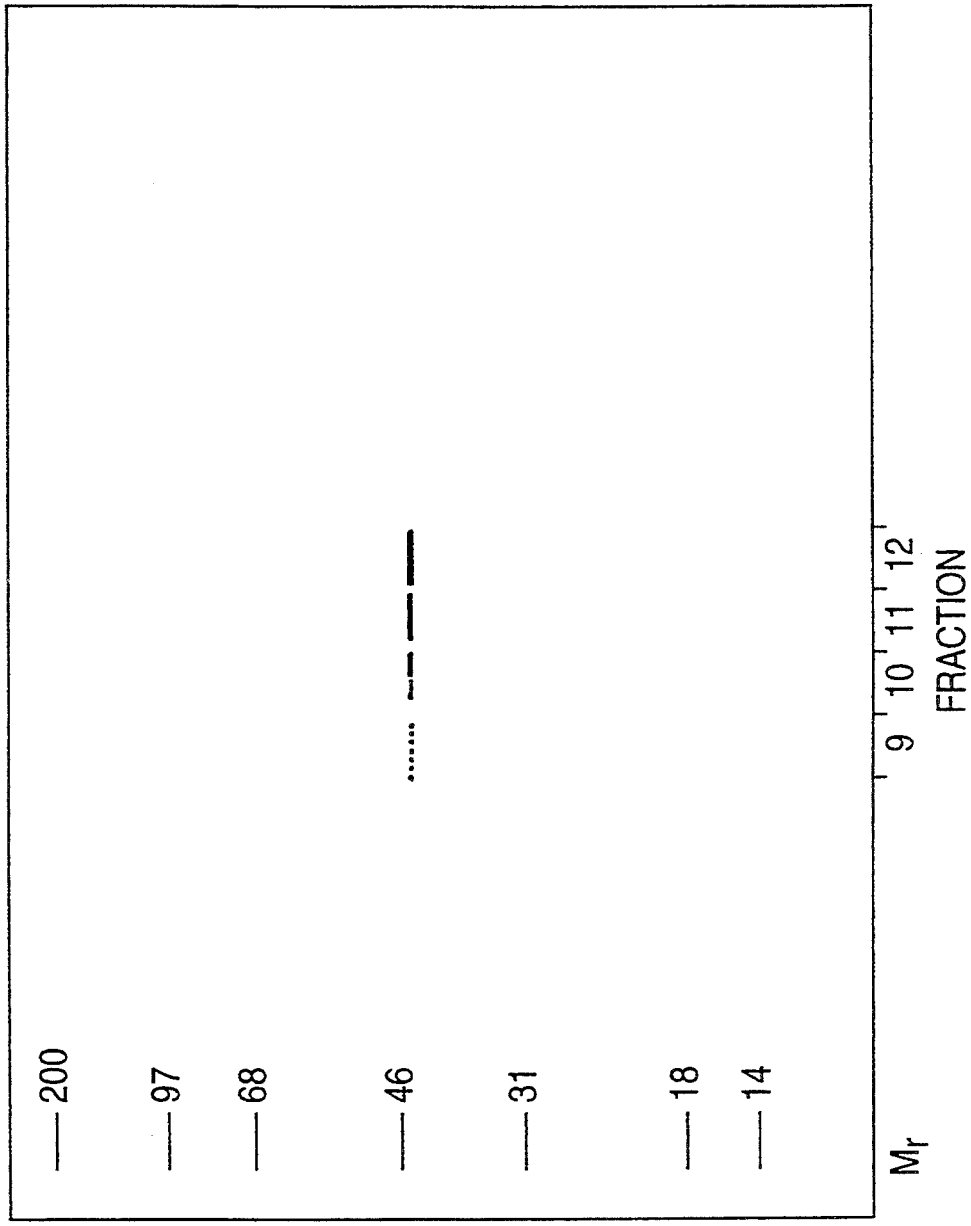

FIG. 16 is a representation of the fractions from the isoelectric focussing experiment shown in FIG. 15 after Western transfer of the protein onto nitrocellulose and immunological detection of the proteins with anti-placental inhibitor antibodies.

Figure 17:
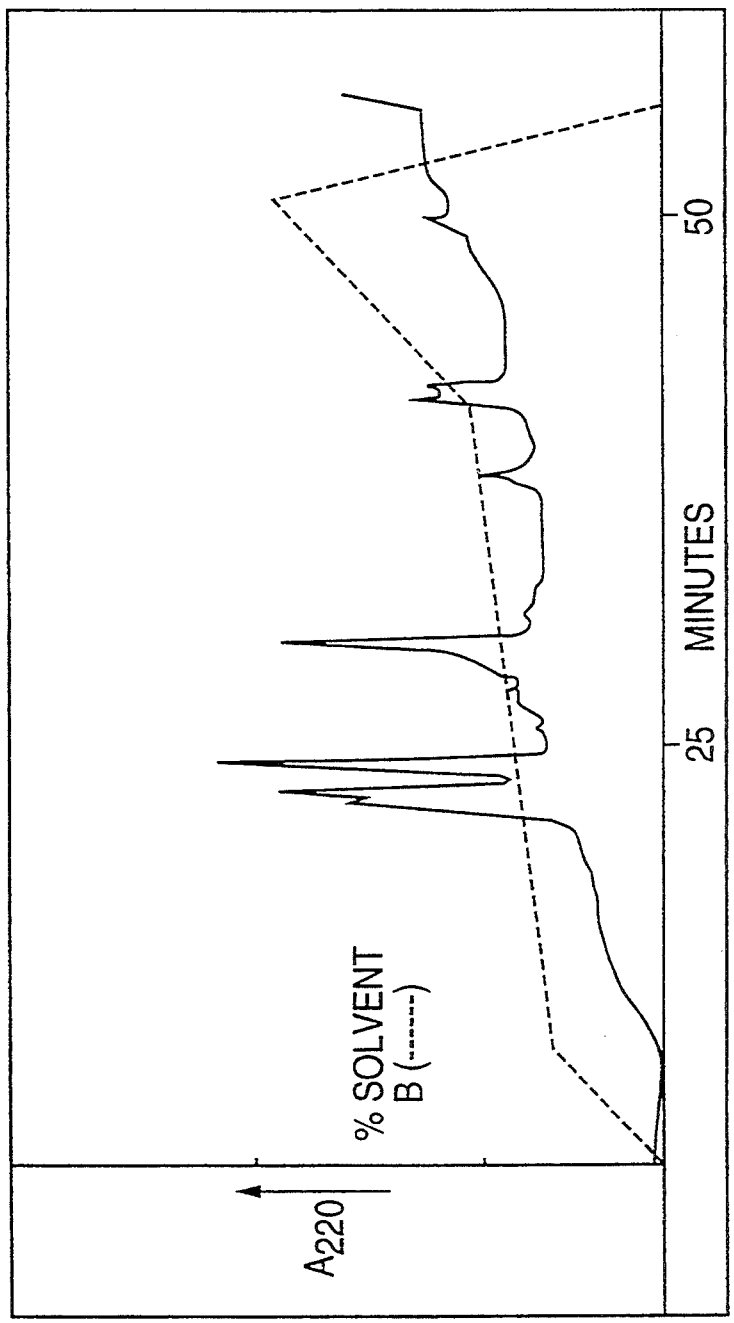

FIG. 17 shows an elution profile of the highly purified minactivin preparation from a Vydac C-4 reverse phase high pressure liquid chromatography run.

Figure 18:
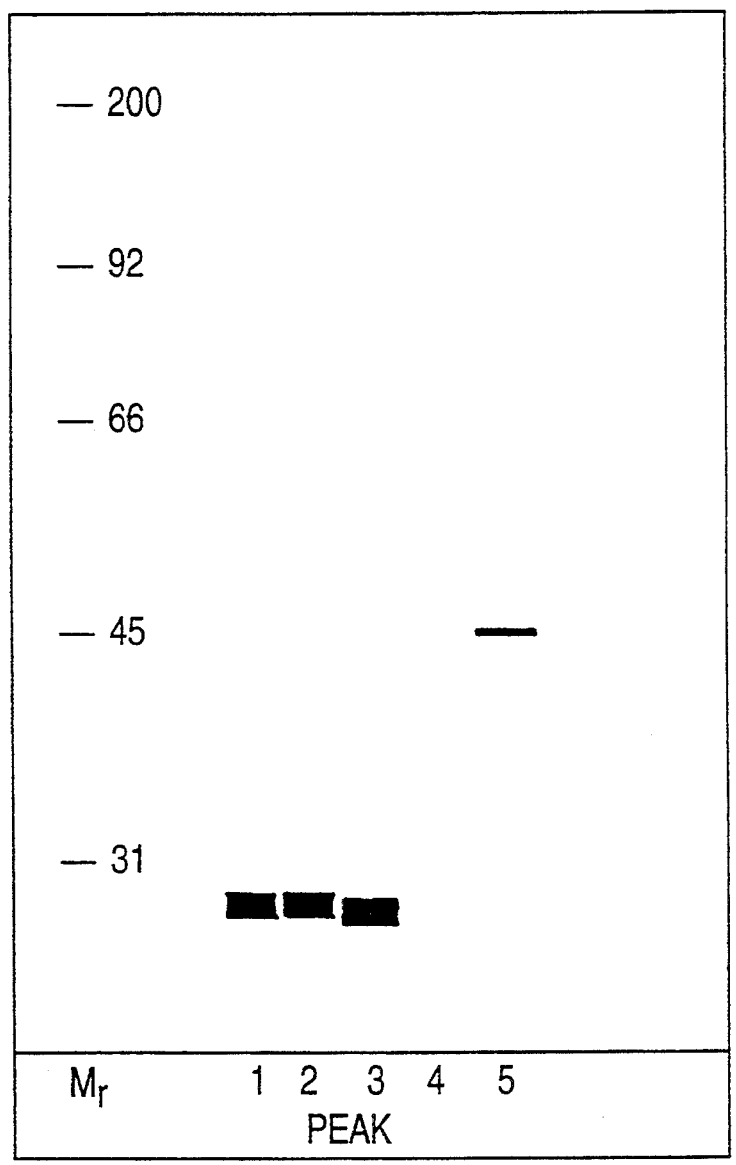

FIG. 18 is a representation of an SDS-PAGE showing homogeneous minactivin obtained from peak 5 of the HPLC run shown in FIG. 17.

Figure 19:
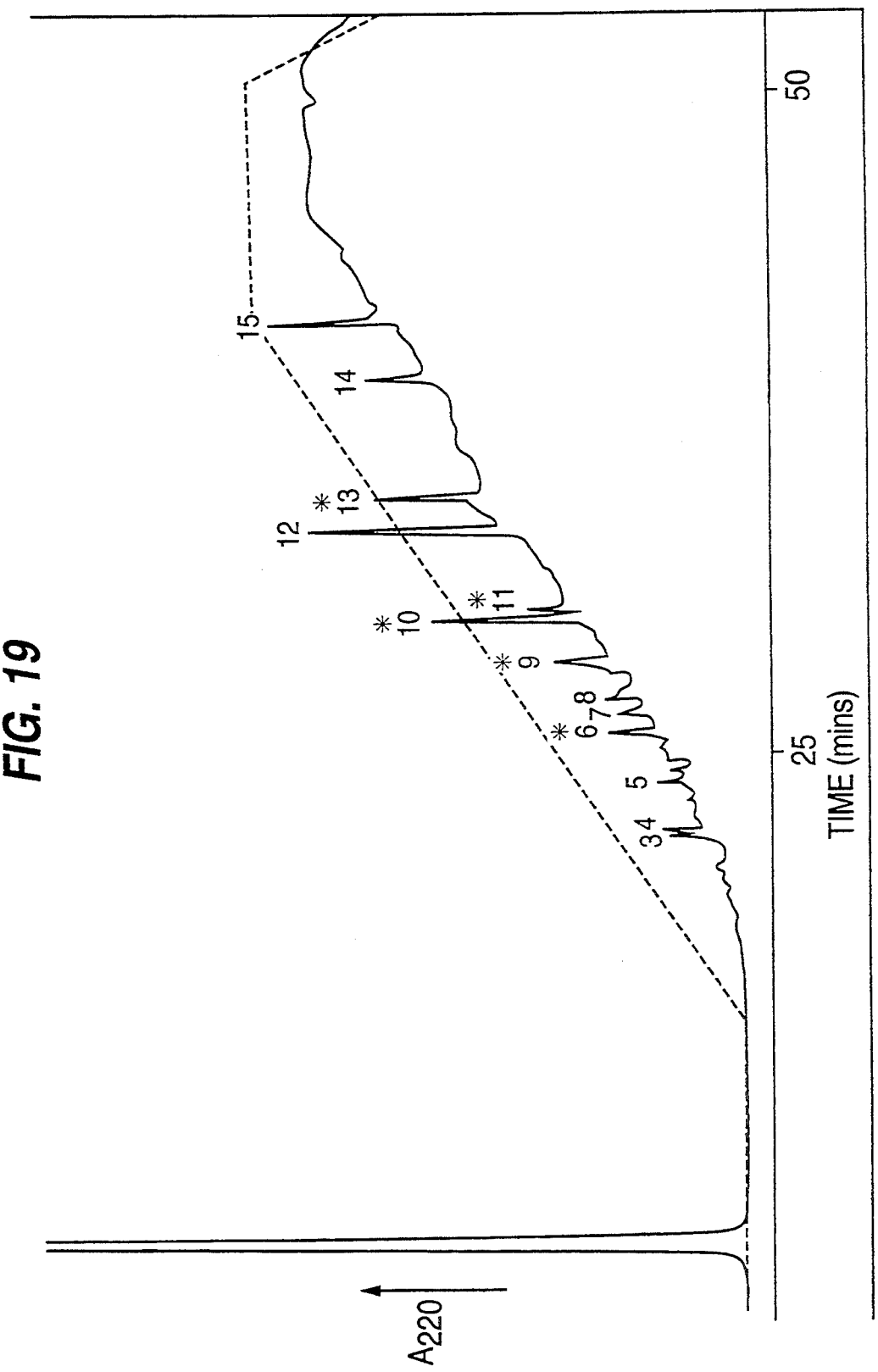

FIG. 19 shows the elution profile of peptides of minactivin eluted form a Synchropak RP-P (C-8) column high pressure liquid chromatography run.

Figure 20:
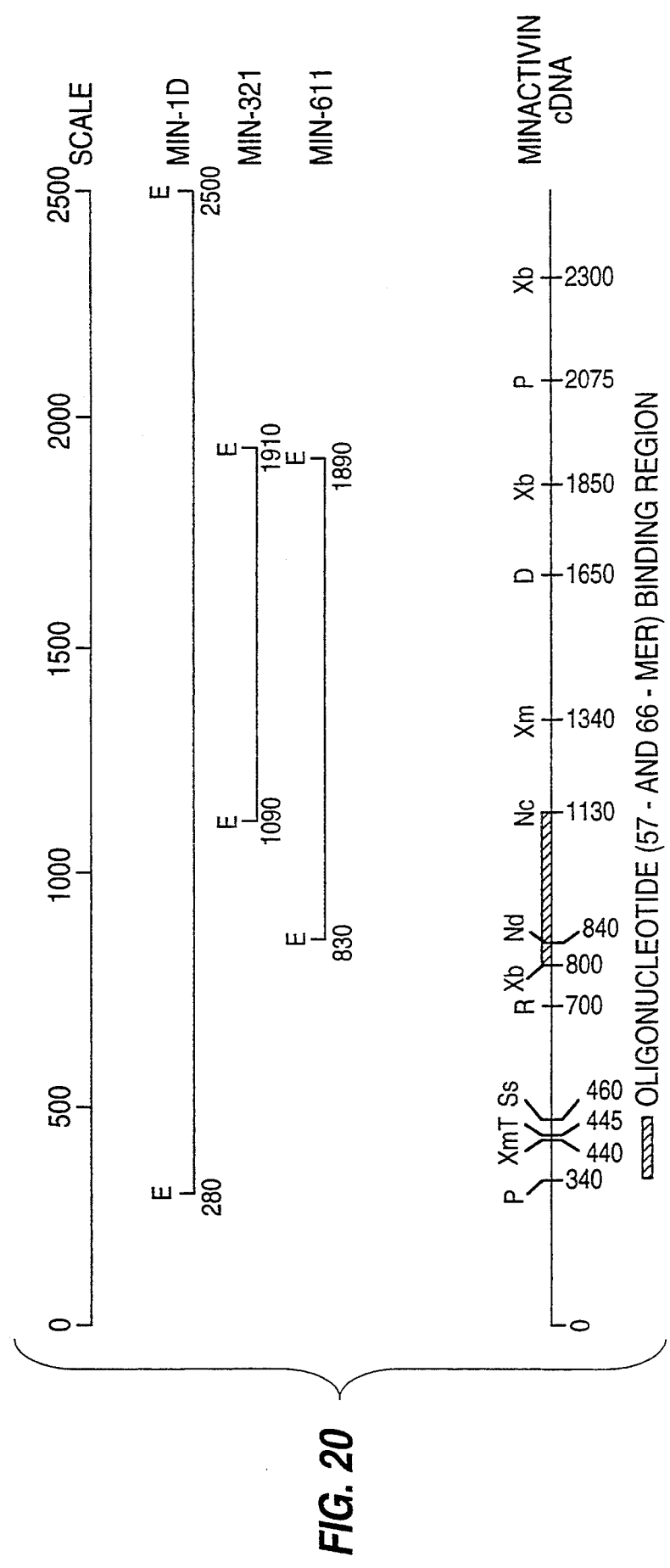

FIG. 20 depicts the endonuclease restriction map and DNA sequencing strategy of the clones containing segments of the minactivin gene.

Figure 21:
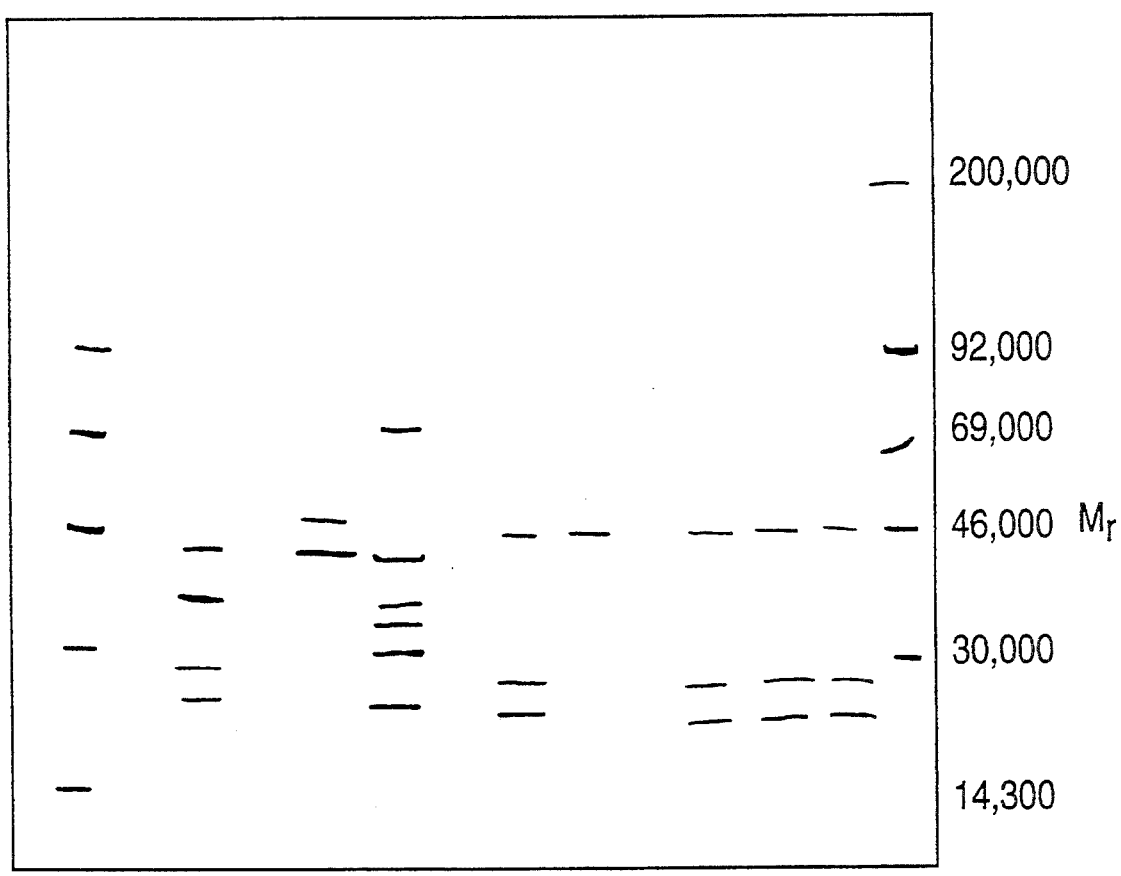

FIG. 21 shows hybrid select translation of minactivin mRNA.

Figure 22:
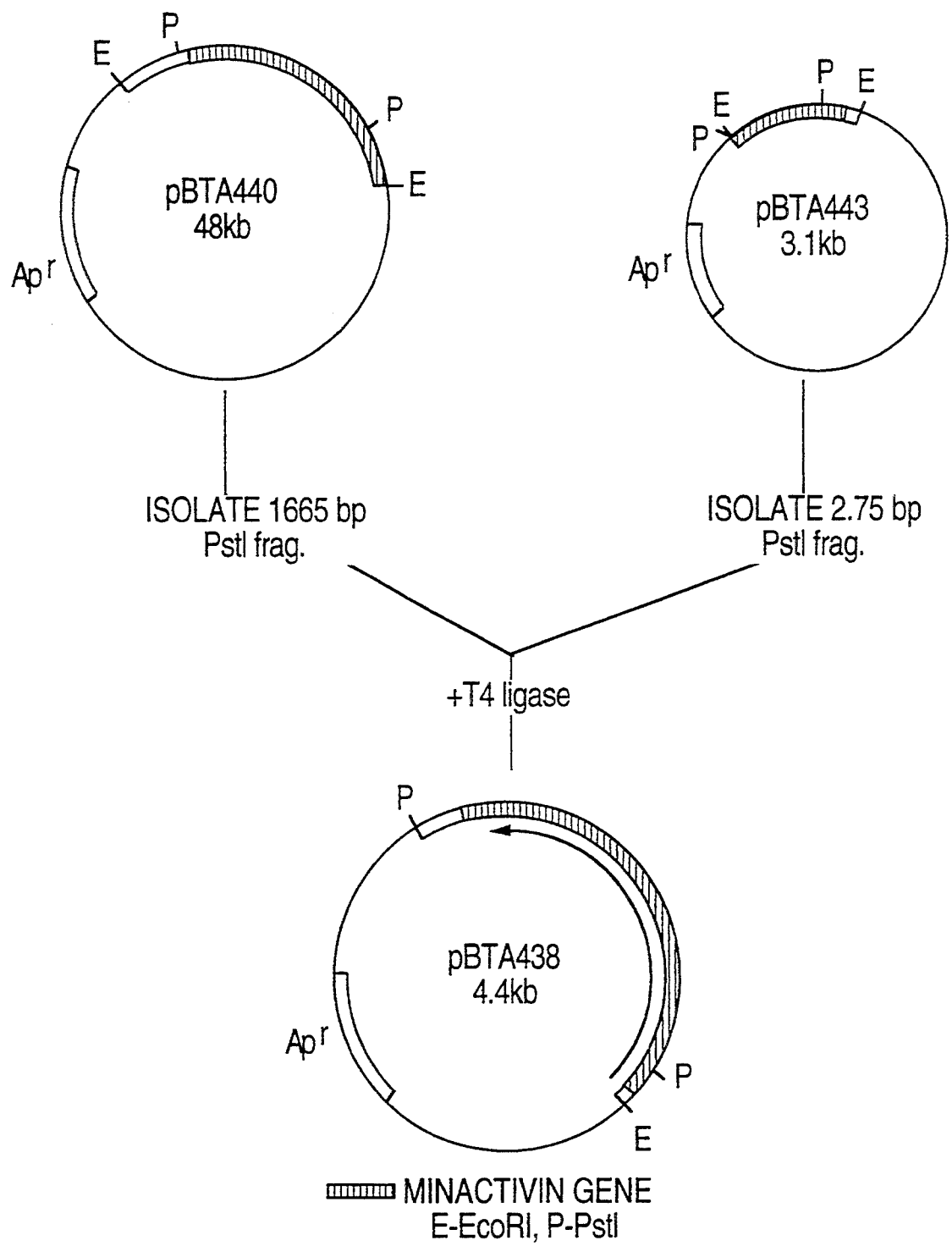

FIG. 22 shows the construction of the plasmid pBTA438 containing the contiguous minactivin gene.

Figure 23B:
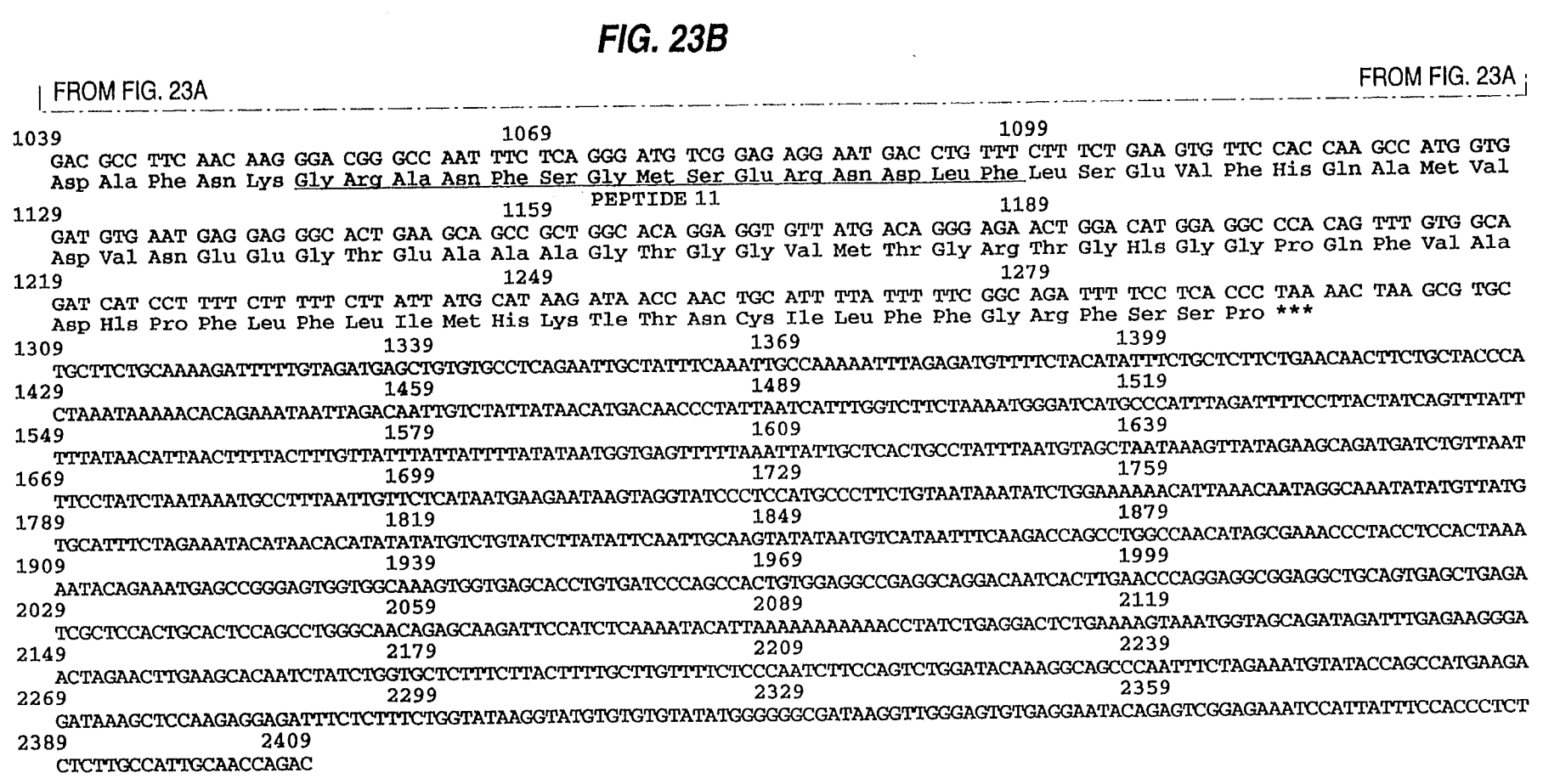

FIG. 23 shows the complete cDNA (SEQ. ID NO:18) of the minactivin gene and the deduced amino acid sequence (SEQ. ID NO:14) of the minactivin protein. The 5 peptides (set forth in SEQ. ID. Nos. 1, 2, 3, 4, and 5, respectively) obtained from the amino acid sequence analysis are underlined.

Figure 24:
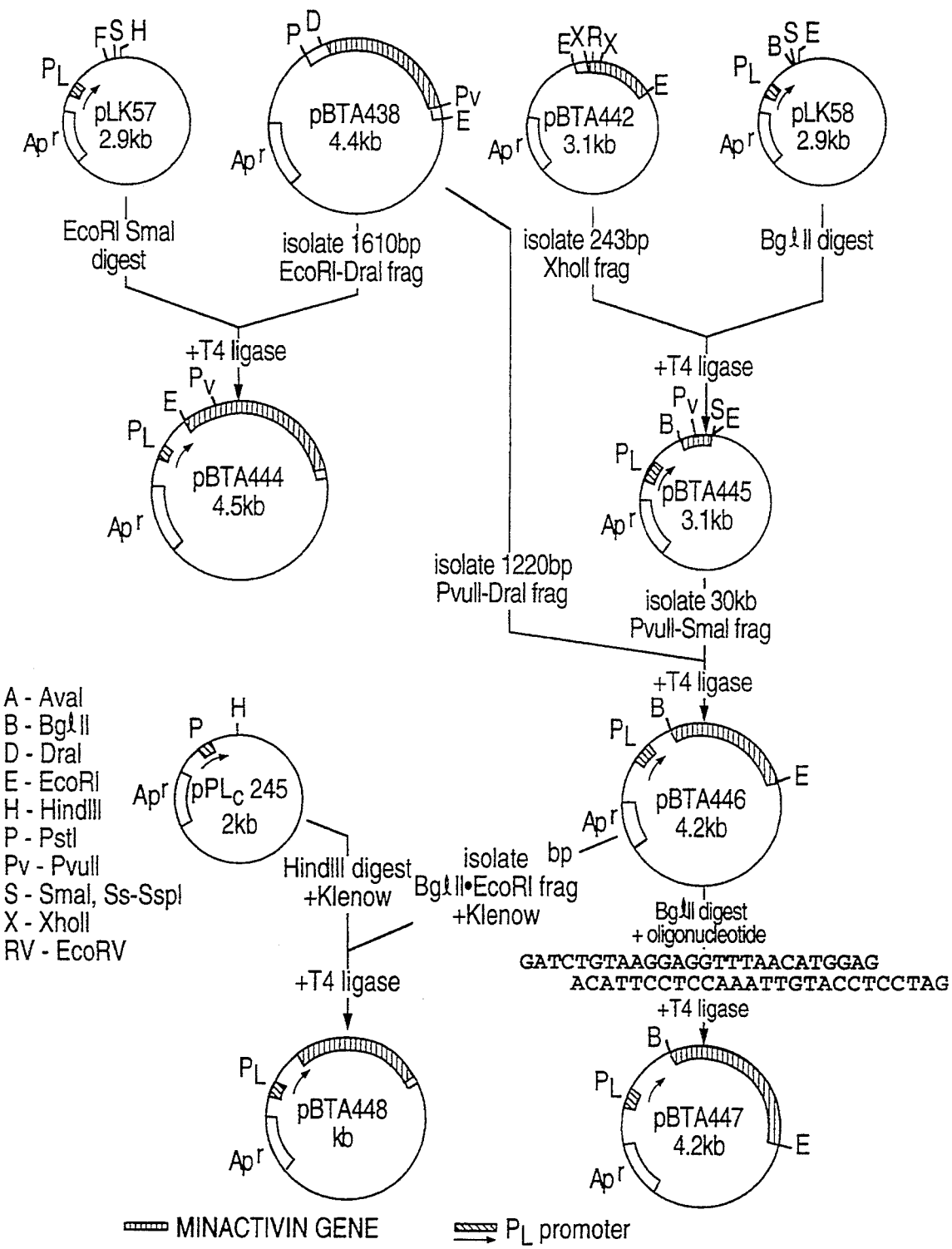

FIG. 24 shows the construction of minactivin expression vectors pBTA444 and pBTA447.

Figure 25:
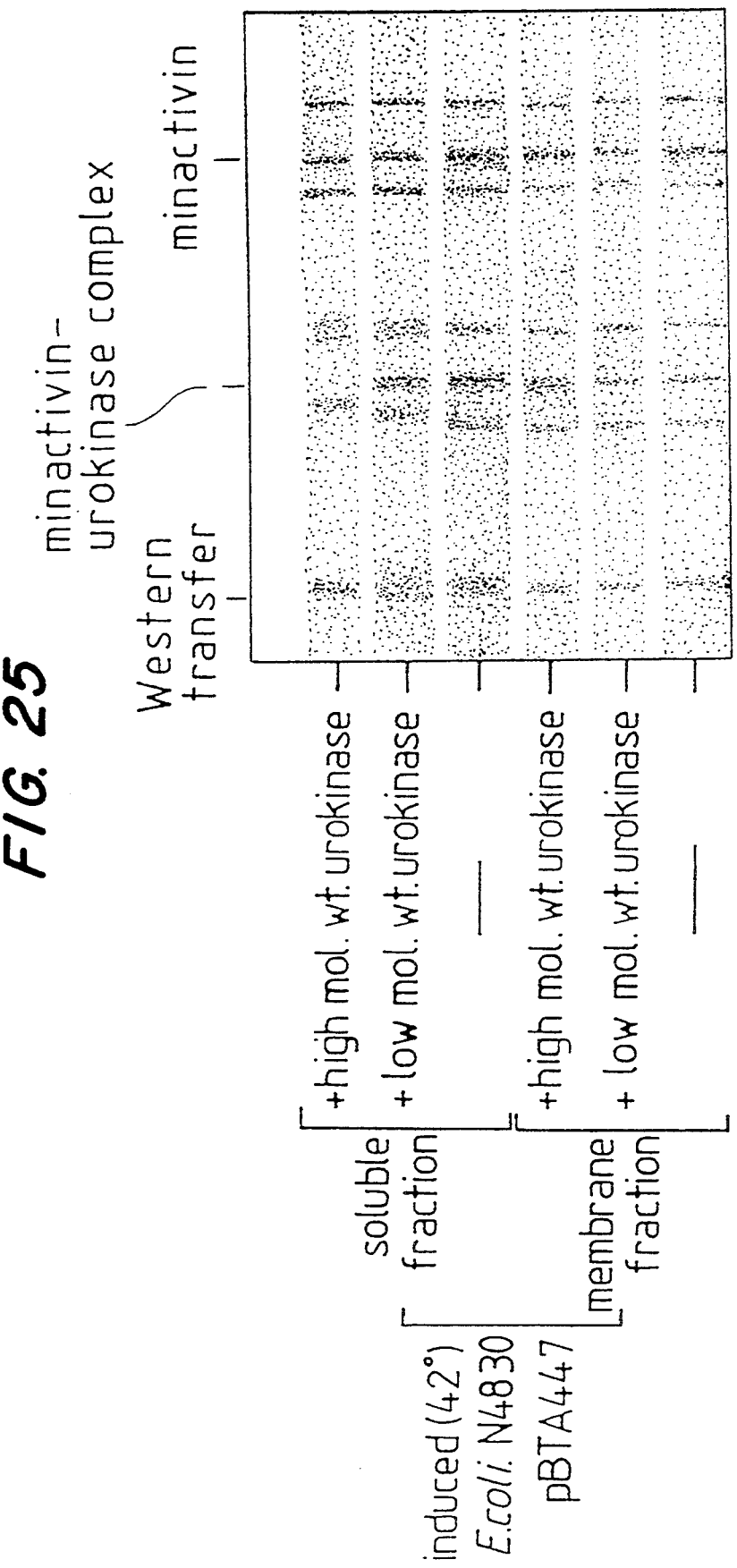

FIG. 25 shows the SDS polyacrylamide gel electrophoresis, Western analysis and $S^{35}$ pulse labelled protein analysis of minactivin expressed from pBTA444, and pBTA447.

Figure 26A:
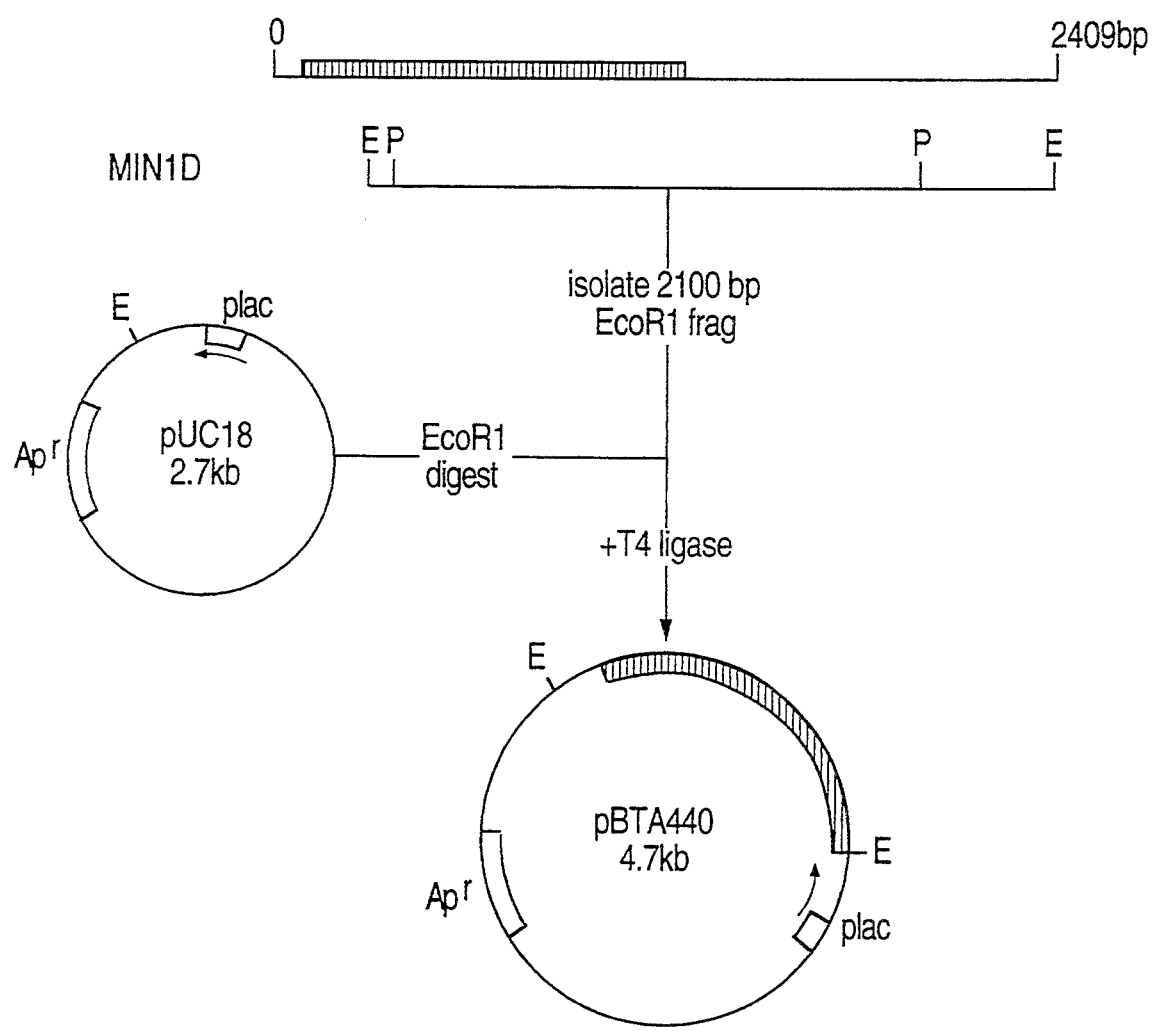

FIG. 26A and B show the construction of hybrid protein expression vectors a)pBTA440 and b)pBTA586.

Figure 27:
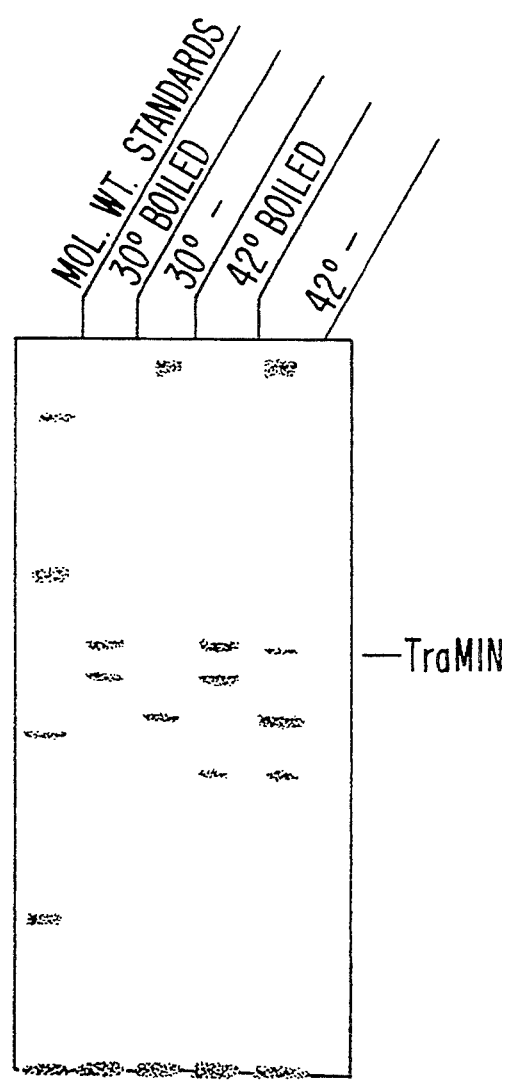

FIG. 27 shows the SDS polyacrylamide gel electrophoresis Western analysis and $S^{35}$ pulsed labelled protein analysis of hybrid minactivin proteins expressed from pBTA440 and pBTA586.

Figure 28:
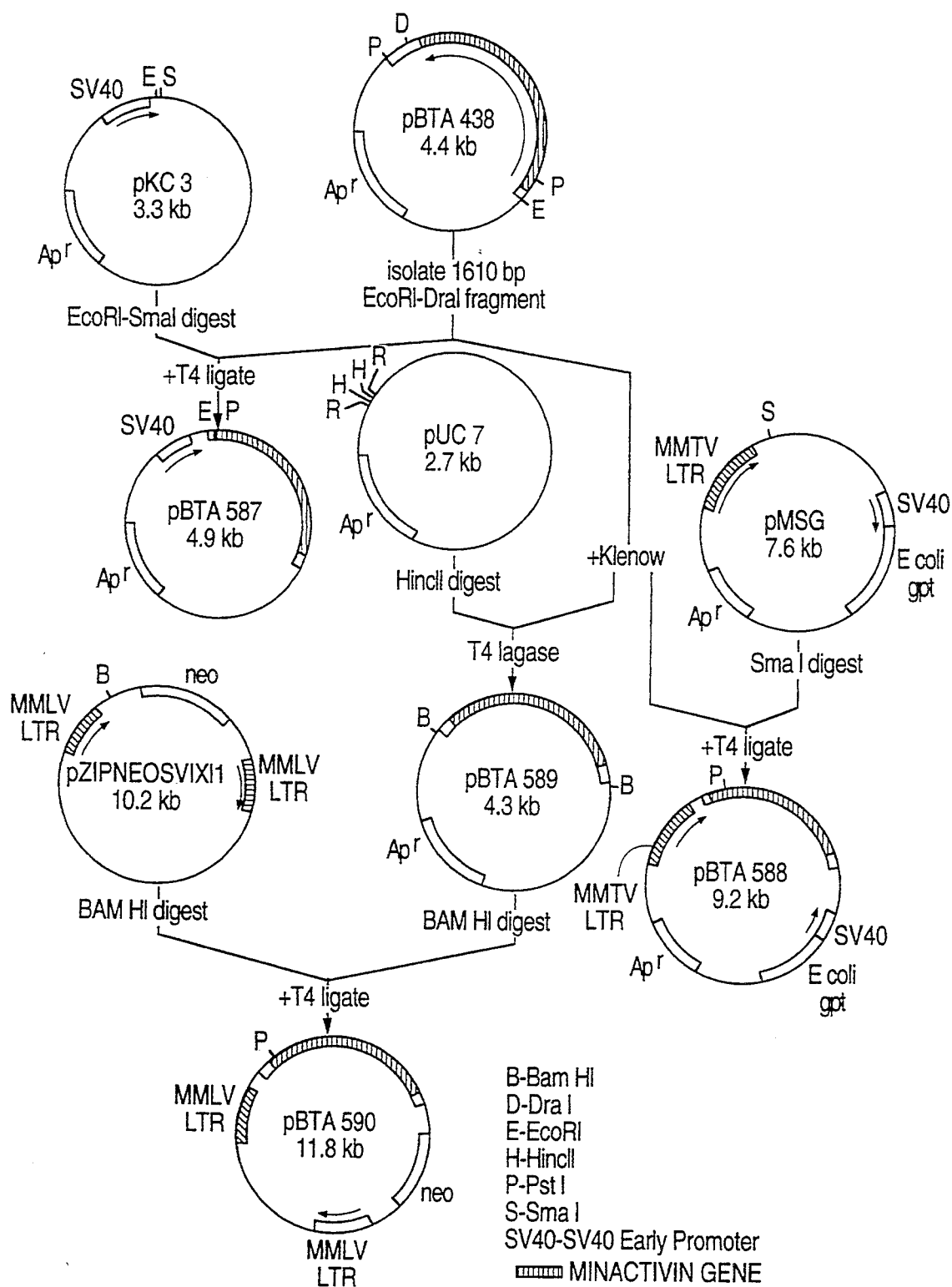

FIG. 28 shows the construction of mammalian cloning vectors pBTA587, pBTA588 and pBTA590 containing the minactivin gene.

Figure 29:
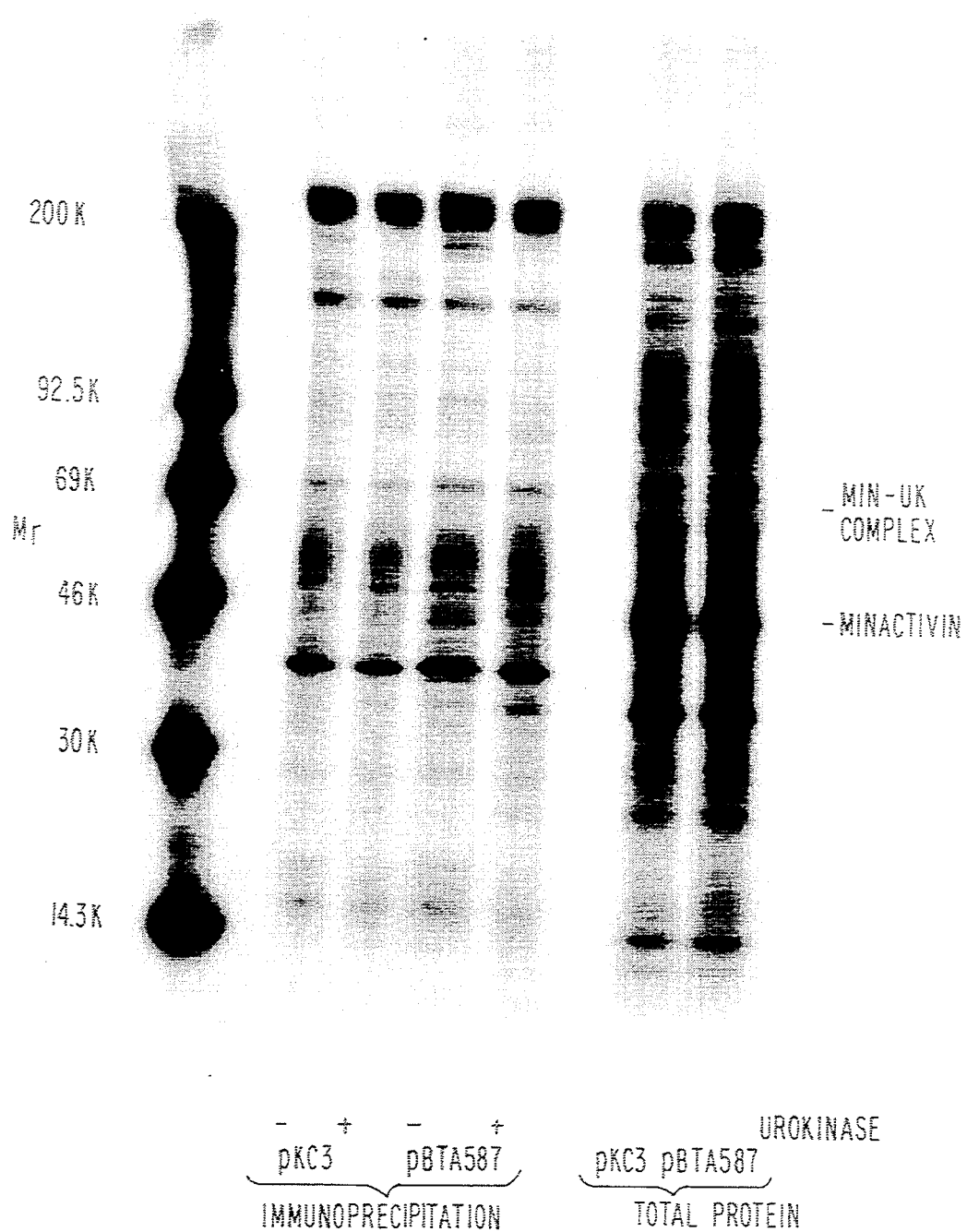

FIG. 29 is an autoradiograph showing expression of minactivin in mammalian cells following immunoprecipitation in the presence and absence of urokinase.

BEST MODE OF CARRYING OUT THE INVENTION

Induction of U937 cell line for enhanced minactivin synthesis

Figure 1:
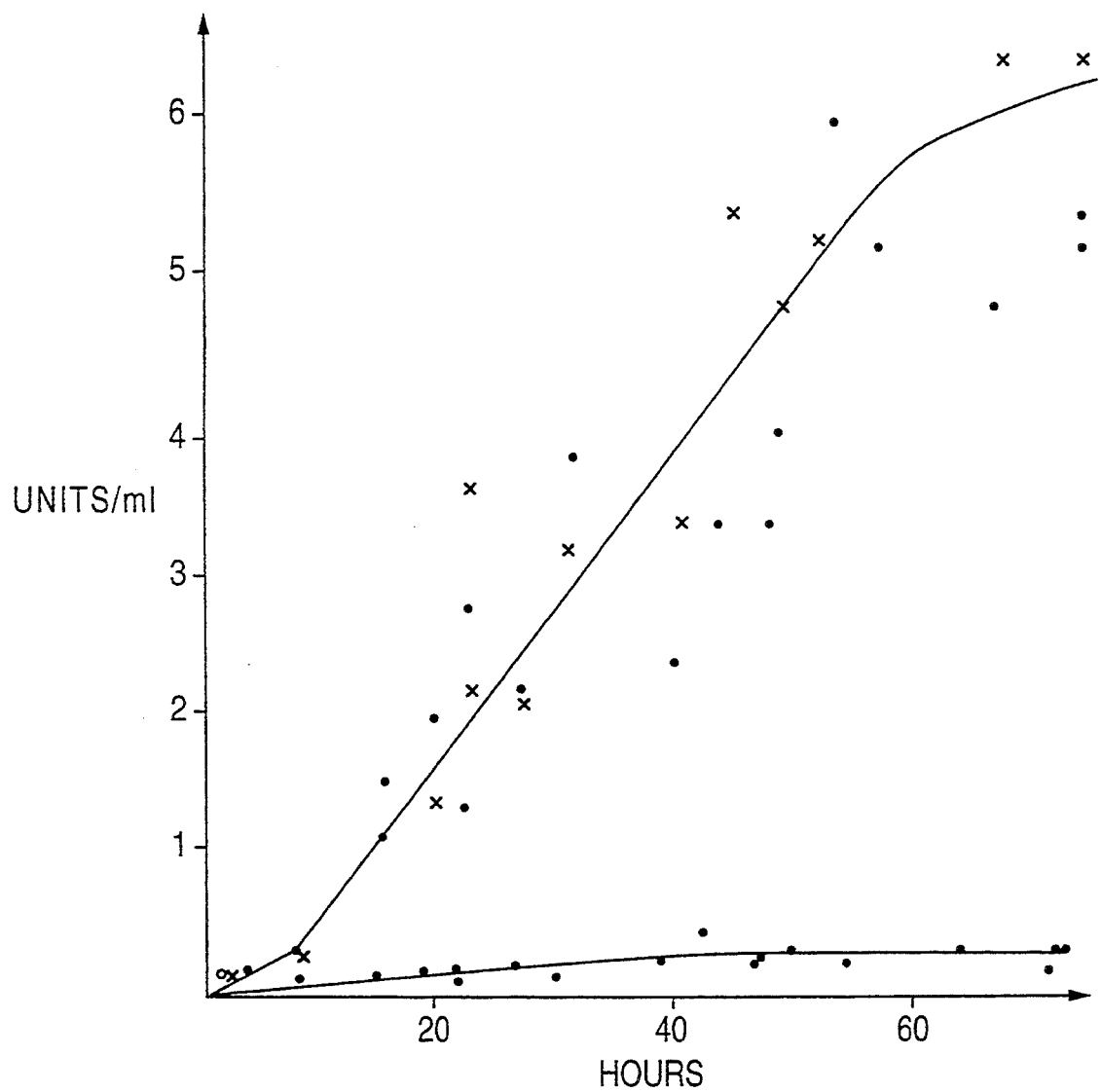
FIG. 1 is a plot of minactivin activity illustrating the effect of PMA on minactivin secretion.

Minactivin has been found to be produced by induced human monocytes, certain macrophages, and transformed cells of monocytic lineage (refer to international patent application WO86/01212). The transformed cell line U937 (ATCC CRL 1593) was found to produce minactivin constitutively in the presence of dexamethasone. The level of minactivin secreted by these cells under serum free conditions was found to be only about 0.06% of the total protein secreted by these cells. It was found that this level could be enhanced by approximately an order of magnitude to 0.4% with the addition of 4-phorbol-12-myristate-13-acetate (PMA). The effect of PMA on minactivin secretion with time followed biphasic course with an initial lag per of 6 hours, followed by a linear increase in minactivin activity up to 60 hours (FIG. 1). No differences were observed by increasing the PMA concentration from 10 ng/ml to 30 ng/ml. Furthermore, it was determined that the phorbol esters were tightly associated with the cells, as radioloabelled PMA could be detected only in small amounts (less than 10%) in the culture supernatants ever after 17 hours.

The following examples illustrate preferred embodiments of the invention. They should not be construed as limiting on the scope of the invention. Unless otherwise stated, all parts and percentages are by weight.

EXAMPLE 1

Minactivin activity was measured by a modification of the method of Coleman and Green N.Y. Acad. Sci. 370, 617 (1981), as described by Stephens et al Eur. J.

Biochem. 136, 517–522 (1983), in which the inhibitory activity of minactivin was determined by quantifying the loss of urokinase activity in the colorimetric assay using a urokinase reference standard (Calbiochem). The minactivin samples were preincubated with 4 mPU urokinase for 90 minutes at 23° C. before the addition of plasminogen. One unit of minactivin activity was defined as that amount which inhibited 1 Plough wait of urokinase. Human urokinase was purchased from Calbiochem Behring Corp. La Jolla, Ca. Plasminogen was purified from fresh human plasma by lysine-sepharose (Pharmacia) affinity chromatography (Unkeless, J. C. et al. (1974), J. Biol. Chem. 249, 4295–4305).

The protein concentration was determined according to the method of Bradford, M. M., Anat. Biochem. 72, 248–254 (1976) using bovine serum albumin as the standard. Specific activity is defined as the minactivin activity as measured by colorimetric assay divided by the protein concentration.

Proteins were separated by SDS-polyacrylamide gel electrophoresis using 11% Laemmli gels (Laemmli, U. K., nature 227, 680–685, 1970) or on SDS-urea-gradient polyacrylamide gels using a modified Laemmli buffer system as described by Mattick, J. S. et al Eur. J. Biochem. 114, 643–651 (1981). Western (Transfer) blotting was performed by electrophoretic transfer to nitrocellulose as described previously (Towbin, H. et al., Pro. Natl. Acad. Sci. USA, 76, 4350–4354 and Johnson, D. A. et al, Gene Anal. Tech. 1, 3–8 1984).

Cell Culture

The human macrophage cell line, U937, was cultured in RPMI 1640 containing 10% foetal calf serum and 1 micromolar dexamethasone, either in T175 culture flasks or in a 10 liter Braun fermenter. The cells were maintained at densities of 1– $3 \times 10^6$ cells/ml. Although minactivin was secreted by the cells during this growth phase, the cells were transferred to serum-free medium to obtain supernatants for minactivin purification. The cells were pelleted by low speed centrifugation, washed by resuspension in phosphate buffered saline and recentrifugation and then resuspended in serum free RPMI 1640 containing 1 micromolar dexamethasone, and cultured for a period of three days. The level of minactivin secreted by these cells under serum free conditions could be enhanced by approximately an order of magnitude to 0.4% with the addition of PMA.

The cells were then harvested and the supernatants used in the purification scheme which follows.

EXAMPLE 2

Purification of Homogeneous Minactivin a) Concentration of Serum Free Minactivin Supernatants Typically, 4 to 5 liter of culture supernatant was concentrated 10-fold using an Amicon DC2 Hollow Fiber dialysis/Concentration unit equipped with a 30,000 MW cut-off cartridge. The concentrate was then dialysed using the DC-2 Hollow fibre unit by repeated concentration and dilution using at least an equal volume of 50 mM glycine pH 7.8 for 3 to 6 hours at room temperature, to remove all traces of dye.

b) Centrifugation of Minactivin Concentrate

The dialysed concentrate was centrifuged in a JA10 rotor at 8000 rpm for 30 min at 4° C. to pellet residual cell debris and protein that may have precipitated during dialysis. The clarified supernatant is then aliquoted and frozen at −20° C. until required for subsequent purification.

c) Phenyl-Sepharose Chromatography using a Step pH Elution

Minactivin was further purified from ten-times concentrated culture supernatant obtained from cells cultured in the absence of PMA by step pH elution using phenyl-sepharose as follows.

Figure 14:
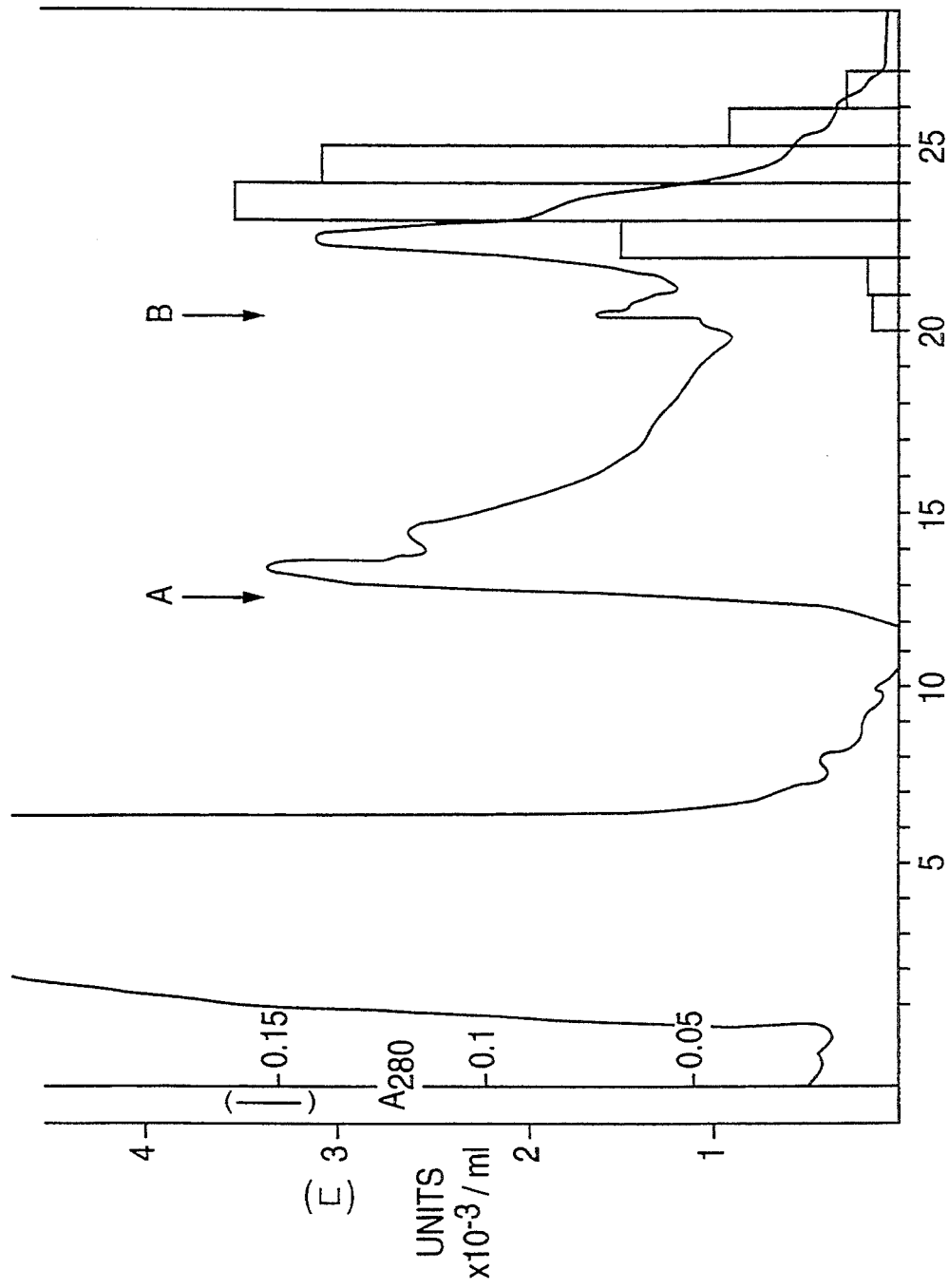
FIG. 14 shows the elution profile of minactivin activity and protein from the step pH elution of the phenyl-sepharose column.

The ionic strength of the supernatant (200 ml; 12000 units; specific activity 102 units/mg) was adjusted to 2M by the addition of solid NaCl and the pH adjusted to 5.5 with citric acid. This solution was applied to a phenyl-sepharose column (4.4 cm×5.0 cm) equilibrated in 50 mM Na citrate, pH5.5, 2M NaCl and 1 mM EDTA and eluted with the same buffer until the baseline absorbance at 280 nm (A280) returned to baseline. The column was then eluted with 50 mM sodium citrate, pH5.5 containing 0.5M NaCl and 1 mM EDTA and again the A280 monitored until the absorbance returned to baseline. The minactivin was then eluted from the column with 50 mM glycine, ph9.0. FIG. 14 shows the elution profile.

The recovery of minactivin by this method was 9553 units which represents 80% of the units applied to the column. The material of highest specific activity was pooled (6700 units: specific activity 1343 units/mg) and concentrated to 3 ml on an Amicon YM10 membrane.

d) Sephacryl S-200 Gel Permeation Chromatography

Figure 8:
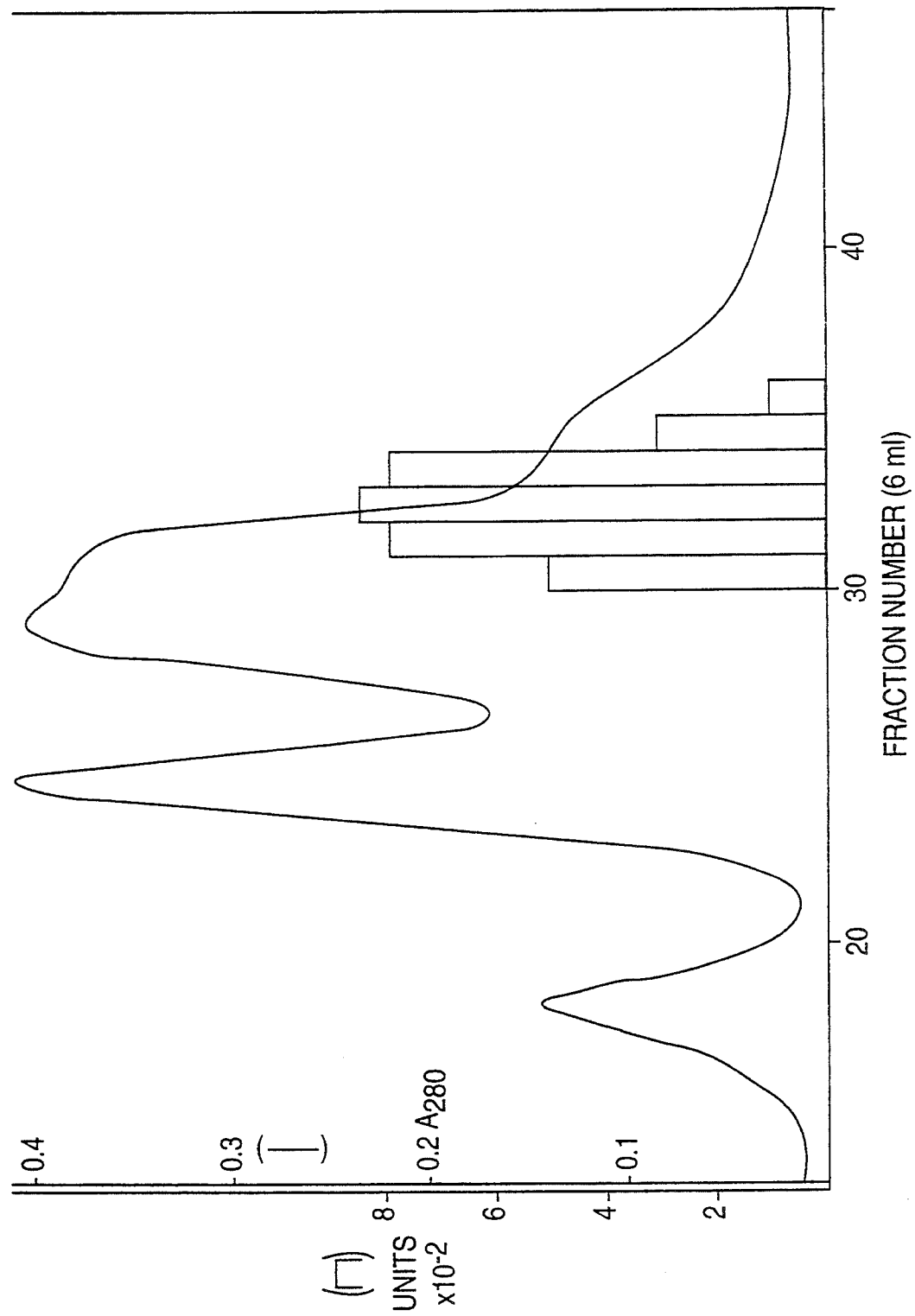
FIG. 8 is a Sephacryl S-200 chromatograph showing elution of enriched minactivin activity relative to total protein elution.

The pooled, concentrated minactivin was applied to a 2.2 cm×78 cm column of Sephacryl S-200 equilibrated with 0.1M sodium borate, ph9.0. Fractions of 5.0 ml were collected at a flow rate of 0.46 ml/min. FIG. 8 shows that minactivin was eluted at the tailing edge of the major protein peak. The fractions containing minactivin activity were pooled (4480 units; specific activity 1355 units/mg) and concentrated to 3 ml using a YM10 membrane. Calibration of this column with known $M_r$ standards indicated that minactivin had an $M_r$ of 45–48 kD.

e) Isoelectric Focussing

The concentrated minactivin solution was applied to a preparative flat bed gel of Ultrodex containing Ampholines in the pH range 4.5–6.0 and electrofocussed for 23 hrs at 10° C. on an LKB Multiphor isoelectric focussing apparatus. Following completion of the run, 30 zones across the length of the gel were scraped out and the protein eluted from each with 10 ml of 1M glycine containing 1 mM EDTA, pH9.0. Aliquots of each fraction were assayed for minactivin activity and electrophoresed on 15% SDS-polyacrylamide gels to locate protein. FIG. 15 illustrates that a significant amount of protein has been removed from the fractions containing the minactivin activity. Under these conditions minactivin focusses between pH5 and pH5.2 and within this region of the gel 15% of the total activity applied to the gel was recovered.

In fact, in the region of the isoelectric focussing gel containing minactivin activity, only two protein bands are visible (FIG. 15). To determine which of these bands is minactivin the protein on an equivalent polyacrylamide gel was transferred onto nitrocellulose and probed with antibodies made in goat to placental inhibitor. Due to similar biological properties it was considered likely that the two proteins would be immunologically related. As shown in FIG. 16 the protein band of $M_r=45–48$ kD specifically cross reacts with the anti-placental inhibitor antibodies suggesting that this protein band is minactivin. Furthermore, this observation is consistent with the $M_r$ of 45–48 kD determined for native minactivin on gel permeation chromatography.

f) High Pressure Liquid Chromatography

The fractions from the isoelectric focussing above which contained minactivin activity were concentrated 10-fold on an Amicon YM10 ultrafiltration membrane and further fractionated on a Vydac C-4 reverse phase column using a Waters high pressure liquid chromatograph. The proteins were eluted from the reverse phase column using a gradient of acetonitrile in 0.1% TFA as shown in FIG. 17. Each of the absorbance peaks was examined by SDS-PAGE and peak 5 was found to contain pure minactivin (FIG. 18).

EXAMPLE 2a (a) Gel Filtration

Call free supernatants were processed through steps (a) and (b) as described in Purification Example 2 of WO86/01212, and then through Phenyl-Sepharose using a step pH elution as described in Purification Example 1 of WO86/01212. The fractions containing minactivin activity were pooled, concentrated by precipitation with 85% saturated ammonium sulphate and applied to a 2.2 cm×80 cm column of Sephacryl S-200 equilibrated in 0.1M sodium borate, pH9.0. Fractions of 3.5 ml were collected at a flow rate of 0.46 ml/min. FIG. 8 shows that minactivin was eluted as the tailing edge of the major protein peak and had a peak specific activity of 2206 Units/mg representing an overall increase in specific activity of 31 fold. Under these conditions the minactivin behaves as a molecule with a Stokes radius similar to ovalbumin, suggesting a molecular size of $45-49 \times 10^3$ daltons.

(b) Phenyl-Boronate Agarose Chromatography

Cell free supernatants were processed through steps (a) and (b) as described in Purification Example 2 of WO86/01212. one ml of the supernatant was made to 10 mM in $MgCl_2$ and the pH then adjusted to pH8.5 with sodium hydroxide. This solution was applied to a column of phenyl-boronate agarose −30 (PBA 30) (0.8 cm×2.5 cm) equilibrated in 50 mM glycine, pH8.5 containing 10 mM $MgCl_2$ at 4° C. The column was then washed with 9 ml of the above buffer and then serially as follows:

a) 10 ml of 50 mM glycine, pH8.5 containing 10 mM EDTA b) 10 ml of 50 mM glycine, pH8.5 containing 100 mM sorbitol c) 10 ml of 100 mM Tris-HCl, pH8.5 d) 10 ml of 50 mM sodium acetate, pH 5.0.

Figure 9:
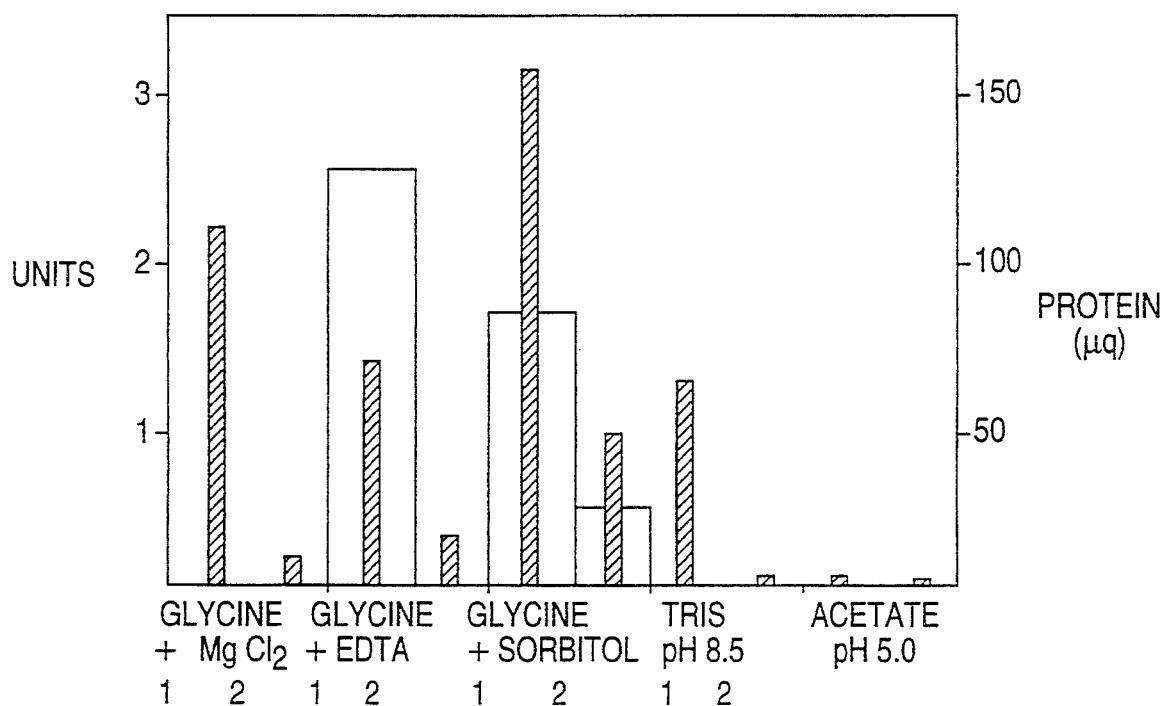
FIG. 9 is a plot showing differential elution of minactivin activity from phenyl-boronate agarose under varied elution conditions.

Fractions of 5 ml were collected and dialysed against 50 mM glycine, pH7.8 overnight at 4° C. prior to minactivin activity and protein determinations. The results shown in FIG. 9 illustrate that two distinct peaks of activity elute from the column under different conditions. The first peak, eluted with EDTA, contains 35% of the total activity loaded onto the column with an increase in specific activity of 14 fold. The second peak represents 32% of the initial activity with a 4.4 fold increase in specific activity.

(c) Chromofocussing

Figure 10:
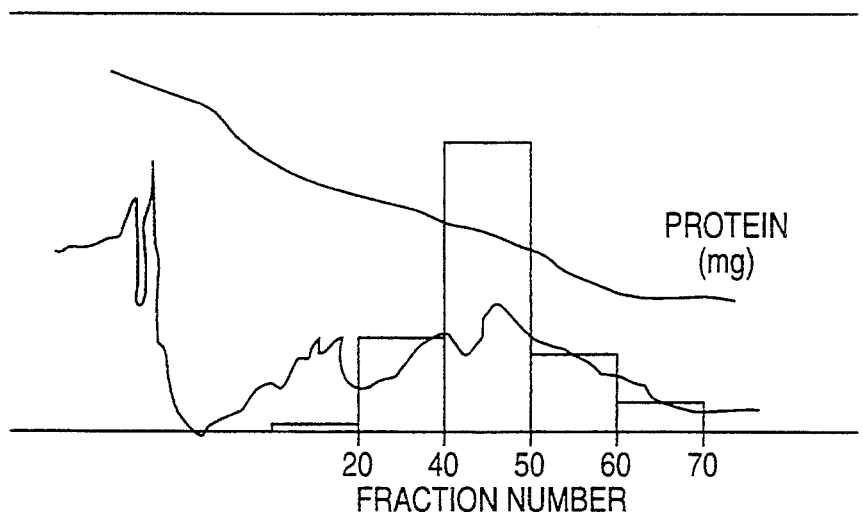
FIG. 10 is a chromatograph showing elution of minactivin activity relative total protein eluted from a chromofocussing column as a function of pH of elution.

Cell free supernatants were processed through steps (a) and (b) as described in Purification Example 2 of WO86/01212. Four ml of this supernatant was dialysed against 25 mM imidazole-HCl buffer, pH7.4 overnight at 4° C. and then applied to a PBE 94 chromofocussing column (1 cm×27 cm) equilibrated in the above buffer. A linear pH gradient was then established by applying 200 ml of polybuffer pH 4.0 and 4 ml fractions were collected into 4 ml aliquots of 1M Tric.HCl, pH7.5. Every 10 fractions were pooled, concentrated and washed on a centricon 30 and assayed for minactivin activity and protein concentration. FIG. 10 shows that the majority of the activity eluted near pH5. The overall recovery of activity was 87% and there was a 2 fold increase in specific activity.

(d) Isoelectric Focussing

Figure 11:
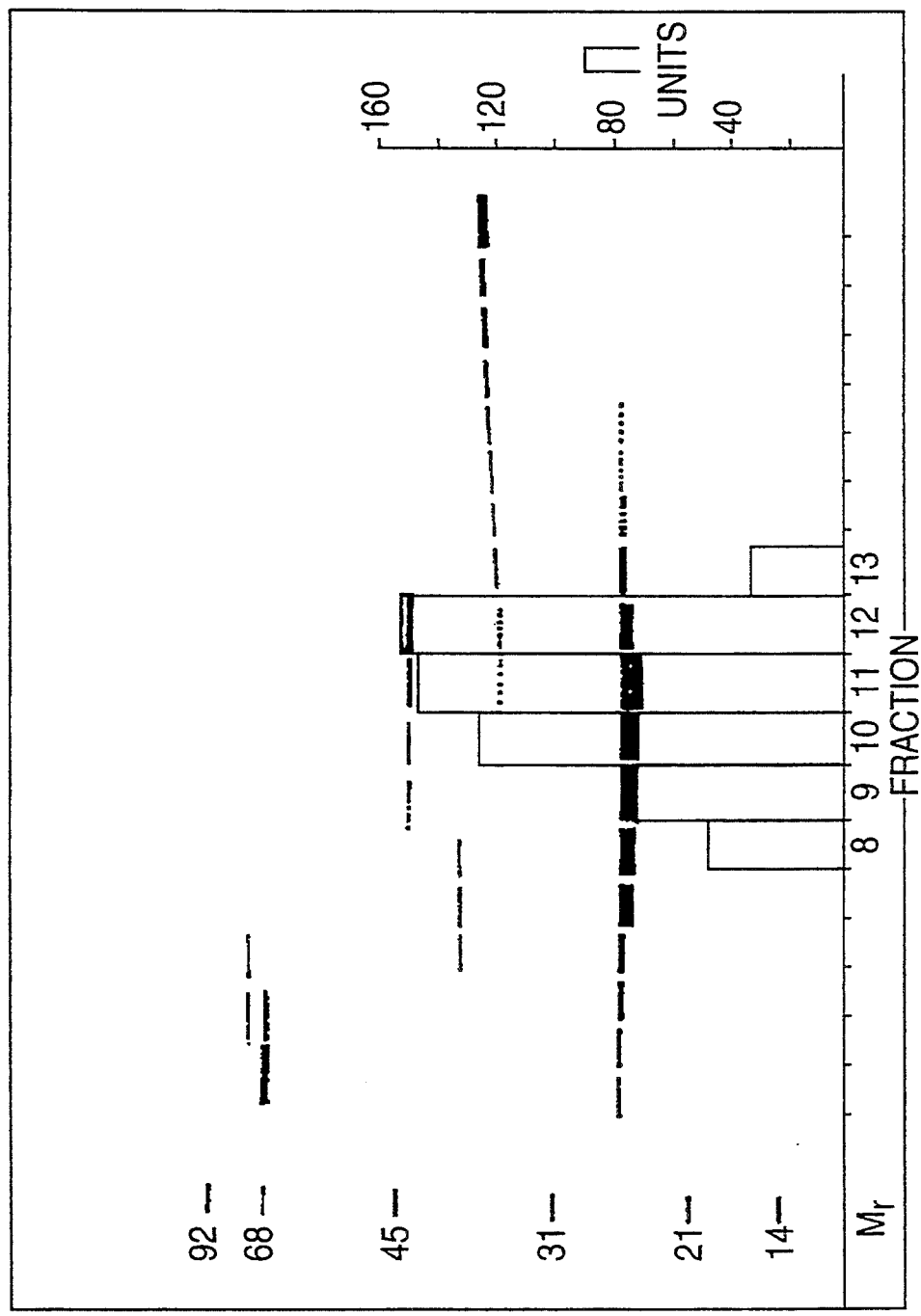
FIG. 11 is a superimposition showing minactivin activity over a gel of the protein fractions isolated from an isoelectrofocussing gel to demonstrate protein content versus minactivin activity.

Cell free supernatants were processed through steps (a) and (b) as described in Purification Example 2 of WO86/01212, and then through phenyl Sepharose using a step pH elution as described in Purification Example 1 of WO86/01212. The fractions containing minactivin activity were pooled, concentrates by precipitation with 85% saturated ammonium sulphate and dialysed overnight against 50 mM glycine pH9.0. This solution was applied to a preparative flat bed gel of Ultrodex containing Ampholines in the pH range 4.5–6.0 and electrofocussed for 23 hrs at 10° C. on a LKB Multiphor isoelectric focussing apparatus. Following completion of the run, 30 zones across the length of the gel were scraped out and the protein eluted from each with 10 ml of 1M glycine containing 1 mM EDTA, pH9.0. Aliquots of each fraction were assayed for minactivin activity and electrophoresed on 15% SDS-polyacrylamide gels to locate protein. FIG. 11 illustrates that a significant amount of protein has been removed from the fractions containing the minactivin activity. Under these conditions minactivin focusses between pH5 and pH5.2 and within this region of the gel 39% of the total activity applied to the gel was recovered.

(e) Immunoaffinity Chromatography

Figure 12A:
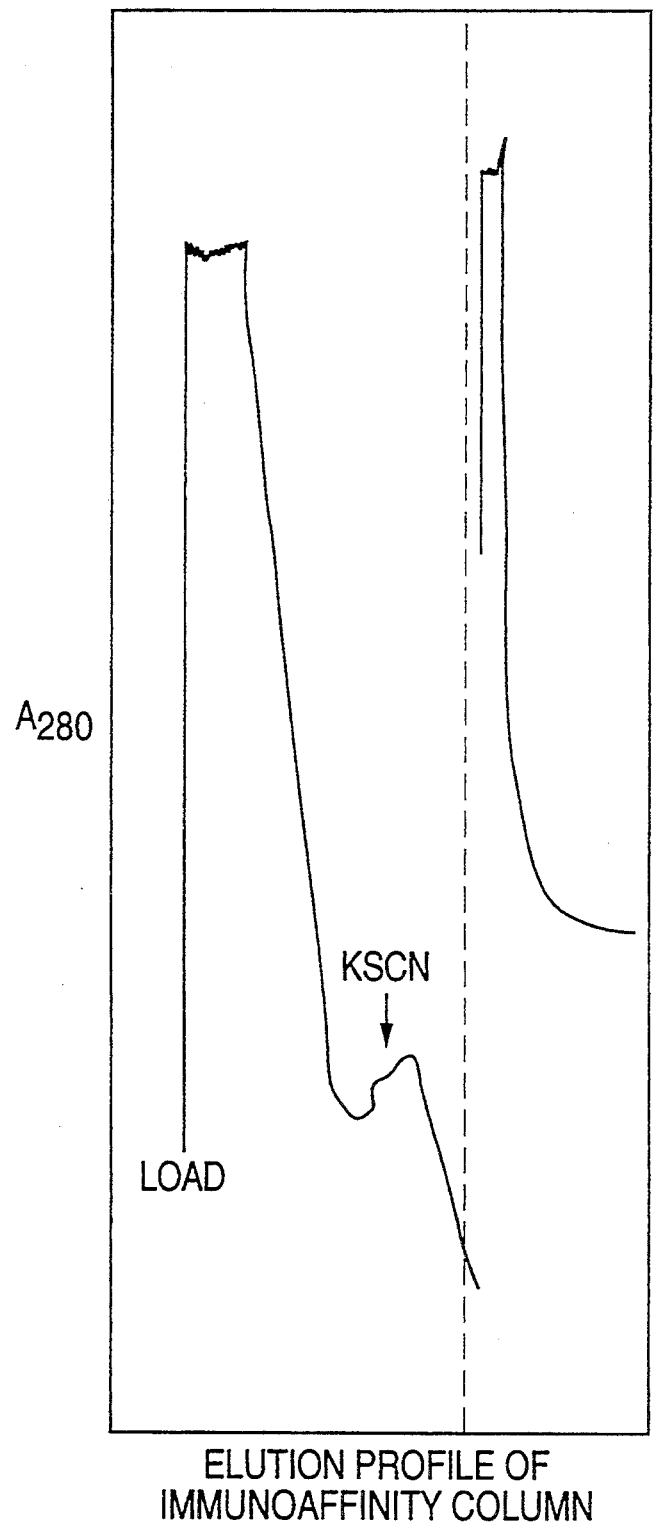
FIG. 12a is a elution profile of an immunoaffinity column showing elution of minactivin activity.
Figure 12C:
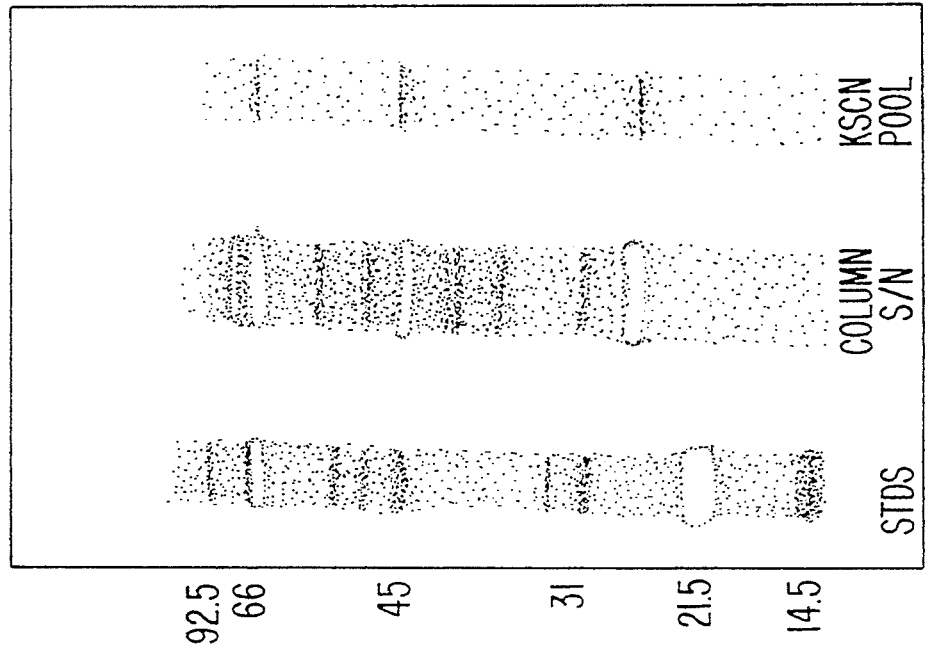
FIGS. 12b–12c are a representation of an SDS-PAGE gel of minactivin eluted from the immunoaffinity column and a Western blot of this gel.
Figure 12B:
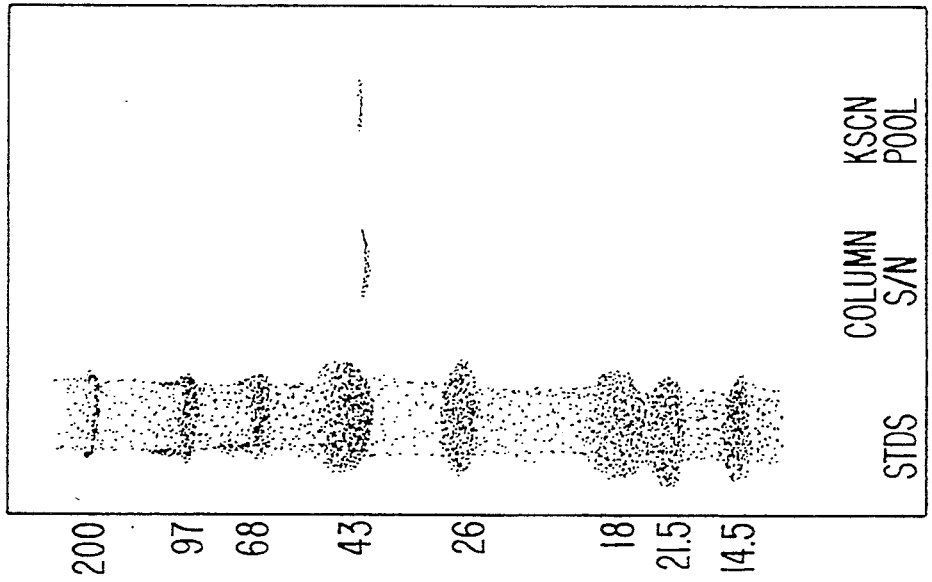
Figure 13:
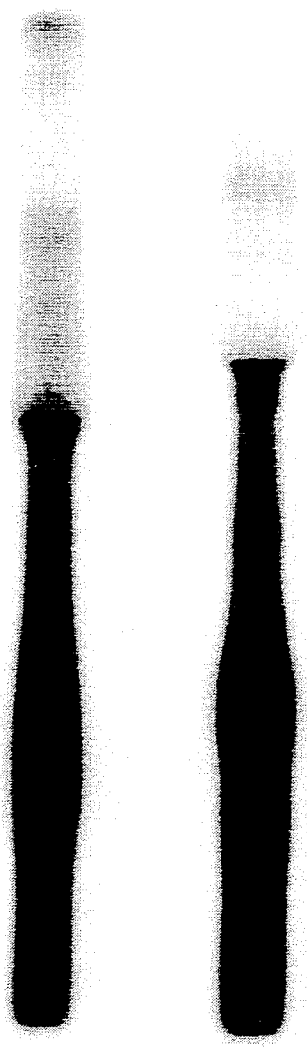
FIG. 13 is an autoradiograph of $I^{125}$-labelled urokinase on SDS-PAGE showing high and low molecular weight forms and dissociation of high molecular weight form under reducing conditions.

Cell free supernatants were processed as through Purification Example 1. A 4.6 ml aliquot of this minactivin preparation (2300 Units, 2.25 mg, specific activity 1020U/mg) was made 0.05M in sodium phosphate, 0.5 in NaCl, 0.01% in TritonX-100, 0.1% in sodium azide, 1 mM in EDTA and the pH adjusted to 7.5 . This solution was diluted to 15 ml with the above buffer and added to 15 ml of Sepharose 4B to which 10 mg of anti-placental inhibitor antibody had been chemically coupled using the 1,1'-carbonyl-diimidazole method of Bethell, G. S. et al J. of Biol. Chem. 254 (8) 2572–2574 (1979). The slurry was shaken overnight at 4° C. and then poured into 2.5 cm×3.1 cm column. Unbound protein was drained from the column and the column washed with the above buffer until the absorbance at 280 nm returned to baseline. The column was then eluted with 3M KSCN containing 10 mM tris. HCl, pH8.0. The elution profile is shown in FIG. 12. The fractions eluted by the KSCN were concentrated 8.5 fold on a Centricon 10, washed with 40 mM glycine, pH 7.8 and analysed for minactivin activity and by SDS-PAGE. The majority of the minactivin activity did not bind to the antibody column. However, a small amount of minactivin activity (8.5 units) is bound specifically and is eluted with 3M KSCN. This indicates that under these conditions the antibody column has been overloaded with minactivin. Furthermore, minactivin loses over 90% of its activity in the presence of KSCN over a comparable period of time suggesting that the low recovery of minactivin activity may be due in inactivation of the molecules in KSCN. The SDS-PAGE results show that the vast majority of the protein elutes unretarded from the column. The KSCN eluate however contains a major protein band of molecular weight ca 45,000, similar to the molecular size of minactivin on gel filtration (see Example 2A(a) (FIG. 12a). Western analysis of this minactivin preparation showed a single immunologically cross reactive species migrating identically with the protein band observed following SDS-PAGE (FIGS. 12b–12c).

Under certain conditions, minactivin has been observed to have a molecular size of approximately 60–70,000 (as detailed in PCT191-85). This discrepancy may be due to altered mobility due to the degree of glycosylation of minactivin.

EXAMPLE 3

Isolation and Sequence of Peptide Fragments from Minactivin

Minactivin was purified from PMA induced U937 cells as described in Example 2 above. The minactivin (3–5 μg) was then digested with endoproteinase Lys C (0.1 μg) n 20 mM Tri-HCl, pH 8.5 containing 5M Urea in a final volume of 50 μl for 8 h at 22° C. The resultant peptides were separated by reverse phase high pressure liquid chromatography on a Synchropak RP-P (C-8) column using a gradient of acetonitrile in 0.1% TFA (FIG. 19). The peptides indicated by the asterisks were sequenced on an Applied Biosystems 470A gas phase sequencer and the sequences are as follows (and are also set forth in SEQ. ID. NOs. 1, 2, 3, 4 and 5, respectively).

Peptide 13: AQILELPY-GDV-MFLLLP-E . . .
Peptide 11; GRANFSGMSE-NDLF . . .
Peptide 10: MAE-EVEVYIPQFKLEE-Y . . .
Peptide 6: LNIGYIEDLK
Peptide 9: IPNLLPEG-V

EXAMPLE 4

Molecular Cloning of Minactivin a) Isolation of mRNA

From FIG. 1, the optimal time of transcription for PMA induced U937 cells could be estimated to be between 15 and 25 hours. Therefore, a four liter serum-free culture of U937 cells at a cell density of $1.2 \times 10^6$ cells/ml was incubated for 19 hours in the presence of PMA, the cells harvested, and quick frozen in liquid nitrogen until further use. Non-PMA stimulated U937 cells from three day serum-free cultures were also retained for mRNA isolation. Human blood monocytes prepared as described international patent application WO86/01212, and cultured for 3 days in vitro were also used as a source of mRNA.

Total RNA from each of the above sources was extracted by a modification of the Guanidin-HCL method [Chirgwin, J. M. et al Biochemistry 18 5294 (1979)]. The cell pellet was homogenized in 20 volumes (per gram weight) of buffer containing 4M quanidine isothiocyanate, 50 mM Tris HCl, ph7.5, 10 mM EDTA, 0.5% Sarkosyl, 0.1M 2-mercaptoethanol in a blender at low speed for three minutes at 4° C. The suspension was then centrifuged at 5,000 x g for 10 minutes at 4° C. to remove debris. Subsequent centrifugations were carried out at 5–10,000 x g unless specified otherwise. Nucleic acids were precipitated from the supernatant by the addition of acetic acid to 25 mM and 0.75 volumes of cold ethanol, and incubated overnight at −20° C. The suspension was centrifuged again for 30 minutes at −10° C., and the pellet dissolved in buffer containing 7.5M guanidine HCl, 20 mM sodium acetate pH5.0, 1 mM dithiothreitol at 20% of the original volume. After centrifuging to remove any undissolved material, the RNA was reprecipitated with 0.55 volumes of cold ethanol at −20° C. for 1–3 hours. The RNA was recovered by centrifugation, redissolved in the guanidine HCl buffer, and reprecipitated. The last step was repeated 3 times. Following the last precipitation,the pellet was dissolved in 20 ml of 20 mM EDTA, pH7.0 and extracted with an equal volume of chloroform: butanol (4:1). RNA was then precipitated from the aqueous phase by the addition of sodium acetate, pH5.0 to 0.3M and two volumes of cold ethanol at −20° C. overnight. The RNA was recovered by centrifugation and treated with 100 mg/ml proteinase K in 20 mM HEPES, pH7.4, 0.5% sodium dodecyl sulfate for 4 hours at 50° C. to remove any residual protein. The RNA was then recovered by precipitation in the presence of 0.2M sodium acetate, pH5.0 and two volumes of ethanol at −20° C. Following recovery by centrifugation, any residual DNA was removed by precipitation of the RNA in the presence of 3M sodium acetate, pH6.0, overnight at 4° C. The RNA was recovered by centrifugation at 15,000 x g at 4° C. for 1 hour and precipitated in the presence of 0.2N sodium chloride and two volumes of ethanol. The RNA was again recovered by centrifugation. Poly A+mRNA was then isolated by two cycles of adsorption and elution from oligo (dT)-cellulose [Aviv, H. Leder, P. Proc. Natl. Acad. Sci. USA 69 1408 (1972)].

Figure 2:
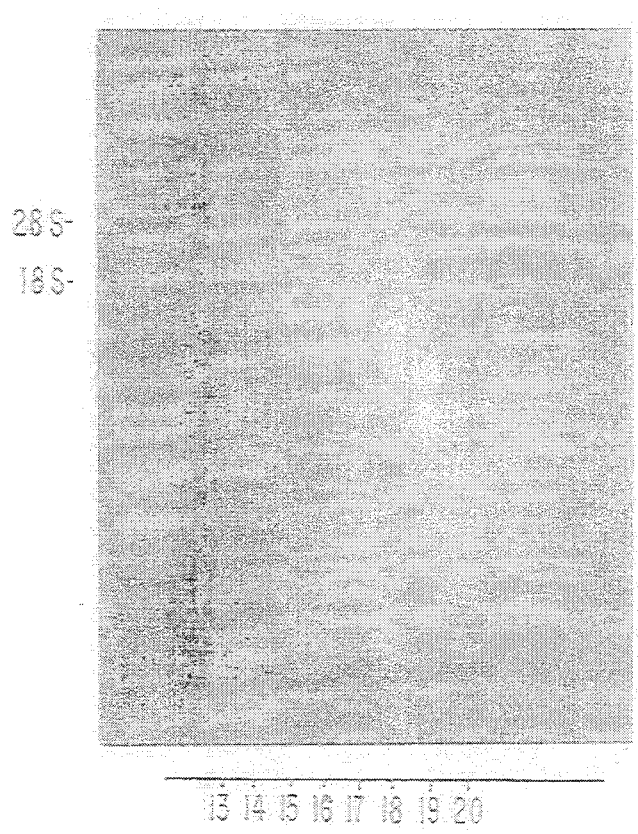
FIG. 2 is a gel analysis of a size fractionated minactivin mRNA preparation.
Figure 3:
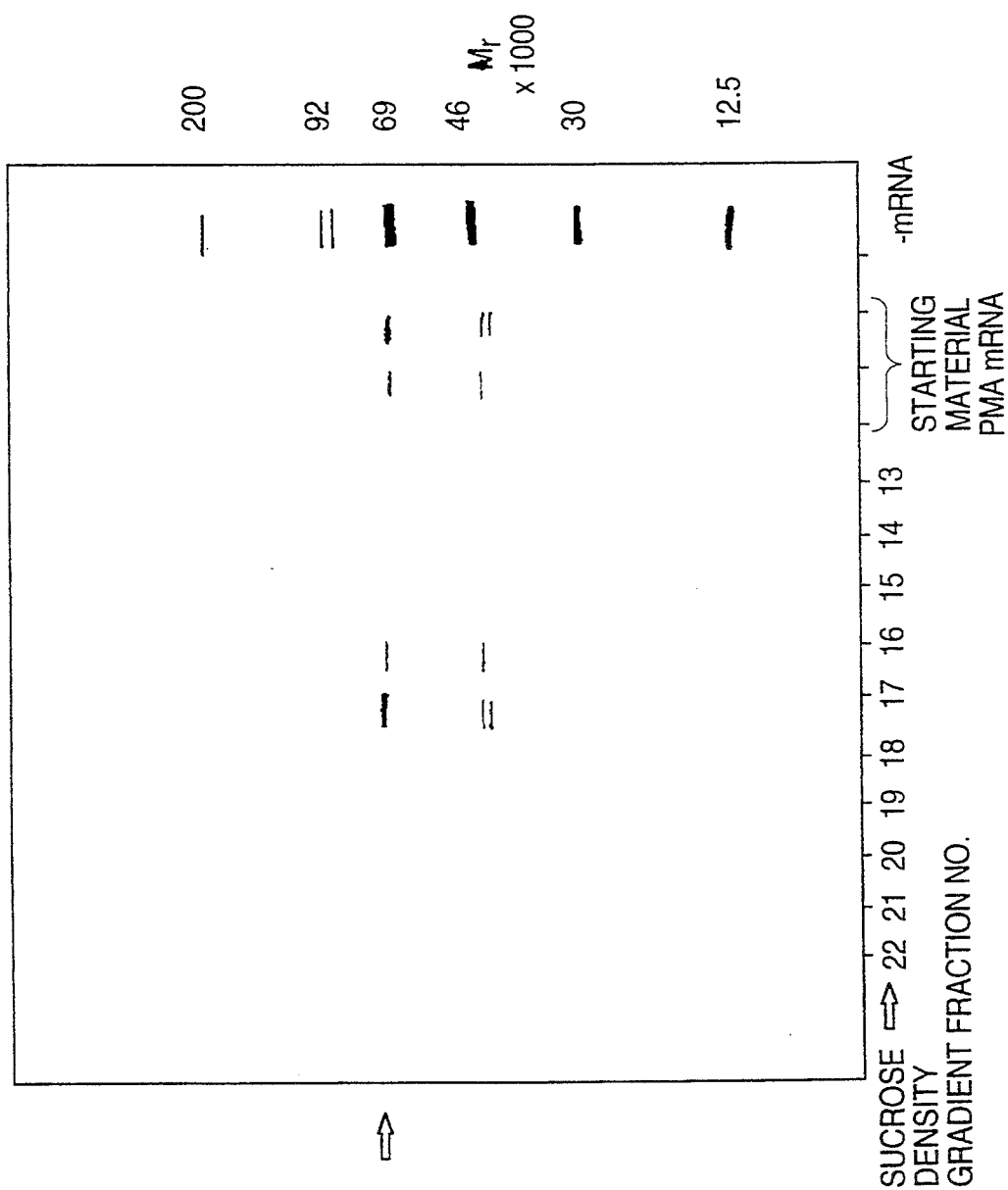
FIG. 3 is an autoradiograph of the immunoprecipitation products following in vitro translation of size fractionated mRNA showing minactivin mRNA in the fractions centred around 18S rRNA standard.

The poly A+mRNA was enriched 10 to 20 fold for minactivin mRNA by sucrose density gradient centrifugation. The sample was layered on a 15 to 34% (w/w) sucrose gradient and centrifuged in a Beckman SW41 rotor at 33,000 rpm for 16 hours at 4° C. FIG. 2 shows a gel analysis under denaturing conditions of the size fractionated mRNA preparation. Minactivin mRNA was detected in those fractions (Fractions 16 and 17) centered around the 18S ribosomal RNA standard as determined by in vitro translation and immunoprecipitation (method described below) as shown in FIG. 3.

b) Identification of the Minactivin Translation Product

Minactivin mRNA was identified by in vitro translation in a cell free reticulocyte lysate followed by immunoprecipitation of the minactivin translation product utilizing its natural substrate, urokinase.

Rabbit reticulocyte lysate commercially available from Amersham, was used primarily according to the manufacturer's instructions with the addition of calf liver tRNA (Boehringer Mannheim) at a concentration of 100 ng/ml. $^{35}$S-methanionine (Amersham) was added at a concentration of 2 mCi/ml to allow detection of the translation products by autoradiography. Poly A+mRNA prepared as described above was translated at a concentration of 50 mg/ml for 90 minutes at 30° C. Twenty-five microliters of the translation mixture was used for each immunoprecipitation. Following incubation and removal of a washed suspension of whole

*Staphylococcus aureus* cells (Pansorbin, Calibiochem) to minimize nonspecific binding, the sample was incubed with 50 mPU of urokinase (Calibochem) for 90 minutes at room temperature. This step allows complex formation between the minactivin translation product and urokinase. The complex was removed from the solution by the addition of 1-2 microliters of anti-urokinase antiserum (Green Cross Corp.), or antibodies against placental inhibitor and incubated at room temperature for 30 minutes and overnight at 4° C., and then precipitated by the addition of 25 microliters of washed Pansorbin. After centrifugation the minactivin-urokinase-antibody-Pansorbin pellet was washed by repeated centrifugation and resuspension in 0.05% Nonidet-P40, 0.15M NaCl, 5 mM EDTA, 50 mM Tris HCl pH 8.0, 0.025% sodium azide, disrupted by boiling in the presence of 2% SDS, and 2-mercaptoethanol, and the products analyzed by gel electrophoresis followed by autoradiography.

Figure 4:
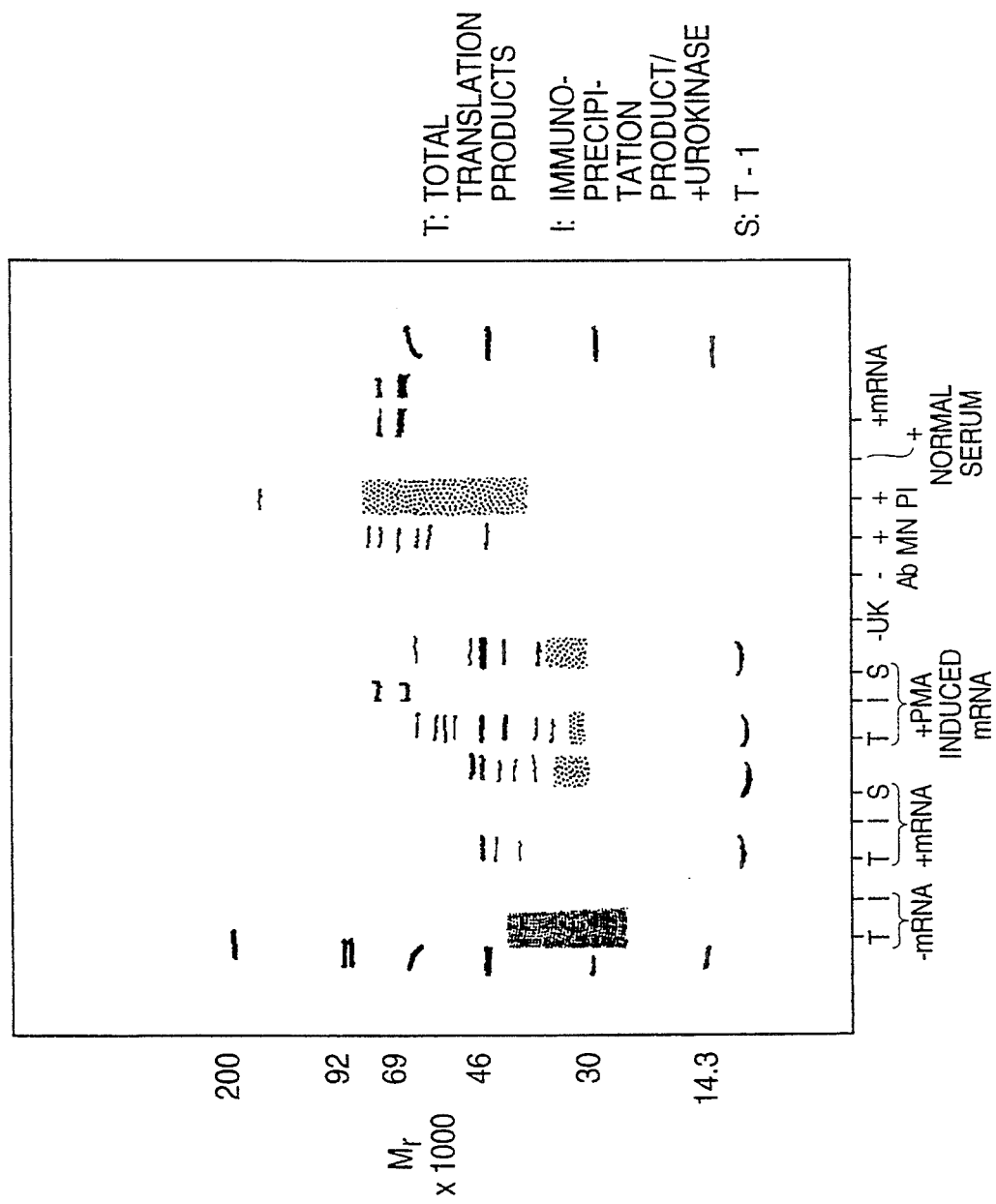
FIG. 4 is an autoradiograph of immunoprecipitated translation products showing the specificity of complex formation with urokinase using anti urokinase antibodies.

Immunoprecipitation of the $^{35}$S-labelled translation products with antibodies against urokinase yielded urokinase specific translation products having $M_r$S of 69,000 and 79,000. These protein bands represent specific complexes of minactivin with urokinase as:

1) they are not present in the absence of urokinase or mRNA;
2) they do not precipitate in the absence of antibody, and;
3) they compete with the unlabelled purified minactivin and placental inhibitor (Calibiochem) preparations for urokinase binding (FIG. 4).

The immunoprecipitated product was found to represent 0.05% of the total protein synthesized from mRNA obtained from PMA induced U937 cells. No immunoprecipitation products could be detected from mRNA obtained from non-induced U937 cells, presumably due to the decreased levels of minactivin mRNA in this preparation.

Figure 5:
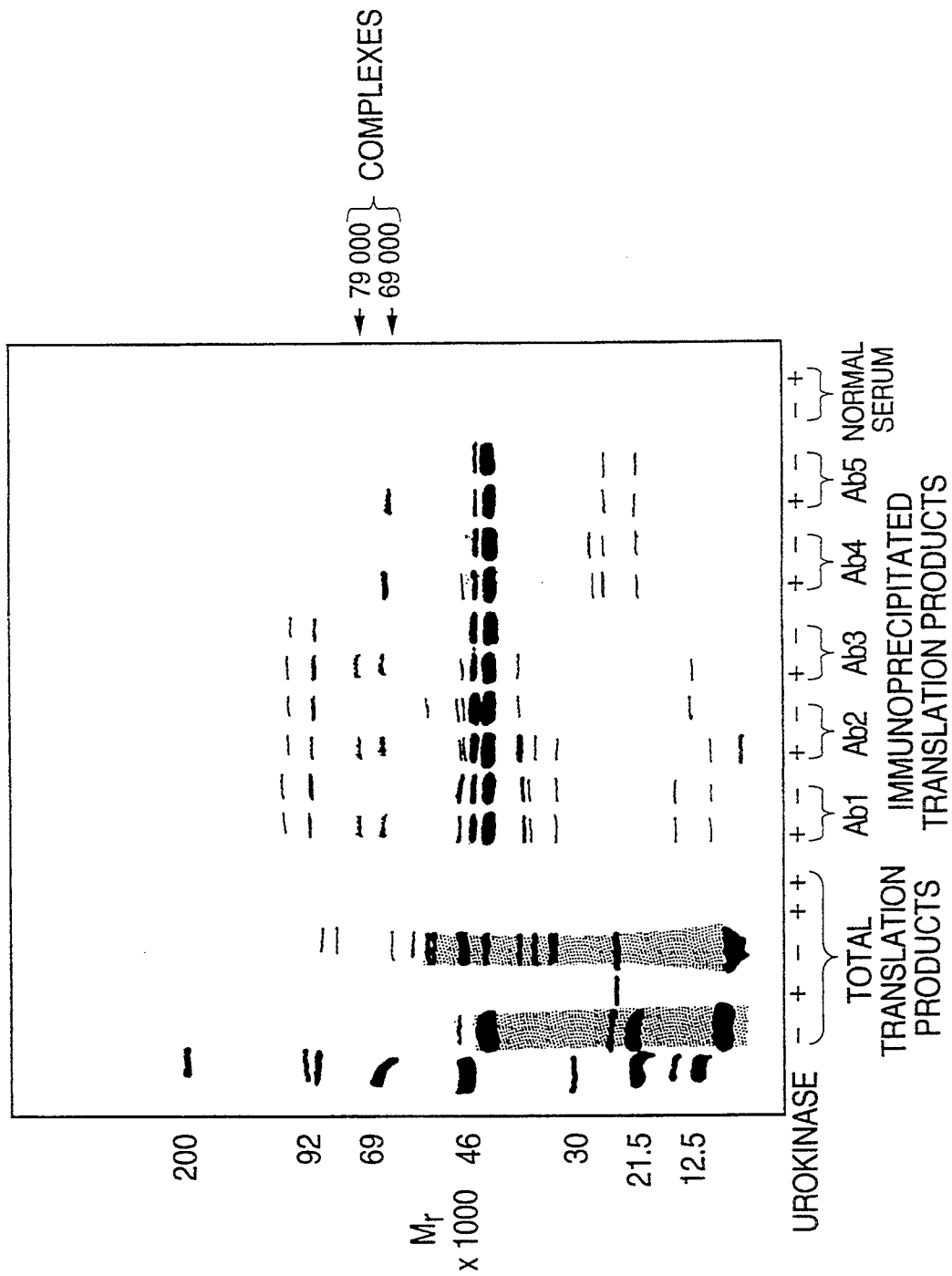
FIG. 5 is an autoradiograph of immunoprecipitated translation products showing the specificity of complex formation with urokinase using anti placental inhibitor antibodies. (autoradiograph showing identity of results using anti placental inhibitor antibodies with results using anti urokinase antibodies).

Immunoprecipitation of the urokinase—minactivin translation products using antibodies to placental inhibitor yielded identical results. Several anti-placental inhibitor antibody preparations precipitated the distinctive urokinase-minactivin translation product complexes at 69,000 and 79,000 MW (FIG. 5).

Figure 6:
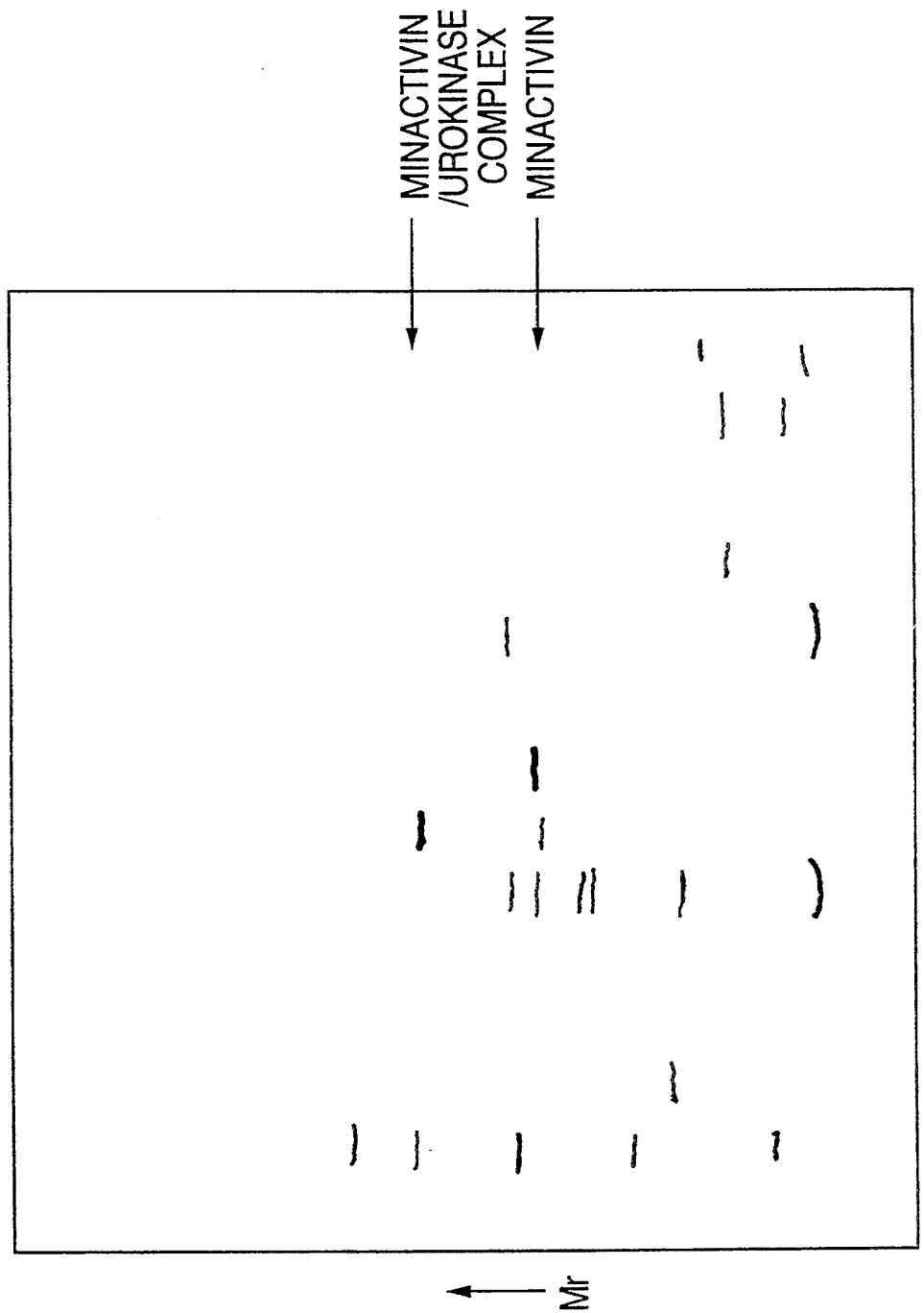
FIG. 6 is an autoradiograph showing identification of the minactivin translation product by comparison of immunoprecipitation products in the presence and absence of urokinase under reducing conditions.

A comparison of the immunoprecipitation products obtained in the presence and absence of urokinase allows direct identification of the minactivin translation product as shown in FIG. 6. It is present as a distinct band at a $M_r$ of 43,000. This molecular weight appears to be slightly less than that observed for the native protein possibly due to glycosylation. In the presence of urokinase, this band disappears and the characteristic urokinase-minactivin translation product is detected at 69,000 $M_r$. The additional protein band at 79 to 80,000 $M_r$ observed previously appears to represent a non-reduced form of the complex as the samples were analyzed under partially reduced conditions.

Figure 7:
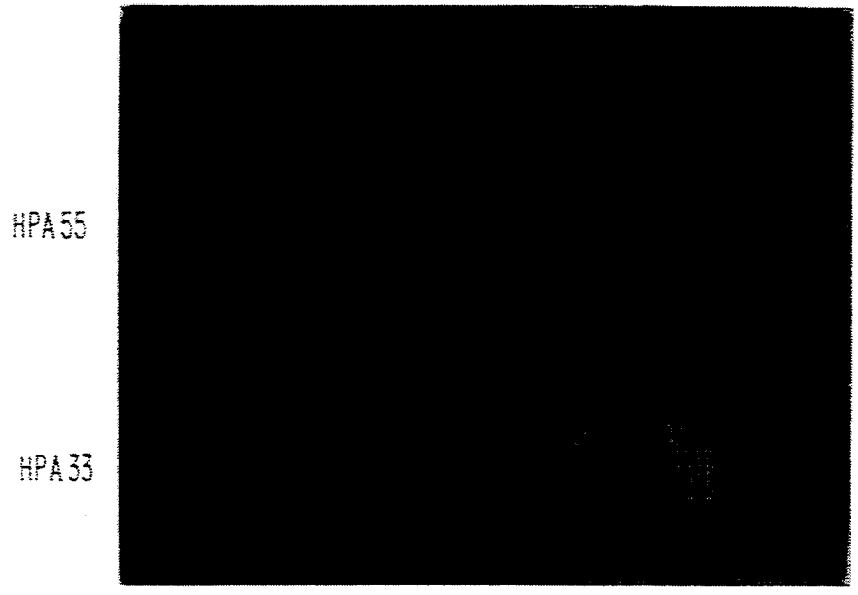
FIG. 7 is a representation of a gel showing differentation of urokinase species using the fibrin overlay technique.

Furthermore, it was found that complex formation with the minactivin translation product was dependent on the presence of the low molecular weight form of urokinase (HPA 33). Pure preparations of HPA 52 and HPA 33 was obtained (Calibiochem) and verified to be predominantly one species or the other by fibrin overlay (FIG. 7). In addition, plasminogen/plasmin was added to HPA 33 to convert any residual traces of HPA 52 in the preparation to the low molecular weight form. The distinctive urokinase-minactivin translation product complex at 69,000 MW appeared only when the urokinase preparations used contained HPA 33. The explanation for this result is unknown. Addition of trasylol to the lysate mixture to inhibit possible proteolysis had no effective on this result.

In summary, in vitro translation of mRNA from U937 cells clearly yields a biologically active minactivin translation product of $M_r$ approximately 43,000 which can be easily identified by the formation of its complex with urokinase giving a characteristic $M_r$ of 69,000.

c) Construction of Complementary DNA Libraries cDNA libraries were constructed from total poly A+mRNA or sucrose density gradient fractionated mRNA using a variety of established methods [see in general Maniatis, T. et al Molecular Cloning (1982)]. By way of example, the first strand complementary DNA was generally synthesized from the mRNA using primer initiated reverse transcriptase. Second strand was then synthesized, for example, by (1) conventional hairpin-loop primed DNA synthesis using DNA polymerase or reverse transcriptase [Maniatis, T. et al. Molecular Cloning (1982)]; (2) RNase H-DNA polymerase I—mediated second strand synthesis [Grubler, U. Hoffman, B. J. Gene. 25 (1983) 263-269, Laperye, B. Amabric, F. Gene 37 (1985) 215-220]; or (3) 5'-tailed priming method of Land, H. et al Nucleic Acid Research 9 2251-2266 (1981). After treatment with S1 nuclease (if required), the DNA is methylated and blunt ends generated using standard methods of filling-in, e.g. DNA polymerase, the Klenow fragment, or T4-polymerase. Subsequently, the cDNA's can be cloned by joining them to suitable plasmid (e.g. pBR322, UC or pUR systems) or bacteriophage (e.g. lambda gt 11) vectors through complementary homopolymeric tails or cohesive ends created with synthetic linker segments containing appropriate restriction sites using standard procedures, and then transforming a suitable host.

EXAMPLE 5

A preferred method of constructing the cDNA libraries is as follows. Methods for purifying DNA from both *E. coli* and bacteriophages lambda, and subsequent standard manipulations such as digestion with restriction enzymes, ligations and transformations and radiolabelling of DNA with $^{32}$P-ATP, as well as phenol:chloroform extraction and ethanol precipitation of DNA which are used in Examples 5 to 10 are as described by Maniatis, T. et al. Molecular Cloning (1982). cDNA was synthesized from 6 micrograms of total poly A+mRNA using Moloney murine leukemia virus reverse transcriptase (BRL, 200U/microgram mRNA) in the presence of 50 mM Tris HCl, 75 mM KCl, 10 mM DTT, 3 mM MgCl, 1 mM each of dATP, dCTP, dGTP, and dTTP, 10 micrograms/ml Oligo (dT)$_{12-18}$ and 100 micrograms/ml BSA. A 200 microliter reaction volume was incubated at 37° C. for 40 minutes. Second strand was synthesized by hairpin loop primed synthesis using the Klenow fragment of DNA polymerase I. The reaction was heated at 70° C. for 10 minutes to separate DNA/RNA duplexes, diluted to twice the volume and Klenow added to 325U/ml in the presence of 10 microCuries of dATP (1800 Ci/mmole). The reaction was allowed to incubate for 1 hour at 15° C. Following phenol:chloroform (1:1) extraction and ethanol precipitation [as described by Maniatis, T. et al Molecular Cloning (1982)], the DNA was dissolved and the hairpin loop was removed by treatment with 80 units of S1 Nuclease (P/L Biochemicals) in the presence of 0.2M NaCl, 50 mM sodium acetate pH 4.5, 1 mM ZnSO₄ and 0.5% glycerol and precipitated as described previously.

The double stranded cDNA was then methylated using 20 Units of EcoRl Methylase (Biolabs) in the presence of 100 mM Tris-HCl pH 8.0 10 mM EDTA and 80 micro-molar S-adenosyl methionine. The DNA was repaired by the addition of 2.5U of T4 DNA Polymerase in the presence of 33 mM Tris acetate pH8.0, 66 mM potassium acetate, 10 mM magnesium acetate, 0.5 mM dithiothreitol, 0.1 mg/ml BBA and 0.5 mM each of dATP, dCTP, dGTP, and dTTP for 1 hour at 37° C., followed by the addition of T4 polynucleotide kinase (20U) and 0.1 mM ATP. Following phenol:chloroform (1:1) extraction and ethanol precipitation [as described by Maniatis, T. et al Molecular Cloning (1982)], Eco R1 linkers were added to the redissolved DNA (2 micrograms linkers/micogram cDNA) using T4 DNA ligase (IBI; 1.2U/microgram, DNA). The reaction was carried out on a concentrated cDNA solution (167 micrograms/ml) at 26° C. for 4 hours. After treatment with EcoRl, the free linkers were separated from the dDNA by gel filtration chromatography on Biogel A 50M, as described by Huynh, T. V. et al DNA Cloning Vol 1 p 49–78 (1985). Fractions containing cDNA were analysed by agraose gel electrophoresis followed by autoradiography and those fractions containing cDNA of average length greater than 1,000 b.p. were pooled and the cDNA concentrated by lyophiulization to near dryness and precipitated by the addition of two volumes of ethanol. The yield of cDNA was 2.5 micrograms.

cDNA libraries were prepared in both lambda gt 11 and gt 10. cDNA (100 ng) was ligated to EcoRl-cleaved, phosphatased lambda gt 11 (1 microgram), at a DNA concentration of 220 micrograms/ml at 4° C. for 16 hours. The DNA was packaged using prepared packaging preparations from Vector Cloning Systems. Phages were amplified by adsorption to *E. coli* strain Y1088 and screened in Y1090. The lamba gt 11 library contained approximately 8×10⁶ recombinants per microgram cDNA (94% of total phages). The proportion of recombinants that contained cDNA molecules was determined by screening the library with cDNA synthesized in the presence of alpha[³²P]-dATP. Around 90% of white plaques hybridized with this probe.

For the library prepared in lambda et 10, cDNA (200 ng) was ligated to EcoRl cleaved, phosphatased lambda gt 10 (1 microgram), at a DNA concentration of 240 micrograms/ml at 25° C. for 4 hours. The DNA was packaged as above using *E. coli* strain C600 hfl.

The lambda gt 10 library contained approximately 7.5×10⁶ recombinants per microgram cDNA. The proportion of recombinants that contained cDNA molecules was determined by screening the library with radiolabelled cDNA. Greater than 90% of plaques hybridized with this probe.

EXAMPLE 6

Identification of Clones containing the Minactivin Gene

The clone(s) containing the gene encoding minactivin may be identified with the probes described in the following examples using established techniques [see generally Maniatis, T. et al Molecular Cloning (1982].

EXAMPLE 6a cDNA clones containing sequences complementary to minactivin mRNA may be identified by hybridization selection [Maniatis, T. et al Molecular Cloning (1982]. The cloned DNA is denatured, immobilized to a solid matrix such as nitrocellulose, and hybridized to preparations of total mRNA. The RNA/DNA duplex is heated to release the mRNA which is then translated in the in vitro rabbit raticulocyte lysate cell free system as described above. The translation product may then be identified as described in Example 4b.

EXAMPLE 6b

DNA Probes Complementary to the Minactivin Gene Sequence

Using the amino acid sequence obtained for peptides of minactivin as described in Example 3, oligonucleotide sequences which would code for the amino acid sequence can then be predicted and oligonucleotide probes synthesised using conventional established technology [Beaucage, S. L. and Carruthers, N. H. Tetrahedron Letts 1859–1862 (1981)]. Using this sequence data, a number of oligonucleotide probes were synthesized using an Applied Biosystems 380A DNA synthesizer. The sequences of these oligonucleotides are set forth in SEQ. ID. NOs. 6, 7, 8, 9, 10, 11, 12, 13, 14 and 15, respectively, and as follows:

```
                 (C)
   (A)   (T)     (G)        (A)
1. TT(G) AA(C) TG(A) ACI  AT(G) TA
                 (T)

(A)         (A)
   (G)   (T)   (G)   (C)
2. TA(T) AC(C) TC(T) AC(T) TC
   (C)         (C)

(A)   (A)
   (G)  (A)    (T)   (G)
3. TC(T) A(G)I  AT(C) TG(C) GC
   (C)         (T)

(T)                             (T)        (T)
4. TTG AA(C) TGI  ACI  ATG TAI  AC(C) TCI  AC(C) TC (T)
5.  (T)          (A)    (C)        (A)
   TC(C) TCI  AT(G) TA(A) CCI  AT(G) TT
                        (G)
```

```
            (T)          (T)
            (C)          (G)(C)
6. AA I  TT(A) GCI  C(T)(A) CC
            (G)          (G)
```

7. ATA TGT TTC CTC GAG CTT GAA CTG AGG GAT GTA CAC CTC GAC TTC GCT CTC TGC CAT

8. TTC ATC AGG CAA CAG GAG GAA CAT GCT CAC ATC TCC GGC GTA AGG GAG TTC CAG GAT CTT CAT TTT

9. CTC CTC CAG CTT GAA CTG GGG GAT GTA GAC CTC CAC CTC

```
        (A)      (G)          (C)
10. CTT GAA CTG (G)GG (A)AT GTA (G)AC CTC CAC CTC
```

The specific oligonucleotide probe may be radiolabelled and then used to screen cDNA libraries by in situ hybridization of bacterial colonies or bacteriophage plaques using standard techniques [Maniatis, T. et al Molecular Cloning (1982)] to identify clones containing all or part of the minactivin gene.

EXAMPLE 6C

Immunological Screening

The clones may be screened using established procedures (Young, R. A. and Davis, R. W. Science 222 778-782) with antibodies which cross-react with the native minactivin protein.

Antibodies to minactivin are prepared by standard methods, for example, each rabbit is immunized with 10 to 100 micrograms of purified minactivin in the presence of a suitable adjuvant, such as Freunds complete or montanide. Following a boost of an equivalent amount approximately four weeks later, the rabbit is bled and rabbit serum obtained which is assayed for antibodies to minactivin. Antiserum prepared in this way was used to immunoprecipitate the minactivin translation product as shown in FIG. 5 using Ab2 (bled 1 week after boost) and Ab3 (bled 2 weeks after boost) antisera. These antisera could be used to screen expression libraries prepared in lambda gt 11 according to published methods [Huynh, T. V. et al DNA Cloning Vol 1 49–78 (1985)].

EXAMPLE 6d

Screening for Biological Activity

Clones containing the minactivin gene maybe tested or screened for minactivin activity using either radiolabelled urokinase or urokinase and antibodies to urokinase. This would be accomplished using standard techniques of immunological screening, as described in Example 6c. Urokinase and antibodies to urokinase may be obtained commercially. Radiolabelled urokinase may be prepared as described below.

Commercially obtained urokinase (Calibiochem) was affinity purified by chromatography on p-aminobenzamidine sepharose according to published protocols [Holmberg, L., Bladh, B., Astedt, B. Biochim. Biophys. Acta 445, 215–222 (1976), and Goldfabr, R. H., Quigley, J. P. Biochemistry 19, 5463–5471 (1980]. Seventy-five Ploug units of the purified urokinase was iodinated by conjugation with N-succinimidyl 3-(4-hydroxy, 5-[$I^{125}$]iodophenyl) proprionate according to the Bolton Hunter procedure. The $I^{125}$-labelled urokinase was separated from the free label by chromatography on Sephadex G-25M equilibrated in 0.1M sodium phosphate, pH 7.0, 0.4M sodium chloride, 0.1% Triton X100 and 1% carrier bovine serum albumin.

Analysis of the $I^{125}$-labelled urokinase preparation by SDS—polyacrylamide gel electrophoresis under non-reducing conditions showed the presence of the characteristic high ($M_r$ 55,000) and low ($M_r$ 33,000) molecular weight forms of urokinase (FIG. 13). Under reducing conditions, the high molecular weight form is dissociated into its characteristic 33,000 and 22,000 $M_r$ subunits. Iodination of the urokinase preparation resulted in a loss of 10 to 15% plasminogen activator activity as measured by the assay of Coleman and Green [Ann. N.Y. Acad. Sci. 370, 617 (1981)], but had no effect on minactivin inhibition of the enzyme. Dot blot assays in which various dilutions of minactivin were spotted on nitrocellulose paper, incubated overnight with radiolabelled urokinase, washed, dried,and autoradiographed, showed that the radiolabelled urokinase could detect minactivin bound to a solid phase at a sensitivity of 10 mU or approximately 0.1 ng minactivin.

EXAMPLE 7

Identification of the Minactivin Gene

The preferred method of identifying the minactivin gene is as follows. Following synthesis, the oligonucleotide probes 7–10 described in Example 6b and set forth in SEQ. ID. NOs. 7, 8, 9 and 10 were purified by polyacrylamide gel electrophoresis, and labelled with polynucleotide kinase (IBI, 1U/pmole DNA) and gamma-$^{32}P$-ATP and purified by ion exchange chromatography using standard procedures [see generally Maniatis, T. et al Molecular Cloning (1982)].

The lambda gt10 library as described in Example 5 was screened by in situ hybridization according to standard experimental procedures [see generally Maniatis, T. et al. Molecular Cloning (1982)]. Hybridization conditions were adjusted to allow specific binding with minimum background and were determined to be as follows:

Probes 7 and 8 (SEQ. ID. NOs. 7 and 8): 3 hours at 50° C. in 6xSSC, 5×Denhardt's, 0.1% SDS, 20 $\mu g$/ml tRNA, following prehybridization for 1 hour at 42° C. in 6xSSC, 5xDenhardt's 0.5% SDS, 0.2 mg/ml sheared calf thymus DNA.

Probes 9 and 10 (SEQ. ID. NOs. 9 and 10): 16 hours at 37° C. in 10x Denhardt's, 5xSSC, 0.05% sodium pyrophosphate.

$^{32}P$-labelled oligonucleotide probes of specific activity greater than $10^8$ cpm/$\mu g$ were used at approximately 0.5 pmole/ml. The filters were washed in 0.5X or 2xSSC containing 0.1% SDS at increasing temperatures to raise the stringency for selection of positive clones.

Plaques giving positive signals were picked, rescreened, and the phase DNA purified using standard procedures (see for example Maniatis et al. Molecular Cloning 1982).

Two recombinant bacteriophage clones MIN1D and MIN611, containing sequences which cross-hybridized to each other were obtained, with EcoRI-linkered cDNA inserts of 2100 and 1060 base pairs respectively. These inserts were subcloned into plasmid pUC18 to create plasmids pBTA440 and pBTA441 respectively and mapped by restriction enzyme analysis as shown in FIG. 20. Southern blot analysis of clone MIN1D located the binding region of oligonucleotide probes 7 and 8 (SEQ. ID. NOs. 7 and 8) within a 320 base pair XbaI-NcoI restriction fragment as illustrated in FIG. 20.

That these clones contained genes which code for minactivin was verified by hybrid-select translation and DNA sequence analysis.

Hybrid Select Translation

Purified pBTA440 was immobilized on nitrocellulose filters at a concentration of 20 µg per 3 mm×3 mm filter according to the procedure described by Maniatis et al. (Molecular Cloning 1982). After washing, each filter was incubated with 50 µg of total mRNA and hybridized for 3 hours at 50° C. After thorough washing, the specifically hybridized mRNA was eluted at 65° C. and then translated in vitro using a commercial rabbit reticulocyte lysate preparation (Amersham).

As illustrated in FIG. 21, the hybridized mRNA was shown to specifically code for a translation product of $M_r43,000$ by gel electrophoresis, characteristic of the minactivin translation product described in Example 4b. Furthermore in the presence of urokinase, this band disappeared and the characteristic urokinase-minactivin complex was detected at $69,000 M_r$.

DNA Sequence Analysis

Restriction fragments of pBTA440 were subcloned into the single stranded phase vectors M13mp9, M13mp18 and M13mp19 and the DNA sequence of the 2,100 bp inserted was determined using the Sanger chain termination method. Examination of the DNA sequence indicated that the 2100 bp insert did not contain the entire coding sequence of the minactivin gene.

Primer Extension

To obtain the remainder of the DNA sequence encoding the N-terminal region of minactivin a second cDNA library was constructed using primer extension (Luse, D. S. et al, Nucleic Acid Research 9 (17) 4339–4355 (1981]. The library was prepared by priming 5 micrograms of poly A+mRNA with the oligonucleotide set forth in SEQ. ID. No. 16 being complementary to the previously sequenced nucleotides 391 to 420. EcoRI-linkered cDNA inserts were subsequently cloned in lambda gt10 using standard techniques.

Approximately $5.3 \times 10^3$ of the $7.2 \times 10^4$ clones obtained were screened with a second oligonucleotide as set forth in SEQ. ID. NO. 17 (complementary to nucleotides 310–335). Of the 100 positive clones obtained, 15 were purified and the clone (clone 13) with the largest cDNA insert (430 bp) was subcloned into plasmid pUC18 to create plasmid pBTA442. The DNA sequence of pBTA442 was determined as described above (see also FIG. 20).

The coding sequence of the minactivin gene, contained in pBTA440 and pBTA443, a plasmid containing the 430 bp 5' minactivin sequence in pUC18 in opposite orientation to pBTA442, was made contiguous by recombining certain DNA restriction fragments to crate pBTA438 as shown in FIG. 22. E. coli K-12, strain JM109 containing pBTA438 has been deposited with the American Type culture collection, 12301 Parklawn Drive, Rockville, Md.20852. United States of America on 11 Feb. 1987 under accession number ATCC 53585.

The complete cDNA sequence (SEQ ID NO:18) of the minactivin gene and the deduced amino acid sequence of the minactivin protein are given in FIG. 23. The complete translation product consists of 415 amino acids (M 46 543). The gene encodes the 5 peptides (as set forth in SEQ ID. NO:18) obtained from the amino acid sequence (SEQ ID NO:19) analysis of native minactivin as illustrated in FIG. 23.

The DNA sequence analysis reveals that minactivin is a member of the serine protease inhibitor superfamily, (known as serpins) albeit specific for urokinase type plasminogen activators.

. EXAMPLE 8

Expression of Biologically Active Minactivin

High-level expression of the biologically active molecule is obtained, for example, by integration of the full-length cDNA present in pBTA438 into various vectors which can direct the synthesis of the protein in a variety of hosts such as bacteria or eukarotic cells (such as mammalian cells transfected or transformed with the vector). The vector preferably contains a nucleotide sequence capable of controlling expression of the nucleotide sequence coding for minactivin. This second nucleotide sequence may include, by way of example, a promoter sequence, polyadenylation sequences, or nucleotide sequences which allow the protein to be expressed as a hybrid molecule fused with another protein.

EXAMPLE 9

Bacterial Expression of Minactivin

The general approach is the preparation of an expression vector or cloning vehicle replicable in E. coli, which contains a DNA sequence which codes for the expression of minactivin.

Minactivin may be expressed in its native form or as a hybrid molecule fused to another protein. These constructions are shown n FIGS. 24 and 26.

One series of plasmid constructs used the lambda $P_L$ expression vectors pLK57, and pLK58 (Botterman et al. Gene 37; 229–239, 1985) to express native or near-native (N-terminal amino acid modified) minactivin.

As shown in FIG. 24, the plasmid pBTA438 was digested with EcoRI and DraI and a 1610 bp EcoRI-DraI restriction fragment was isolated from an agarose gel. This fragment was ligated with T4 ligase to vector pLK57 which had been digested with EcoRI and EcoRV. The derivative plasmid pBTA444 contains the lambda $P_L$ promoter controlling the expression of native minactivin.

The expression vector pBTA444 was used to transform E. Coli K-12 strain N4830 (Joyce et al. PNAS 80, 1830–1834, 1983) which contains the thermolabile CI repressor of lambda. Cells transformed with pBTA444 were grown overnight in MED medium (Mott et al PNAS 82, 88–92, 1985) 100 micrograms/ml ampicillin at 28° C. Cells were diluted in MEB medium, grown at 28° C. to an $OD_{600}$ of 1.0 when prewarmed (65° C.)

MEB medium was added in equal volume to equilibrate the temperature to 42° C.

Following 4 hours of growth at 42° C. the cells were harvested and membrane and soluble protein fractions prepared by resuspending washed cells (after −70° C. freezing and thawing) in 200 μof 20% sucrose 30 mM Tris-HCl pH8.1. and mg/ml lysozyme solution followed by the addition of 3 mls of 3M EDTA pH7.3. The cells extract was clarified by brief sonification and membrane and insoluble proteins pelleted by centrifugation (27,000xg), 60 mins). The soluble proteins were precipitated by the addition of trichloroacetic acid (10% w/v) to the supernatant and the pellet dissolved in water. The pelleted membranes was also dissolved in water. Samples of these fractions for both uninduced (28° C.) and induced (42° C.) cells were analysed by SDS-polyacrylamide gel electroploresis and immunological detection of minactivin by western transfer using antiserum against human placental inhibitor. As shown in FIG. 25 a minactivin protein band (Mr 40–50K), visualized by western transfer using antibodies to human placental inhibitor and rabbit anti-goat IgG coupled to alkaline phosphate (Sigma) is present in both the induced (42° C.) soluble and membrane fractions.

An alternative method for producing native minactivin is also shown in FIG. 24. The plasmid pBTA442 was digested with XhoII and a 243 bp XhoII restriction fragment was purified from an agarose gel. This fragment was ligated with T4 ligase to vector pLK58 digested with BglII. The derivative plasmid pBTA445 was digested with PvuII and SmaI and a 2800 bp fragment purified and ligated with T4 ligase to a purified 1320 bp PvuII-DraI restriction fragment from pBTA438. The derivative plasmid pBTA446 was linearized with BdlII and ligated to a synthetic double stranded 26 mer oligonucleotide containing a bacterial ribosome binding site and the initial nucleotides of the native minactivin gene, creating plasmid pRTA447. When pBTA447 is transformed into an appropriate host, such as N4830, induced and analysed as described above, minactivin is again produced as shown in FIG. 25. In both cases, for pBTA444 and pBTA447 containing cells, minactivin was present in both the induced (42° C.) soluble and membrane fractions.

To assess the biological activity of minactivin produced in E. coli N4830, soluble and membrane fractions were incubated for 90 mins with high and low molecular weight urokinase as described in Example 4. Samples were then precipitated with acetone, resuspended in water, and run on a reducing SDS-polyacrylamide gel. Minactivin and minactivin-urokinase complexes were visualized by Western transfer as described above. As shown in FIG. 25 minactivin in the soluble fraction from induced E. coli N4830 containing pBTA447 complexes with urokinase under standard assay conditions. This indicates that minactivin produced from these bacterial cells retains biological activity.

Figure 26B:
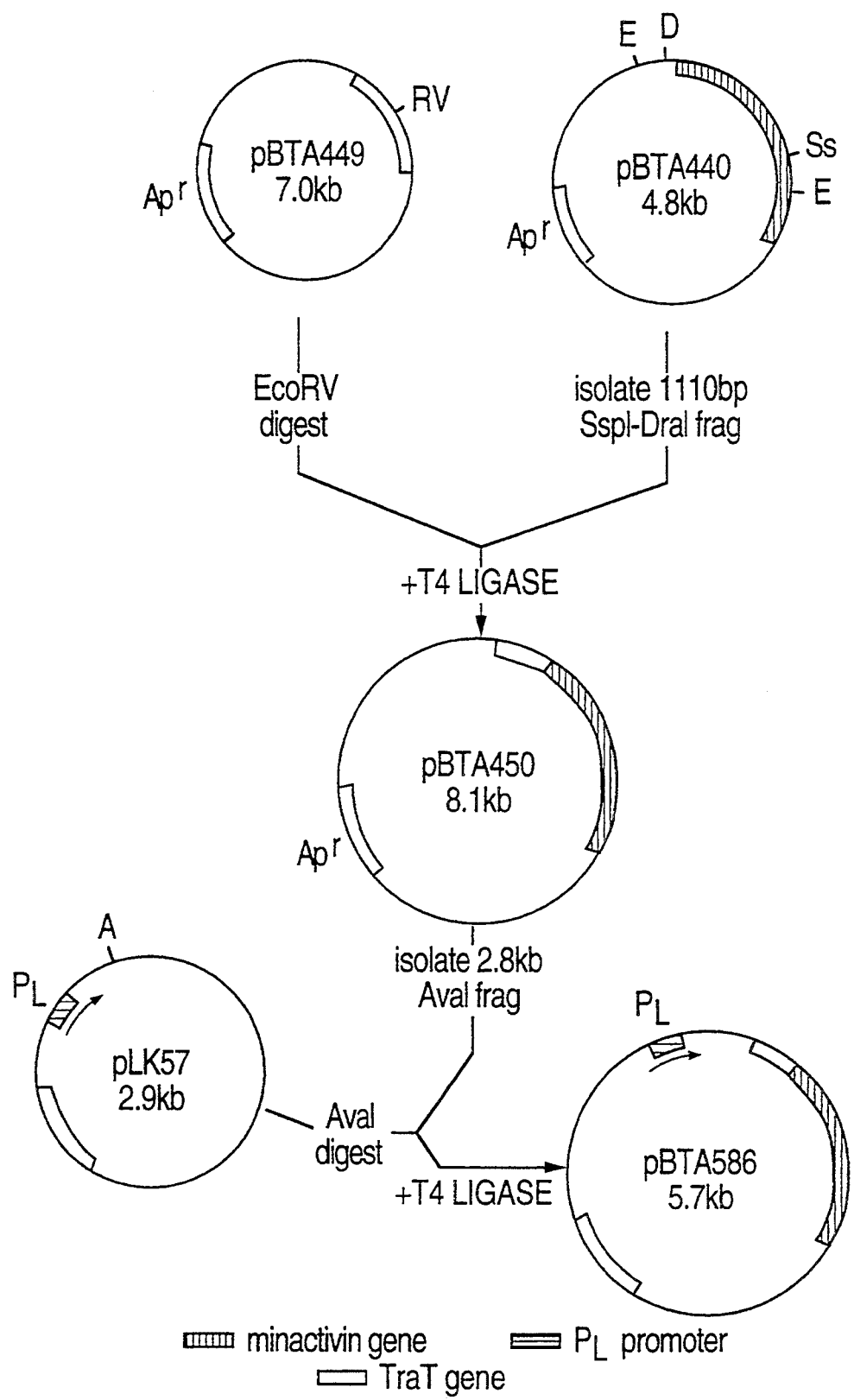

Two examples of a method for producing a protein that is the fusion of all or part of one protein coding sequence and all or part of the minactivin coding sequence follows. As shown in FIG. 26, the plasmid pBTA440 was digested with SspI and DraI and a 1110 bp fragment was isolated from an agarose gel. This fragment was ligated to the vector pBTA449 digested with EcoRV creating pBTA450. pBTA450 was then digested with AvaI and a purified 2800 bp fragment ligated to the plasmid pLK57 digested with AvaI to create plasmid pBTA586. This places part of the minactivin coding sequence under the control of the lambda $P_L$ promoter and fused to the coding sequence of the first 80 amino acids of traT gene, the first 20 of which constitutes a signal sequence that results in the fusion appearing in the outer member of E. coli. This signal sequence is cleaved off during transport to the outer membrane, which is the normal location of the traT protein.

When plasmid pBTA586 is transformed into an appropriate host, such as N4830 and induced with temperature shift as above, the TraT-Minactivin fusion protein appears in the outer membrane, as shown in FIG. 27.

A second example of a method for producing a fusion is shown in FIG. 26. In plasmid pBTA440, the minactivin coding sequence is fused in frame with a portion of the β-galactosidase gene present on plasmid pUC18.

When plasmid pBTA440 is transformed into an appropriate host, such as JM101, or any E. coli strain which contains the lacI$^q$ gene, and induced by addition of isopropyl-thio-β-D-galactopyranoside (final concentration 1 mM), minactivin production can be detected as described above (FIG. 27).

EXAMPLE 10

Expression of Recombinant Minactivin in Eukaryotic Cells

A fragment of pBTA438 containing the entire coding region of minactivin was inserted into a series of vectors capable of stable integration and expression of eukaryotic genes in mammalian cells. These included 1) pKC3 (derived from pKO-neo, Van Doren, Hanahan, D., Gluzman, Y., J. Virol. 50 606–614 (1982) wherein the minactivin cDNA sequence is placed under the control of the SC40 early promoter; 2) pZipNeoSV(X)1 (Cepko, C. L. Roberts, B. E., Mulligan, R. C. , Cell 37 1053–1062 (1982)), a Molony Murine Leukemia virus-derived retroviral shuttle system in which the minactivin gene is placed downstream from the retroviral LTR promoter and selection is based on the neo gene which confers kanamycin resistance in prokaryotes and G418 resistance in eukaryotes; and 3) pMSG (commercially available from Pharmacia), wherein regulated expression of minactivin is achieved by utilizing a dexamethasone inducible promoter contained within the Mouse Mammary Tumor-Virus (MMTV) 5'-LTR.

The construction of these three vectors is shown in FIG. 28 and the details are as follows. The coding region of the minactivin gene was isolated from pBTA438 as a 1610 bp EcoRI-DraI fragment and inserted into the following vectors as described below.

The 1610 bp EcoRI-DraI fragment was ligated into pKC3 which had been digested with EcoRI and SmaI, and then transformed into E. coli C600γ. The resultant plasmid was designated pBTA587.

In the second construction, the 1610 bp EcoRI-DraI fragment was rendered flush-ended using the Klenow fragment of DNA polymerase I, ligated into the SmaI site of pMSG, and transformed into a suitable E. coli K-12 host. Colonies containing the minactivin gene in pMSG were detected by colony hybridization using the $^{32}$P-labelled oligonucleotide (29 mer) previously described in Example 7 (complementary to nucleotides 310–335). The resultant plasmid was designated pBTA588.

In the third construction, the flush-ended EcoRI/-DraI fragment described above was ligated into pUC7 which had been digested with HincII giving the construction designated pBTA589. As the HincII site in pUC7 is flanked by BamHI sites, this allowed the minactivin gene to be isolated following BamHI digestion and ligated into the BamHI site of pZIPNeo SV(X) 1. Following transformation into a suitable *E. coli* K-12 host, colonies containing the minactivin gene were detected by colony hybridization as described above. The resultant plasmid was designated pBTA590.

Transfection of Eukaryotic Cells

All plasmids were transfected into eukaryotic cells by the calcium phosphate method. Approximately $1-2 \times 10^5$ cells were seeded into a T25 flask in 5 ml of Dulbecco modified Eagle medium supplemented with 10% (v/v) foetal calf serum, 3.6 mM glutamine 200 mM, 45IU/ml penicillin and 45 mg/ml streptomycin (complete medium). Approximately 1 to 5 µg of CsCl gradient purified DNA was precipitated with calcium phosphate and added to the cells. After 4 hours, the cells were treated to a glycerol shock, and cultured in complete medium for 3 days. The culture supernatant was then removed for measurement of transient expression. The cells were then trypsinized and split ⅓ into T75 flasks with complete medium containing the appropriate antibiotic selection (see below). The cells were washed every 6 to 7 days with the same medium and transfectants picked at 14 to 28 days and cultured individually until confluent growth was achieved.

The conditions of transfection for each of pBTA587, pBTA588 and pBTA590 were as follows:

pBTA587. As pKC3 does not contain a selectable marker, pBTA587 was cotransfected with pZIPNeo SV(X)1 at a molar ratio of 7.5:1, pBTA587: pZIPNeo SV(X)I. Transfectants were selected with complete medium containing 0.4 mg/ml G418. Transfections were carried out in COS cells.

pBTA588. As pMSG contains the *E. coli* xanthine-guanine phosphoribosyltransferase (gpt) gene expressed from the SV40 early promoters, stably transfected cells were selected in HAT medium containing hypoxanthine, aminopterin and mycophenolic acid.. Transfections were carried out using NIH3T3 cells.

pBTA590. Transfectants were selected using complete medium containing 0.4 mg/ml G418. Transfections were carried out in NIH3T3 cells.

Analysis of Expression of Recombination Minactivin in Eukaryotic Cells

Following transfection, transient expression of recombinant minactivin is detected by culturing the cells in the presence of $^{35}$S-methionine and specific immunoprecipitation of the recombinant radiolabelled minactivin using antibodies to placental inhibitor essentially according to the method described in Example 4b. For example, forty-eight hours after transfection of pBTA587 into COS cells, the supernatant was removed and the cells cultured in the presence of 1 ml methionine-free EMEM (Flow), supplemented with $^{35}$S-methionine (Amersham). Following immunoprecipitation with 50 mg goat anti-placental inhibitor antibodies and 200 ml washed Pansorbin, the complexes were analysed by SDS-polyacrylamide gel electrophoresis (reducing conditions) and visualized by autoradiography as shown in FIG. 29. Recombinant minactivin is detected as a band of Mr 45-48,000, which is not observed in the corresponding control transfection containing the vector (pKC3) alone. When urokinase (15 Plough units, Calbiochem) is added to the supernatant prior to immunoprecipitation, this band disappears which is characteristic of biologically active minactivin. A band is observed at $M_r$ 69,000 which is indicative of the minactivin urokinase complex, but is somewhat obscured by a nonspecific protein band at the same position. Some of the recombinant minactivin also appears to have been proteolytically nicked following the addition of the urokinase preparation, as evidenced by the $M_r$ 35-37,000 band detected.

That the recombinant minactivin produced was biologically active was determined by culturing the cells in the absence of serum for 4 hours and quantitating the inhibition of urokinase activity by the colorimetric assay essentially as described in Example 1. A level of inhibition was detected which corresponded to approximately 1 unit/ml minactivin activity above background.

Transfectants containing the minactivin gene can also be analyzed for minactivin activity using radiolabelled urokinase prepared as described in Example 6 or according to the method of Baker. Culture supernatants are incubated with the radiolabelled urokinase in order to allow complex formation between the recombinant minactivin and urokinase. The complex is then removed from the solution by the addition of rabbit antibodies prepared against urokinase (Green Cross Corp.) and precipitated by the addition of washed Pansorbin or anti-rabbit antibodies covalently attached to immunobeads (Biorad). After centrifugation, the minactivin-urokinase-antibody pellet is washed, disrupted by boiling with 2% SDS and the products analysed by gel electrophoresis followed by autoradiography. The presence of biologically active recombinant minactivin produced by the transfected cells is evidenced by the shift in molecular weight of urokinase from Mr 55,000 (or 33,000) to a higher Mr (69 to 92,000) (see Example 4b) characteristic of the formation of the minactivin-urokinase complex.

EXAMPLE 11

Purification and Recover of Biologically Active Protein

Following the establishment of conditions for the expression of minactivin in *E. coli* at high levels the cells harbouring the plasmid enclocing the minactivin gene are harvested at late log phase. One volume of packed cells are suspended in two volumes of lysis buffer (0.1M sodium phosphate. pH7.0 containing 1 mM EDTA and 1 mM phenyl methyl sulphenyl fluoride) and lysed by three passages through a French Press at 15,000 psi. The suspension is centrifuged at 23,000 xg for 20 minutes and the pellet resuspended in two volumes of lysis buffer containing 5% Triton X-100. The suspension is again centrifuged at 23,000 xg for 20 minutes and the pellet suspended in three volumes of 0.1M Tris-Cl, pH8.0 containing 8M urea and 0.1M DTT. The solution is flushed with nitrogen and incubated in a sealed tube at 37° C. for 2 hours. Following incubation the pH of the solution is lowered to approximately pH3.5 by the addition of 50 ml of glacial acetic acid for every ml of solution. The suspension is clarified by centrifuging as above and the supernatant applied to a Sephadex G-75 column (3.2 cm×90 cm) equlibrated in 0.1M acetic acid. The fractions containing the minactivin are located by SDS-PAGE. The fractions containing the minactivin are pooled and dialysed against 10 mM Tris-Cl, pH8.0 containing 8M Urea and 0.1 mM DTT at room temperature for 16 hours. The analysed solution is then applied to a DEAE-Sephadex column (2.2 cm×25 cm) equilibrated in the above buffer and the column washed to elute unbound material. The minactivin is then eluted from the column using a linear gradient of sodium chloride from 0 to 0.5 M in the same buffer. The fractions containing the minactivin are indentified by SDS-PAGE and dialysed extensively against distilled water. The protein, which precipitates during this procedure, is recovered by lyophilization. The lyophilized protein is redissolved in 0.1% trifluoroacetic acid and applied to a Vydac C-4 reverse phase column attached to a Waters high pressure liquid chromatograph. The pure minactivin is eluted from the column using a linear gradient of acetonitrile from 0 to 80% in 0.1% trifluoroacetic acid. The $A_{220}$ peak corresponding to minactivin is identified by SDS-PAGE, the fractions pooled and lyoplilized.

The lyophilized, purified minactivin is dissolved in 0.1M Tris-Cl, pH8.0 containing 8 urea at a concentration of 10 mg/ml and diluted to 10 mgm/ml into 0.1M Tris Cl, pH8.0 containing 1 mM reduced glutathione and 0.1 mM oxidized glutathione. The refolding reaction is allowed to proceed at room-temperature for 24 hours and then the solution concentrated and diafiltered against 0.1M sodium phosphate pH7.0 on an Amicon stirred cell using a YM10 membrane. The resultant solution containing active minactivin is assayed using the assay described above (Example 1).

The recovery of biologically active minactivin secreted at high levels from mammalian cells employs the same procedures as described in Example 2 for the purification of the native minactivin from U937 cells. This involves initially a ten fold concentration of the cell free supernatant using an Amicon DC-2 hollow fibre concentrator equipped with a 30,000 dalton cut-off cartridge. The concentrate is then dialysed against at least an equal volume of 50 mM glycine, pH7.8, to remove all traces of dye. The dialysed concentrate is centrifuged in a JA10 rotor at 8000 rpm for 30 min at 4° C to pellet residual cell debris and protein that may have precipitated during dialysis. The clarified supernatant is then aliquoted and frozen at −20° C. until required for subsequent purification.

Minactivin is further purified from ten-time concentrated culture supernatant by step pH elution using Phenyl-Sepharose as follows.

The ionic strength of the supernatant is adjusted to 2M by the addition of solid NaCl and the pH adjusted to 5.5 with citric acid. This solution is applied to a Phenyl-Sepharose column (4.4 cm×5.0 cm) equilibrated in 50 mM Na citrate, pH5.5, 2M Nacl and 1 mM EDTA and eluted with the same buffer until the baseline absorbance at 280 nm (A280) returned to baseline. The minactivin is then eluted from the column with 50 mM glycine, pH9.0. Fractions containing the highest specific activity minactivin are pooled and concentrated on an Amicon YM10 membrane.

The pooled, concentrated minactivin is then applied to a 2.2 cm×78 cm column of Sepharcyl S-200 equilibrated with 0.1M sodium borate, pH9.0. Fractions of 5.0 ml are collected at a flow rate of 0.46 ml/min. The fractions containing minactivin activity were pooled and concentrated in 3 ml using a YM10 membrane. Calibration of this column with known $M_r$ standards indicates that minactivin has a $M_r$ of 45–48 kD.

The concentrated minactivin solution is applied to a preparative flat bed gel of Ultrodex containing Ampholines in the pH range 4.5–6.0 and electrofocussed for 23 hrs at 10° C. on an LKB Multiphor isoelectric-focussing apparatus. Following completion of the run, 30 zones across the length of the gel are scraped out and the protein eluted from each with 10 ml of 1M glycine containing 1 mM EDYA, pH9.0. Aliquots of each frction are assayed for minactivin activity and electrophoresed on 15% SDS-polyacrylamide gels to locate protein. Under these conditions minactivin focusses between pH5 and pH5.2 and is highly purified. This material is again concentrated on an Amicon YM10 membrane and stored at −20° C. in 50 mM glycine, pH9.0, containing 1 mM EDTA and 50% glycerol.

Industrial Application

As a specific inactivator of urokinase-type plasminogen activiators, minactivin has a range of potential industrial applications as a clinical reagent for the diagnosis and possible treatment of various human carcinomas and inflammatory conditions.

Similarly, oligonucleotide probes derived from the amino acid sequence of peptides derived from purified minactivin or antibodies to minactivin can be used as diagnostic tools in assays for monitoring the status of diseases such as inflammation and cancer metastasis particularly during prescribed courses of treatment.

Studies of cell transformation in vitro by tumor viruses (Ossowski, 1 et al. J. Exp. Med. 137, 112, 1973) and by chemical carcinogens (Sisskin, et al. Int. J. Cancer, 26, 331, 1980) both show that plasminogen activator secretion is the most constituent early biochemical event associated with transformation. Furthermore, the ability of cell lines to metastasize in vivo has been found to correlate with their ability to express plasminogen activator (Wang et al, Cancer Research 40, 288, 1980). It is also well established that tumor cells of several of the most prevalent human cancers, i.e. carcinoma of the lug, breast, prostate and colon, produce high levels of urokinase-type plasminogen activator (Duffy, M. J., O'Grady, P. Eur. J. Clin. Oncol. 20 (5) 577–582, 1984).

Our previous studies (Stephens, R. S. et al. Blood 66, 333–337, 1985) on malignancy in colon mucosa and conditions which predispose to malignancy, i.e. adenomatous polyps, polyposis coli and inflammatory conditions of the colon such as Crohn's disease and ulcerative colitis, have demonstrated that human colon cancers produce significantly greater amount of urokinase-type plasminogen activator than that occurring in adjacent noninvolved tissue. Minactivin was found to be capable of binding to and inhibiting this tumor associated plasminogen activator (Stephens et al. Blood 65, 333–337, 1985). Thus, it follows that minactivin has industrial application as a reagent for identifying and defining tumors both in vivo and in histological specimens. For imaging tumors in vivo, minactivin may be labelled with an appropriate isotope, such as Technetium-99 m (Richardson, V. J. Brit. J. Cancer 40, 35, 1979) or Iodine-131 (Begent, R. H. J. Lancet, Oct 2, 1982). Following administration of the minactivin preparation, the location and boundaries of the tumor may be determined by known raidoisotopic methods, such as gamma-camera imaging. Thus, minactivin offers a sensitive method for enabling the identification of small metastatic cancers particularly those arising after surgical intervention. In the analysis of histochemical specimens, minactivin or its antibody, may be labelled with an isotope such a $I^{131}$, or conjugated to an appropriate enzyme or other chemical reagent. On contact with a histological specimen, such as a biopsy section, minactivin will bind to the tumor type plasminogen activator at its place of secretion, thereby identifying the tumor boundaries and potentially the metastatic state of the tumor. In addition to its diagnostic applications, minactivin is also indicated for use in the direct treatment of tumors. As a specific inhibitor of the enzyme implicated in the process by which tumors invade surrounding tissues (Dano, K. et al., Adv. in Cancer Res. 44, 139,1985), regulation and, in particularly, inhibition of tumor growth and metastases can be achieved. Furthermore, minactivin can be used as a drug delivery system to deliver lectins or toxins directly to growing tumors. It will be appreciated that this system could offer many advantages in terms of specificily and extremely potent tumoricidal capability.

Other biological processes in which urokinase-type plasminogen activators have been implicated involve those physiological events associated with invasion and tissue destruction, such as chronic inflammatory conditions including rheumatoid arthritis. As minactivin is part of the natural host response to tissue degradation, it will provide a useful marker for monitoring the status of the disease particularly during prescribed courses of treatment. Labelled antibodies or DNA probes derived from minactivin have industrial application as diagnostic reagents for monitoring minactivin levels in blood plasma, in macrophages of tissue biopsies and in synovial fluid for corelations with diseased states. Similarly, minactivin itself is also indicated to have a therapeutic effect when administered in vivo in amellorating such conditions.

EXAMPLE 12

Studies of cell transformation in vitro by tumor viruses (Ossowski, 1 et al. J. Exp. Med. 137, 112, 1973) and by chemical carcinogens (Sisskin, et al. Int. J. Cancer, 26, 331, 1980) both show that plasminogen activator secretion is the most consistent early biochemical event associated with transformation. Furthermore, the ability of cell lines to metastasize in vivo has been found to correlate with their ability to express plasminogen activator (Wang et al. Cancer Research 40, 288, 1980). It is also well established that tumor cells of several of the most prevalent human cancers, i.e. carcinoma of the lug, breast, prostate and colon, produce high levels of urokinase-type plasminogen activator (Duffy, H. J. O'Grady, P. Eur. J. Clin. Oncol. 20(5) 577-582, 1984).

Our previous studies (Stephens, R. S. et al. Blood 66, 333-337, 1985) on malignancy in colon mucosa and conditions which predispose to malignancy, i.e. adenomatous polyps, polyposis coil and inflammatory conditions of the colon such as Crohn's disease and ulcerative colitis, have demonstrated that human colon cancers produce significantly greater amount of urokinase-type plasminogen activator than that occurring in adjacent noninvolved tissue. Minactivin was found to be capable of binding to and inhibiting this tumor associated plasminogen activator (Stephens et al. Blood 66, 333-337, 1985). Thus, it follows that minactivin has industrial application as a reagent for identifying and defining tumors both in vivo and in histological specimens. For imaging tumors in vivo, minactivin may be labelled with an appropriate isotope, such as Technetium-99 m (Richardson, V. J. Brit. J. Cancer 40; 35, 1979) or Iodine-131 (Begent, R. H. J. Lancet, Oct. 2, 1982). Following administration of the minactivin preparation, the location and boundaries of the tumor may be determined by known radioiostopic methods, such as gamma-camera imaging. Thus, minactivin offers a sensitive method for enabling the identification of small metastatic caners particularly those arising after surgical intervention. In the analysis of histochemical specimens, minactivin or its antibody, may be labelled with an isotope such a $I^{131}$ or conjugated to an appropriate enzyme or other chemical reagent. On contact with a histological specimen, such as a biospy section, minactivin will bind to the tumor type plasminogen activator at its place of secretion, thereby identifying the tumor boundaries and potentially the metastatic state of the tumor. In addition to its diagnostic applications, minactivin is also indicated for use in the direct treatment of tumors. As a specific inhibitor of the enzyme implicated din the process by which tumors invade surrounding tissues (Dano, K. et al. Adv. in Cancer Res. 44, 139,1985), regulation and, in particularly, inhibition of tumor growth and metastases can be achieved. Furthermore, minactivin can be used as a drug delivery system to deliver lectins or toxins directly to growing tumors. It will be appreciated that this system could offer many advantages in terms of specificily and extremely potent tumoricidal capability.

Other biological processes in which urokinase-type plasminogen activators have been implicated involve those physiological events associated with invasion and tissue destruction, such as chromic inflammatory conditions including rheumatoid arthritis. As minactivin is part of the natural host response to tissue degradation. It will provide a useful marker for monitoring the status of the disease particularly during prescribed courses of treatment. Labelled antibodies or DNA probes derived from minactivin have industrial application as diagnostic reagents for monitoring minactivin levels in blood plasma, in macrophages of tissue biopsies and in synovial fluid for correlations with diseased states. Similarly, minactivin itself is also indicated to have a therapeutic effect when administered in vivo in amellorating such conditions.

We claim:

1. Therapeutic, diagnostic or prophylactic compositions comprising natural minactivin and a pharmaceutically acceptable non-toxic carrier thereof.

2. Antibody preparations directed to a compound selected from the group consisting of recombinant minactivin and natural minactivin.

3. Therapeutic, diagnostic or prophylactic compositions comprising recombinant minactivin and a pharmaceutically acceptable non-toxic carrier therefor.

4. Therapeutic, diagnostic or prophylactic compositions comprising antibodies directed to natural minactivin and a pharmaceutically acceptable non-toxic carrier therefor.

5. Therapeutic, diagnostic or prophylactic compositions comprising antibodies directed to recombinant minactivin and a pharmaceutically acceptable non-toxic carrier therefor.

* * * * *

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
( A ) LENGTH: 21 amino acids
( B ) TYPE: amino acid
( D ) TOPOLOGY: unknown ( i i ) MOLECULE TYPE: peptide ( v ) FRAGMENT TYPE: internal ( x i ) SEQUENCE DESCRIPTION: SEQ ID NO:1:

```
Ala Gln Ile Leu Glu Leu Pro Tyr Xaa Gly Asp Val Xaa Met Phe Leu
 1               5                  10                  15

Leu Leu Pro Xaa Glu
             20
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( D ) TOPOLOGY: unknown ( i i ) MOLECULE TYPE: peptide ( v ) FRAGMENT TYPE: internal ( x i ) SEQUENCE DESCRIPTION: SEQ ID NO:2:

```
Gly Arg Ala Asn Phe Ser Gly Met Ser Glu Xaa Asn Asp Leu Phe
 1               5                  10                  15
```

( 2 ) INFORMATION FOR SEQ ID NO:3:

( i ) SEQUENCE CHARACTERISTICS:
        ( A ) LENGTH: 19 amino acids
        ( B ) TYPE: amino acid
        ( D ) TOPOLOGY: unknown ( i i ) MOLECULE TYPE: peptide ( v ) FRAGMENT TYPE: internal ( x i ) SEQUENCE DESCRIPTION: SEQ ID NO:3:

```
Met Ala Glu Xaa Glu Val Glu Val Tyr Ile Pro Gln Phe Lys Leu Glu
 1               5                  10                  15

Glu Xaa Tyr
```

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( v ) FRAGMENT TYPE: internal ( x i ) SEQUENCE DESCRIPTION: SEQ ID NO:4:

```
Leu Asn Ile Gly Tyr Ile Glu Asp Leu Lys
 1               5                  10
```

( 2 ) INFORMATION FOR SEQ ID NO:5:

( i ) SEQUENCE CHARACTERISTICS:
        ( A ) LENGTH: 10 amino acids
        ( B ) TYPE: amino acid
        ( D ) TOPOLOGY: unknown ( i i ) MOLECULE TYPE: peptide ( v ) FRAGMENT TYPE: internal ( x i ) SEQUENCE DESCRIPTION: SEQ ID NO:5:

```
Ile Pro Asn Leu Leu Pro Glu Gly Xaa Val
 1               5                  10
```

(2) INFORMATION FOR SEQ ID NO:6:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (ix) FEATURE:
        (A) NAME/KEY: modified_base
        (B) LOCATION: 12
        (D) OTHER INFORMATION: /mod_base=i (xi) SEQUENCE DESCRIPTION: SEQ ID NO:6:

TTRAAYTGNA CNATRTA                                                          17

(2) INFORMATION FOR SEQ ID NO:7:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (xi) SEQUENCE DESCRIPTION: SEQ ID NO:7:

TANACYTCNA CYTC                                                             14

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA oligonucleotide (iv) ANTI-SENSE: YES (ix) FEATURE:
        (A) NAME/KEY: modified_base
        (B) LOCATION: 6
        (D) OTHER INFORMATION: /mod_base=i (xi) SEQUENCE DESCRIPTION: SEQ ID NO:8:

TCBARNATNT GVGC                                                             14

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: Other nucleic acid;
        (A) DESCRIPTION: Synthetic DNA olgonucleotide (iv) ANTI-SENSE: YES (ix) FEATURE:
        (A) NAME/KEY: modified_base
        (B) LOCATION: 9
        (D) OTHER INFORMATION: /mod_base=i ( i x ) FEATURE:
  ( A ) NAME/KEY: modified_base
  ( B ) LOCATION: 12
  ( D ) OTHER INFORMATION: /mod_base=i ( i x ) FEATURE:
  ( A ) NAME/KEY: modified_base
  ( B ) LOCATION: 18
  ( D ) OTHER INFORMATION: /mod_base=i ( i x ) FEATURE:
  ( A ) NAME/KEY: modified_base
  ( B ) LOCATION: 24
  ( D ) OTHER INFORMATION: /mod_base=i ( x i ) SEQUENCE DESCRIPTION: SEQ ID NO:9:

TTGAAYTGNA CNATGTANAC YTCNACYTC                29

( 2 ) INFORMATION FOR SEQ ID NO:10:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( i i ) MOLECULE TYPE: Other nucelic acid;
    ( A ) DESCRIPTION: Synthetic DNA oligonucleotide ( i v ) ANTI-SENSE: YES ( i x ) FEATURE:
    ( A ) NAME/KEY: modified_base
    ( B ) LOCATION: 6
    ( D ) OTHER INFORMATION: /mod_base=i ( i x ) FEATURE:
    ( A ) NAME/KEY: modified_base
    ( B ) LOCATION: 15
    ( D ) OTHER INFORMATION: /mod_base=i ( x i ) SEQUENCE DESCRIPTION: SEQ ID NO:10:

TCYTCNATRT ANCCNATRTT                          20

( 2 ) INFORMATION FOR SEQ ID NO:11:

( i ) SEQUENCE CHARACTERISTICS:
    ( A ) LENGTH: 14 base pairs
    ( B ) TYPE: nucleic acid
    ( C ) STRANDEDNESS: single
    ( D ) TOPOLOGY: linear ( i i ) MOLECULE TYPE: Other nucleic acid;
    ( A ) DESCRIPTION: Synthetic DNA oligonucleotide ( i v ) ANTI-SENSE: YES ( i x ) FEATURE:
    ( A ) NAME/KEY: modified_base
    ( B ) LOCATION: 3
    ( D ) OTHER INFORMATION: /mod_base=i ( i x ) FEATURE:
    ( A ) NAME/KEY: modified_base
    ( B ) LOCATION: 9
    ( D ) OTHER INFORMATION: /mod_base=i ( x i ) SEQUENCE DESCRIPTION: SEQ ID NO:11:

AANTTNGCNC KNCC                                14

( 2 ) INFORMATION FOR SEQ ID NO:12:

( i ) SEQUENCE CHARACTERISTICS:
    ( A ) LENGTH: 57 base pairs
    ( B ) TYPE: nucleic acid (C) STRANDEDNESS: single
(D) TOPOLOGY: linear (ii) MOLECULE TYPE: Other nucleic acid;
(A) DESCRIPTION: Synthetic DNA oligonucleotide (iv) ANTI-SENSE: YES (xi) SEQUENCE DESCRIPTION: SEQ ID NO:12:

ATATGTTTCC TCGAGCTTGA ACTGAGGGAT GTACACCTCG ACTTCGCTCT CTGCCAT  57

(2) INFORMATION FOR SEQ ID NO:13:

(i) SEQUENCE CHARACTERISTICS:
(A) LENGTH: 66 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (iv) ANTI-SENSE: YES (xi) SEQUENCE DESCRIPTION: SEQ ID NO:13:

TTCATCAGGC AACAGGAGGA ACATGCTCAC ATCTCCGGCG TAAGGGAGTT CCAGGATCTT  60

CATTTT  66

(2) INFORMATION FOR SEQ ID NO:14:

(i) SEQUENCE CHARACTERISTICS:
(A) LENGTH: 39 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (iv) ANTI-SENSE: YES (xi) SEQUENCE DESCRIPTION: SEQ ID NO:14:

CTCCTCCAGC TTGAACTGGG GGATGTAGAC CTCCACCTC  39

(2) INFORMATION FOR SEQ ID NO:15:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (iv) ANTI-SENSE: YES (xi) SEQUENCE DESCRIPTION: SEQ ID NO:15:

CTTGAACTGR GGRATGTASA CCTCCACCTC  30

(2) INFORMATION FOR SEQ ID NO:16:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: Other nucleic acid;
(A) DESCRIPTION: Synthetic DNA oligonucleotide (iv) ANTI-SENSE: YES 5,426,044

41 42

-continued ( x i ) SEQUENCE DESCRIPTION: SEQ ID NO:16:

TTCCAGTAAA TAATTCCCTG TGGATGCATT 30

( 2 ) INFORMATION FOR SEQ ID NO:17:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: Other nucleic acid;
        ( A ) DESCRIPTION: Synthetic DNA oligonucleotide ( i v ) ANTI-SENSE: YES ( x i ) SEQUENCE DESCRIPTION: SEQ ID NO:17:

GCCTGCAAAA TCGCATCAGG ATAACTACC 29

( 2 ) INFORMATION FOR SEQ ID NO:18:

( i ) SEQUENCE CHARACTERISTICS:
        ( A ) LENGTH: 2409 base pairs
        ( B ) TYPE: nucleic acid
        ( C ) STRANDEDNESS: double
        ( D ) TOPOLOGY: unknown ( i i ) MOLECULE TYPE: cDNA to genomic RNA ( i x ) FEATURE:
        ( A ) NAME/KEY: CDS
        ( B ) LOCATION: 49..1296

( x i ) SEQUENCE DESCRIPTION: SEQ ID NO:18:

```
GTCAGACAGC AACTCAGAGA ATAACCAGAG AACAACCAGA TTGAAACA ATG GAG GAT       57
                                                        Met Glu Asp
                                                          1

CTT TGT GTG GCA AAC ACA CTC TTT GCC CTC AAT TTA TTC AAG CAT CTG       105
Leu Cys Val Ala Asn Thr Leu Phe Ala Leu Asn Leu Phe Lys His Leu
      5                  10                  15

GCA AAA GCA AGC CCC ACC CAG AAC CTC TTC CTC TCC CCA TGG AGC ATC       153
Ala Lys Ala Ser Pro Thr Gln Asn Leu Phe Leu Ser Pro Trp Ser Ile
 20                  25                  30                  35

TCG TCC ACC ATG GCC ATG GTC TAC ATG GGC TCC AGG GGC AGC ACC GAA       201
Ser Ser Thr Met Ala Met Val Tyr Met Gly Ser Arg Gly Ser Thr Glu
                 40                  45                  50

GAC CAG ATG GCC AAG GTG CTT CAG TTT AAT GAA GTG GGA GCC AAT GCA       249
Asp Gln Met Ala Lys Val Leu Gln Phe Asn Glu Val Gly Ala Asn Ala
             55                  60                  65

GTT ACC CCC ATG ACT CCA GAG AAC TTT ACC AGC TGT GGG TTC ATG CAG       297
Val Thr Pro Met Thr Pro Glu Asn Phe Thr Ser Cys Gly Phe Met Gln
         70                  75                  80

CAG ATC CAG AAG GGT AGT TAT CCT GAT GCG ATT TTG CAG GCA CAA GCT       345
Gln Ile Gln Lys Gly Ser Tyr Pro Asp Ala Ile Leu Gln Ala Gln Ala
     85                  90                  95

GCA GAT AAA ATC CAT TCA TCC TTC CGC TCT CTC AGC TCT GCA ATC AAT       393
Ala Asp Lys Ile His Ser Ser Phe Arg Ser Leu Ser Ser Ala Ile Asn
100                 105                 110                 115

GCA TCC ACA GGG AAT TAT TTA CTG GAA AGT GTC AAT AAG CTG TTT GGT       441
Ala Ser Thr Gly Asn Tyr Leu Leu Glu Ser Val Asn Lys Leu Phe Gly
                 120                 125                 130

GAG AAG TCT GCG AGC TTC CGG GAA GAA TAT ATT CGA CTC TGT CAG AAA       489
Glu Lys Ser Ala Ser Phe Arg Glu Glu Tyr Ile Arg Leu Cys Gln Lys
             135                 140                 145

TAT TAC TCC TCA GAA CCC CAG GCA GTA GAC TTC CTA GAA TGT GCA GAA       537
Tyr Tyr Ser Ser Glu Pro Gln Ala Val Asp Phe Leu Glu Cys Ala Glu
         150                 155                 160
```

```
GAA GCT AGA AAA AAG ATT AAT TCC TGG GTC AAG ACT CAA ACC AAA GGC    585
Glu Ala Arg Lys Lys Ile Asn Ser Trp Val Lys Thr Gln Thr Lys Gly
    165                 170                 175

AAA ATC CCA AAC TTG TTA CCT GAA GGT TCT GTA GAT GGG GAT ACC AGG    633
Lys Ile Pro Asn Leu Leu Pro Glu Gly Ser Val Asp Gly Asp Thr Arg
180                     185                 190                 195

ATG GTC CTG GTG AAT GCT GTC TAC TTC AAA GGA AAG TGG AAA ACT CCA    681
Met Val Leu Val Asn Ala Val Tyr Phe Lys Gly Lys Trp Lys Thr Pro
                    200                 205                 210

TTT GAG AAG AAA CTA AAT GGG CTT TAT CCT TTC CGT GTA AAC TCG GCT    729
Phe Glu Lys Lys Leu Asn Gly Leu Tyr Pro Phe Arg Val Asn Ser Ala
                215                 220                 225

CAG CGC ACA CCT GTA CAG ATG ATG TAC TTG CGT GAA AAG CTA AAC ATT    777
Gln Arg Thr Pro Val Gln Met Met Tyr Leu Arg Glu Lys Leu Asn Ile
        230                 235                 240

GGA TAC ATA GAA GAC CTA AAG GCT CAG ATT CTA GAA CTC CCA TAT GCT    825
Gly Tyr Ile Glu Asp Leu Lys Ala Gln Ile Leu Glu Leu Pro Tyr Ala
    245                 250                 255

GGA GAT GTT AGC ATG TTC TTG TTG CTT CCA GAT GAA ATT GCC GAT GTG    873
Gly Asp Val Ser Met Phe Leu Leu Leu Pro Asp Glu Ile Ala Asp Val
260                 265                 270                 275

TCC ACT GGC TTG GAG CTG CTG GAA AGT GAA ATA ACC TAT GAC AAA CTC    921
Ser Thr Gly Leu Glu Leu Leu Glu Ser Glu Ile Thr Tyr Asp Lys Leu
                280                 285                 290

AAC AAG TGG ACC AGC AAA GAC AAA ATG GCT GAA GAT GAA GTT GAG GTA    969
Asn Lys Trp Thr Ser Lys Asp Lys Met Ala Glu Asp Glu Val Glu Val
                295                 300                 305

TAC ATA CCC CAG TTC AAA TTA GAA GAG CAT TAT GAA CTC AGA TCC ATT   1017
Tyr Ile Pro Gln Phe Lys Leu Glu Glu His Tyr Glu Leu Arg Ser Ile
        310                 315                 320

CTG AGA AGC ATG GGC ATG GAG GAC GCC TTC AAC AAG GGA CGG GCC AAT   1065
Leu Arg Ser Met Gly Met Glu Asp Ala Phe Asn Lys Gly Arg Ala Asn
    325                 330                 335

TTC TCA GGG ATG TCG GAG AGG AAT GAC CTG TTT CTT TCT GAA GTG TTC   1113
Phe Ser Gly Met Ser Glu Arg Asn Asp Leu Phe Leu Ser Glu Val Phe
340                 345                 350                 355

CAC CAA GCC ATG GTG GAT GTG AAT GAG GAG GGC ACT GAA GCA GCC GCT   1161
His Gln Ala Met Val Asp Val Asn Glu Glu Gly Thr Glu Ala Ala Ala
                360                 365                 370

GGC ACA GGA GGT GTT ATG ACA GGG AGA ACT GGA CAT GGA GGC CCA CAG   1209
Gly Thr Gly Gly Val Met Thr Gly Arg Thr Gly His Gly Gly Pro Gln
                375                 380                 385

TTT GTG GCA GAT CAT CCT TTT CTT TTT CTT ATT ATG CAT AAG ATA ACC   1257
Phe Val Ala Asp His Pro Phe Leu Phe Leu Ile Met His Lys Ile Thr
        390                 395                 400

AAC TGC ATT TTA TTT TTC GGC AGA TTT TCC TCA CCC TAAAACTAAG        1303
Asn Cys Ile Leu Phe Phe Gly Arg Phe Ser Ser Pro
    405                 410                 415

CGTGCTGCTT CTGCAAAAGA TTTTGTAGA TGAGCTGTGT GCCTCAGAAT TGCTATTTCA   1363

AATTGCCAAA AATTTAGAGA TGTTTTCTAC ATATTTCTGC TCTTCTGAAC AACTTCTGCT   1423

ACCCACTAAA TAAAACACA GAAATAATTA GACAATTGTC TATTATAACA TGACAACCCT    1483

ATTAATCATT TGGTCTTCTA AAATGGGATC ATGCCCATTT AGATTTTCCT TACTATCAGT   1543

TTATTTTTAT AACATTAACT TTTACTTTGT TATTTATTAT TTTATATAAT GGTGAGTTTT   1603

TAAATTATTG CTCACTGCCT ATTTAATGTA GCTAATAAAG TTATAGAAGC AGATGATCTG   1663

TTAATTTCCT ATCTAATAAA TGCCTTTAAT TGTTCTCATA ATGAAGAATA AGTAGGTATC   1723

CCTCCATGCC CTTCTGTAAT AAATATCTGG AAAAAACATT AAACAATAGG CAAATATATG   1783

TTATGTGCAT TTCTAGAAAT ACATAACACA TATATATGTC TGTATCTTAT ATTCAATTGC   1843
```

```
AAGTATATAA TGTCATAATT TCAAGACCAG CCTGGCCAAC ATAGCGAAAC CCTACCTCCA    1903
CTAAAAATAC AGAAATGAGC CGGGAGTGGT GGCAAAGTGG TGAGCACCTG TGATCCCAGC    1963
CACTGTGGAG GCCGAGGCAG GACAATCACT TGAACCCAGG AGGCGGAGGC TGCAGTGAGC    2023
TGAGATCGCT CCACTGCACT CCAGCCTGGG CAACAGAGCA AGATTCCATC TCAAAATACA    2083
TTAAAAAAAA AAACCTATCT GAGGACTCTG AAAAGTAAAT GGTAGCAGAT AGATTTGAGA    2143
AGGGAACTAG AACTTGAAGC ACAATCTATC TGGTGCTCTT TCTTACTTTT GCTTGTTTTC    2203
TCCCAATCTT CCAGTCTGGA TACAAAGGCA GCCCAATTTC TAGAAATGTA TACCAGCCAT    2263
GAAGAGATAA AGCTCCAAGA GGAGATTTCT CTTTCTGGTA TAAGGTATGT GTGTGTATAT    2323
GGGGGGCGAT AAGGTTGGGA GTGTGAGGAA TACAGAGTCG GAGAAATCCA TTATTTCCAC    2383
CCTCTCTCTT GCCATTGCAA CCAGAC                                        2409
```

( 2 ) INFORMATION FOR SEQ ID NO:19:

( i ) SEQUENCE CHARACTERISTICS:
        ( A ) LENGTH: 415 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Met Glu Asp Leu Cys Val Ala Asn Thr Leu Phe Ala Leu Asn Leu Phe
 1               5                  10                  15

Lys His Leu Ala Lys Ala Ser Pro Thr Gln Asn Leu Phe Leu Ser Pro
                20                  25                  30

Trp Ser Ile Ser Ser Thr Met Ala Met Val Tyr Met Gly Ser Arg Gly
            35                  40                  45

Ser Thr Glu Asp Gln Met Ala Lys Val Leu Gln Phe Asn Glu Val Gly
        50                  55                  60

Ala Asn Ala Val Thr Pro Met Thr Pro Glu Asn Phe Thr Ser Cys Gly
 65                 70                  75                  80

Phe Met Gln Gln Ile Gln Lys Gly Ser Tyr Pro Asp Ala Ile Leu Gln
                85                  90                  95

Ala Gln Ala Ala Asp Lys Ile His Ser Ser Phe Arg Ser Leu Ser Ser
            100                 105                 110

Ala Ile Asn Ala Ser Thr Gly Asn Tyr Leu Leu Glu Ser Val Asn Lys
        115                 120                 125

Leu Phe Gly Glu Lys Ser Ala Ser Phe Arg Glu Glu Tyr Ile Arg Leu
130                 135                 140

Cys Gln Lys Tyr Tyr Ser Ser Glu Pro Gln Ala Val Asp Phe Leu Glu
145                 150                 155                 160

Cys Ala Glu Glu Ala Arg Lys Lys Ile Asn Ser Trp Val Lys Thr Gln
                165                 170                 175

Thr Lys Gly Lys Ile Pro Asn Leu Leu Pro Glu Gly Ser Val Asp Gly
            180                 185                 190

Asp Thr Arg Met Val Leu Val Asn Ala Val Tyr Phe Lys Gly Lys Trp
        195                 200                 205

Lys Thr Pro Phe Glu Lys Lys Leu Asn Gly Leu Tyr Pro Phe Arg Val
        210                 215                 220

Asn Ser Ala Gln Arg Thr Pro Val Gln Met Met Tyr Leu Arg Glu Lys
225                 230                 235                 240

Leu Asn Ile Gly Tyr Ile Glu Asp Leu Lys Ala Gln Ile Leu Glu Leu
                245                 250                 255

Pro Tyr Ala Gly Asp Val Ser Met Phe Leu Leu Leu Pro Asp Glu Ile
```

|   |   |   |   |   |   |   |   |   |   |   |   |   |   |   |
|---|---|---|---|---|---|---|---|---|---|---|---|---|---|---|
|   |   | 260 |   |   |   | 265 |   |   |   |   | 270 |   |   |   |
| Ala | Asp | Val | Ser | Thr | Gly | Leu | Glu | Leu | Leu | Glu | Ser | Glu | Ile | Thr | Tyr |
|   |   | 275 |   |   |   | 280 |   |   |   |   | 285 |   |   |   |
| Asp | Lys | Leu | Asn | Lys | Trp | Thr | Ser | Lys | Asp | Lys | Met | Ala | Glu | Asp | Glu |
|   |   | 290 |   |   |   | 295 |   |   |   |   | 300 |   |   |   |
| Val | Glu | Val | Tyr | Ile | Pro | Gln | Phe | Lys | Leu | Glu | Glu | His | Tyr | Glu | Leu |
| 305 |   |   |   |   | 310 |   |   |   |   | 315 |   |   |   |   | 320 |
| Arg | Ser | Ile | Leu | Arg | Ser | Met | Gly | Met | Glu | Asp | Ala | Phe | Asn | Lys | Gly |
|   |   |   |   | 325 |   |   |   |   | 330 |   |   |   |   | 335 |   |
| Arg | Ala | Asn | Phe | Ser | Gly | Met | Ser | Glu | Arg | Asn | Asp | Leu | Phe | Leu | Ser |
|   |   |   | 340 |   |   |   |   | 345 |   |   |   |   | 350 |   |   |
| Glu | Val | Phe | His | Gln | Ala | Met | Val | Asp | Val | Asn | Glu | Glu | Gly | Thr | Glu |
|   |   | 355 |   |   |   |   | 360 |   |   |   |   | 365 |   |   |   |
| Ala | Ala | Ala | Gly | Thr | Gly | Gly | Val | Met | Thr | Gly | Arg | Thr | Gly | His | Gly |
|   |   | 370 |   |   |   | 375 |   |   |   |   | 380 |   |   |   |   |
| Gly | Pro | Gln | Phe | Val | Ala | Asp | His | Pro | Phe | Leu | Phe | Leu | Ile | Met | His |
| 385 |   |   |   |   | 390 |   |   |   |   | 395 |   |   |   |   | 400 |
| Lys | Ile | Thr | Asn | Cys | Ile | Leu | Phe | Phe | Gly | Arg | Phe | Ser | Ser | Pro |   |
|   |   |   |   | 405 |   |   |   |   | 410 |   |   |   |   | 415 |   |